United States Patent
Steinmeyer et al.

(10) Patent No.: US 6,531,459 B1
(45) Date of Patent: Mar. 11, 2003

(54) VITAMIN D DERIVATIVES WITH PHOSPHORUS ATOMS IN THE SIDE CHAINS

(75) Inventors: Andreas Steinmeyer, Berlin (DE); Günter Neef, Berlin (DE); Gerald Kirsch, Berlin (DE); Katica Schwarz, Berlin (DE); Herbert Wiesinger, Berlin (DE); Martin Haberey, Berlin (DE); Marianne Fähnrich, Berlin (DE); Gernot Langer, Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/581,907

(22) PCT Filed: Dec. 16, 1998

(86) PCT No.: PCT/EP98/08137

§ 371 (c)(1), (2), (4) Date: Aug. 4, 2000

(87) PCT Pub. No.: WO99/31112

PCT Pub. Date: Jun. 24, 1999

(30) Foreign Application Priority Data

Dec. 17, 1997 (DE) .......................... 197 58 119

Dec. 17, 1997 (EP) ............................ 97250374

(51) Int. Cl.$^7$ ..................... A61K 31/59; C07C 403/00
(52) U.S. Cl. ........................... 514/167; 552/653
(58) Field of Search ........................ 552/653; 514/167

(56) References Cited

U.S. PATENT DOCUMENTS

| | | | |
|---|---|---|---|
| 4,230,700 A | | 10/1980 | Francis |
| 6,121,312 A | * | 9/2000 | Reddy ........................ 514/451 |

FOREIGN PATENT DOCUMENTS

| | | |
|---|---|---|
| EP | 0 633 245 A1 | 1/1995 |
| WO | 90 09992 | 9/1990 |
| WO | 98 35704 | 8/1998 |

* cited by examiner

*Primary Examiner*—Barbara P. Badio
(74) *Attorney, Agent, or Firm*—Millen, White, Zelano & Branigan, P.C.

(57) ABSTRACT

Described are new vitamin D derivatives such as of the formula (I) detailed in this disclosure. Also described are methods for preparing these derivatives, inter mediates used to prepare the derivatives and use of the derivatives as pharmaceutical agents.

16 Claims, 1 Drawing Sheet

Figure 1/1:
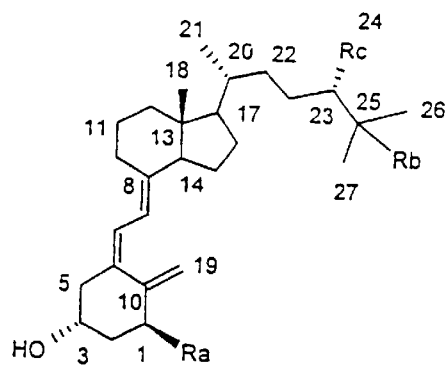
| Ergocalciferol | Ra=Rb=H, Rc=CH₃, double bond C-22/23 | Vitamin D₂ |
|---|---|---|
| Cholecalciferol | Ra=Rb=Rc=H | Vitamin D₃ |
| 25-Hydroxycholecalciferol | Ra=Rc=H, Rb=OH | |
| 1α-Hydroxycholecalciferol | Ra=OH, Rb=Rc=H | |
| 1α,25-Dihydroxycholecalciferol | Ra=Rb=OH, Rc=H | Calcitriol |

VITAMIN D DERIVATIVES WITH PHOSPHORUS ATOMS IN THE SIDE CHAINS

This application is a 371 of PCT/EP98/08137 filed Dec. 16, 1998.

The invention relates to new vitamin D derivatives of general formula I

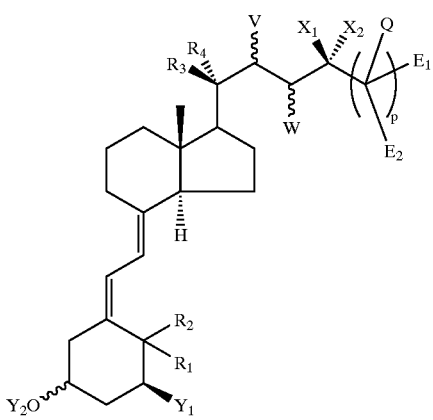

process for their production, intermediate products of the process as well as the use for the production of pharmaceutical agents.

PRIOR ART

Natural vitamins $D_2$ and $D_3$ are inherently biologically inactive and are converted into biologically active metabolites [1α,25-dihydroxy vitamin $D_3$ (calcitriol) or -$D_2$] only after hydroxylation at C-atom 25 in the liver and at C-atom 1 in the kidney. The action of the active metabolites involves the regulation of the calcium and phosphate concentration in the serum; they counteract a dropping of the calcium concentration in the serum by increasing the calcium absorption in the intestine and under certain circumstances promoting calcium mobilization from the bones. FIG. 1 shows the structure of some known vitamin D derivatives.

In addition to their pronounced effect on the calcium and phosphate metabolism, the active metabolites of vitamins $D_2$ and $D_3$ and their synthetic derivatives have a proliferation-inhibiting and differentiation-stimulating action on tumor cells and normal cells, such as, for example, skin cells. In addition, a pronounced effect on cells of the immune system (inhibiting of proliferation and interleukin 2-synthesis of lymphocytes, increase of cytotoxicity and phagocytosis in vitro of monocytes) has been found, which manifests itself in an immunomodulatory action, and finally, because of a stimulating action on bone-forming cells, an increased formation of bone in normal and osteoporotic rats is found [R. Bouillon et al. "Short Term Course of 1,25-$(OH)_2D_3$ Stimulates Osteoblasts But Not Osteoclasts," Calc. Tissue Int. 49, 168 (1991)].

All actions are mediated by bonding to the vitamin D receptor. Because of the bonding, the activity of specific genes is regulated.

When biologically active metabolites of vitamins $D_2$ and $D_3$ are used, a toxic effect on the calcium metabolism is produced (hypercalcemia).

By structural manipulations of the side chain, therapeutically usable effectiveness can be separated from undesirable hypercalcemic activity. A suitable structural variant is the introduction of a 24-hydroxy group.

1α-Cholecalciferols that are hydroxylated in 24-position are already described in DE 25 26 981. They have a lower toxicity than the corresponding non-hydroxylated 1α-cholecalciferol. Further, 24-hydroxy derivatives are described in the following patent applications: DE 39 33 034, DE 40 03 854, DE 40 34 730, EP 0 421 561, EP 0 441 467, WO 87/00834, and WO 91/12238.

Finally, 25-carboxylic acid derivatives of calcitriol that are hydroxylated at C-24 are described in WO 94/07853, and said derivatives exhibit a more advantageous spectrum of action than calcitriol. The equivalent is also true for new vitamin D derivatives with other substituents at C-25 (WO 97/00242). While the ability to trigger a hypercalcemia is considerably weakened, proliferation-inhibiting and differentiation-stimulating actions are maintained. Generally, however, the introduction of the 24-hydroxyl group results in metabolic destabilization of the derivatives, especially if a cyclopropyl ring is in the neighboring position. For this reason, these compounds are only conditionally suitable for systemic administration.

There is therefore a need for new vitamin D derivatives that have as advantageous or improved a spectrum of action as the compounds that are described in the prior art (especially WO 94/07853 and WO 97/00242), but that are better suited for systemic administration owing to their higher metabolic stability.

The object of this patent application is therefore to make available such vitamin D derivatives. This object is achieved by the compounds that are disclosed in the claims.

This invention therefore relates to vitamin D derivatives of general formula I,

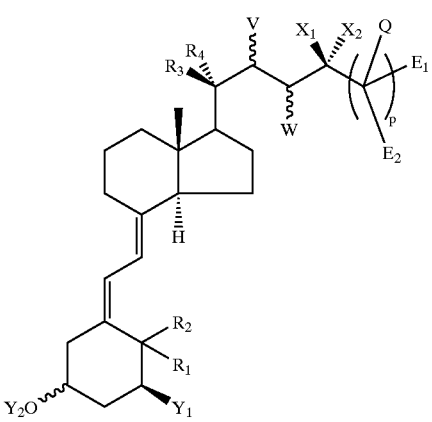

in which
$Y_1$ means a hydrogen atom, a hydroxyl group, a fluorine, chlorine or bromine atom or a group —O(CO)$R_5$, in which
$R_5$ is an aliphatic or aromatic radical with 1 to 12 C atoms,
$Y_2$ means a hydrogen atom or a group —(CO)$R_6$, in which
$R_6$ is an aliphatic or aromatic radical with 1 to 12 C atoms,
and group $Y_2O$ can be present both in naturally occurring situation (3β) and in epimeric situation (3α),
$R_1$ and $R_2$ each mean a hydrogen atom or together an exocyclic methylene group, $R_3$ and $R_4$, independently of one another, mean a hydrogen atom, a chlorine or fluorine atom, an alkyl group with 1 to 4 carbon atoms, together a methylene group or together with quaternary carbon atom 20 a 3- to 7-membered, saturated or unsaturated carbocyclic ring, V and W together mean an E-double bond or V means a hydroxyl group and W means a hydrogen atom, or V and W each mean hydrogen atoms, $X_1$ and $X_2$, independently of one another, mean a hydrogen atom, a hydroxyl group, a group —$OR_7$ or $O(CO)R_7$, in which
  $R_7$ is an aliphatic or aromatic radical with 1 to 12 C atoms,
  or a group $PO(OR_8)_2$, a group $PO(N(R_8)_2)_2$ or a group $PO(R_8)_2$, a group $OPO(OR_8)_2$, a group $OPO(N(R_8)_2)_2$ or a group $OPO(R_8)_2$ or a group $CH_2$—$PO(OR_8)_2$, a group $CH_2$—$PO(N(R_8)_2)_2$ or a group $CH_2$—$PO(R_8)_2$, in which
  $R_8$, independently of one another, are a hydrogen atom or an aliphatic or aromatic radical with 1 to 12 C atoms,
or $X_1$ and $X_2$ together stand for a carbonyl group, p means the number 1 or 0, $E_1$ means a group $PO(OR_9)_2$, a group $PO(N(R_9)_2)_2$, a group $PO(R_9)_2$ or a group $CO_2R_9$ in which
  $R_9$, independently of one another, are a hydrogen atom or an aliphatic or aromatic radical with 1 to 12 C atoms, $E_2$ means a group $PO(OR_9)_2$, a group $PO(N(R_9)_2)_2$, a group $PO(R_9)_2$, a halogen atom (fluorine, chlorine, bromine), an aliphatic or aromatic radical with 1 to 12 C atoms or a hydrogen atom, Q means a hydrogen atom, an aliphatic or aromatic radical with 1 to 12 C atoms, a hydroxyl group, a group —$O(CO)R_{10}$, a fluorine, chlorine or bromine atom, an amino group or an $NHR_{10}$ or $N(R_{10})_2$ group, in which
  $R_{10}$ is an aliphatic or aromatic radical with 1 to 12 C atoms,
or $X_1$ and $E_2$ together mean a double bond and at the same time $X_2$ means a hydrogen atom or a group O—Z, in which
  Z means an aliphatic or aromatic radical with 1 to 12 C atoms, an aliphatic or aromatic acyl group with 1 to 12 C atoms or a group $E_2$,
or $X_1$, $X_2$, $E_2$ and Q together mean a triple bond.

The invention also relates to a process for the production of the compounds according to the invention, intermediate products of the production process as well as the use of the compounds according to the invention for the production of pharmaceutical agents.

Especially advantageous embodiments of the invention are the subject of the subclaims.

Groups $E_1$ and $E_2$, i.a., stand for phosphonic acid derivatives or carboxylic acid derivatives or for phosphine oxide derivatives. The term phosphonic acid derivatives or carboxylic acid derivatives comprises the free phosphonic acids or carboxylic acids (—$PO_3H_2$, —$CO_2H$), phosphonic- or carboxylic acid esters (—$PO_3(R_9)_2$, —$CO_2R_9$), phosphonic- or carboxylic acid amides (e. g., —$PO(N(R_9)_2)_2$, —$CO(NR_9)_2$, —$PO(NHR_9)_2$, —$CO_2NHR_9$), but also phosphonic acid monoesters or -amides, such as, e.g., $PO(OH)OR_9$, $PO(OH)N(R_9)_2$.

Groups $X_1$ and $X_2$, i.a., stand for hydrogen atoms, hydroxyl groups, etherified or esterified hydroxyl groups. They can also stand for ($E_1$ and $E_2$) already defined above under phosphoric acid derivatives (—$PO_3H_2$, —$PO_3(R_8)_2$, —$PO(N(R_8)_2)_2$, —$PO(NHR_8)_2$, but also phosphonic acid monoesters or amides). This conformation and its synthesis is described in, for example, Example 29. Groups $X_1$ and $X_2$ together can also stand for a carbonyl group, however (see, e.g., Example 10).

It is common in all compounds according to the invention that at least one phosphorus-containing group is contained that is bonded to the vitamin D skeleton by a phosphorus-carbon bonding. Especially preferred are compounds in which both groups ($E_1$ and $E_2$) stand for phosphonic acid derivatives.

Index p stands for numbers 1 or 0. If p stands for 0, this means that C atom 25 does not exist, and group E1 is bonded directly to C-24. This conformation and its synthesis is described by way of example in Examples 29 and 30.

Groups $R_3$ and $R_4$, independently of one another, can mean a hydrogen atom, a chlorine or fluorine atom, an alkyl group with 1 to 4 carbon atoms (methyl, ethyl, n-propyl, i-propyl, n-butyl, i-butyl, t-butyl), together a methylene group or together with quaternary carbon atom 20 a 3- to 7-membered saturated or unsaturated carbocyclic ring.

For $R_3$ and $R_4$, the following preferred combinations apply: $R_3$=H, $R_4$=methyl or $R_3$=methyl, $R_4$=H; $R_3$=F, $R_4$=methyl or $R_3$=methyl, $R_4$=F; $R_3$, $R_4$=methyl; $R_3$ and $R_4$ together form a methylene group or together with quaternary carbon atom 20 form a cyclopropyl ring.

Optional radicals $R_5$, $R_6$, $R_7$, $R_8$, $R_9$ and $R_{10}$ are organic groups with 1 to 12 C atoms. These radicals can be saturated or unsaturated, branched or unbranched, acyclic, carbocyclic or heterocyclic. Examples of radicals $R_5$, $R_6$, $R_7$, $R_8$, $R_9$ and $R_{10}$ are methyl, ethyl, propyl, i-propyl, butyl or phenyl groups. The radicals of naturally occurring amino acids, such as, e.g., —$CH_2$—$CH(CH_3)_2$, —$CH_2$—Ph, —$CH_2OH$, —$CH(OH)$—$CH_3$, —$CH_2SH$, —$CH_2$—$SCH_3$, —$CH_2CO_2H$, —$CH_2CH_2$—$CO_2H$, —$(CH_2)_4$—$NH_2$, —$(CH_2)_3$—$C(NH)NH_2$, but also the radicals of the amino acids tryptophan, tyrosine or histamine, are also possible, however.

Preferred radicals $R_5$, $R_6$, $R_7$, $R_8$, $R_9$ and $R_{10}$ are derived from $C_1$ to $C_9$ alkanecarboxylic acids, especially $C_2$ to $C_5$ alkanecarboxylic acids, such as, for example, acetic acid, propionic acid, butyric acid or pivaloyl acid. Among the aromatic groups, the phenyl group and substituted phenyl groups are preferred.

Preferred radicals for Y are $Y_1$=a hydroxyl group or —$O(CO)R_5$ and $Y_2$=a hydrogen atom or —$(CO)R_6$. $Y_1$=a hydroxyl group and $Y_2$=a hydrogen atom are especially preferred.

Groups V and W are respectively hydrogen atoms or either together form an E-double bond or V is a hydroxyl group and W is a hydrogen atom. The possibilities for the structural element in question are pictured below:

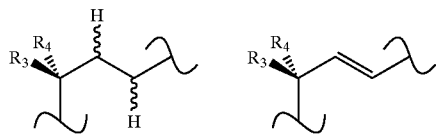

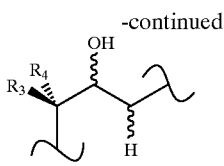

Within the scope of this invention, the following conformation is especially significant: V and W and $X_1$ and $E_2$ in each case mean an E-double bond, while $X_2$ and Q are hydrogen atoms. This conformation and its synthesis is described in, for example, Example 27.

In addition, the conformation is significant that V and W together form an E-double bond, $X_1$ and $E_2$ form an E- or Z-double bond, $X_2$ is a group —OZ, and Q means a hydrogen atom.

In addition, the conformation that $X_1$, $X_2$, $E_2$ and Q together form a triple bond is significant. This conformation and its synthesis is described in, for example, Examples 16 and 17.

Finally, the conformation that $E_2$ and Q are halogen atoms (especially chlorine and fluorine) is of special importance within the scope of this invention. This conformation and its synthesis is described in, for example, Examples 18, 19 and 20.

Of the compounds of general formula I according to the invention, the following compounds are quite especially preferred:

I. (5Z,7E,22E)-(1S,3R)-(1,3-Dihydroxy-24-oxo-24a-homo-9,10-secochola-5,7,10(19),22-tetraen-24a-yl)phosphonic acid dimethyl ester II. (5Z,7E,22E)-(1S,3R,24S)-(1,3,24-Trihydroxy-24a-homo-9,10-secochola-5,7,10(19),22-tetraen-24a-yl) phosphonic acid dimethyl ester III. (5Z,7E,22E)-(1S,3R,24R)-(1,3,24-Trihydroxy-24a-homo-9,10-secochola-5,7,10(19),22-tetraen-24a-yl) phosphonic acid dimethyl ester IV. (5Z,7E,22E)-(1S,3R)-(1,3-Dihydroxy-24-oxo-24a-homo-9,10-secochola-5,7,10(19),22-tetraen-24a-yl) phosphonic acid diethyl ester V. (5Z,7E,22E)-(1S,3R,24S)-(1,3,24-Trihydroxy-24a-homo-9,10-secochola-5,7,10(19),22-tetraen-24a-yl) phosphonic acid diethyl ester VI. (5Z,7E,22E)-(1S,3R,24R)-(1,3,24-Trihydroxy-24a-homo-9,10-secochola-5,7,10(19),22-tetraen-24a-yl) phosphonic acid diethyl ester VII. (5Z,7E,22E)-(1S,3R)-(1,3-Dihydroxy-24-oxo-24a-homo-9,10-secochola-5,7,10(19),22-tetraen-24a-yl) phosphonic acid bis(1-methylethyl)ester VIII. (5Z,7E,22E)-(1S,3R,24S)-(1,3,24-Trihydroxy-24a-homo-9,10-secochola-5,7,10(19),22-tetraen-24a-yl) phosphonic acid bis(1-methylethyl)ester IX. (5Z,7E,22E)-(1S,3R,24R)-(1,3,24-Trihydroxy-24a-homo-9,10-secochola-5,7,10(19),22-tetraen-24a-yl) phosphonic acid bis(1-methylethyl)ester X. (5Z,7E,22E)-(1S,3R)-(1,3-Dihydroxy-24-oxo-24a-homo-9,10-secochola-5,7,10(19),22-tetraen-24a-yl) phosphonic acid dipropyl ester XI. (5Z,7E,22E)-(1S,3R,24S)-(1,3,24-Trihydroxy-24a-homo-9,10-secochola-5,7,10(19),22-tetraen-24a-yl) phosphonic acid dipropyl ester XII. (5Z,7E,22E)-(1S,3R,24R)-(1,3,24-Trihydroxy-24a-homo-9,10-secochola-5,7,10(19),22-tetraen-24a-yl) phosphonic acid dipropyl ester XIII. (5Z,7E,22E)-(1S,3R)-1,3-Dihydroxy-24-oxo-24a-homo-9,10-secochola-5,7,10(19),22-tetraen-24a-yl) phosphonic acid dibutyl ester XIV. (5Z,7E,22E)-(1S,3R24S)-1,3,24-Trihydroxy-24a-homo-9,10-secochola-5,7,10(19),22-tetraen-24a-yl) phosphonic acid dibutyl ester XV. (5Z,7E,22E)-(1S,3R,24R)-(1,3,24-Trihydroxy-24a-homo-9,10-secochola-5,7,10(19),22-tetraen-24a-yl) phosphonic acid dibutyl ester XVI. (5Z,7E,22E)-(1S,3R)-(1,3-Dihydroxy-24-oxo-24a-homo-9,10-secochola-5,7,10(19),22-tetraen-24a-yl) phosphonic acid dipentyl ester XVII. (5Z,7E,22E)-(1S,3R,24S)-(1,3,24-Trihydroxy-24a-homo-9,10-secochola-5,7,10(19),22-tetraen-24a-yl) phosphonic acid dipentyl ester XVIII. (5Z,7E,22E)-(1S,3R,24R)-(1,3,24-Trihydroxy-24a-homo-9,10-secochola-5,7,10(19),22-tetraen-24a-yl) phosphonic acid dipentyl ester XIX. (5Z,7E,22E)-(1S,3R)-(1,3-Dihydroxy-24-oxo-24a-homo-9,10-secochola-5,7,10(19),22-tetraen-24a-yl) phosphonic acid diphenyl ester XX. (5Z,7E,22E)-(1S,3R,24S)-(1,3,24-Trihydroxy-24a-homo-9,10-secochola-5,7,10(19),22-tetraen-24a-yl) phosphonic acid diphenyl ester XXI. (5Z,7E,22E)-(1S,3R,24R)-(1,3,24-Trihydroxy-24a-homo-9,10-secochola-5,7,10(19),22-tetraen-24a-yl) phosphonic acid diphenyl ester XXII. (5Z,7E,22E)-(1S,3R)-(1,3-Dihydroxy-24-oxo-24a-homo-9,10-secochola-5,7,10(19),22-tetraene-24a,24a-diyl)bis[phosphonic acid dimethyl ester]

XXIII. (5Z,7E,22E)-(1S,3R)-(1,3-Dihydroxy-24-oxo-24a-homo-9,10-secochola-5,7,10(19),22-tetraene-24a,24a-diyl)bis[phosphonic acid diethyl ester]

XXIV. (5Z,7E,22E)-(1S,3R)-(1,3-Dihydroxy-24-oxo-24a-homo-9,10-secochola-5,7,10(19),22-tetraene-24a,24a-diyl)bis[phosphonic acid dipropyl ester]

XXV. (5Z,7E,22E)-(1S,3R)-(1,3-Dihydroxy-24-oxo-24a-homo-9,10-secochola-5,7,10(19),22-tetraene-24a,24a-diyl)bis[phosphonic acid dibutyl ester]

XXVI. (5Z,7E,22E)-(1S,3R)-(1,3-Dihydroxy-24-oxo-24a-homo-9,10-secochola-5,7,10(19),22-tetraene-24a,24a-diyl)bis[phosphonic acid bis(1-methylethyl)ester]

XXVII. (5Z,7E,22E)-(1S,3R)-(1,3-Dihydroxy-24-oxo-24a-homo-9,10-secochola-5,7,10(19),22-tetraene-24a,24a-diyl)bis[phosphonic acid diphenyl ester]

XXVIII. (5Z,7E,22E,24E)-(1S,3R)-(1,3-Dihydroxy-24a-homo-9,10-secochola-5,7,10(19),22,24-pentaen-24a-yl) phosphonic acid dimethyl ester XXIX. (5Z,7E,22E,24E)-(1S,3R)-(1,3-Dihydroxy-24a-homo-9,10-secochola-5,7,10(19),22,24-pentaen-24a-yl) phosphonic acid diethyl ester XXX. (5Z,7E,22E,24E)-(1S,3R)-(1,3-Dihydroxy-24a-homo-9,10-secochola-5,7,10(19),22,24-pentaen-24a-yl) phosphonic acid dipropyl ester XXXI. (5Z,7E,22E,24E)-(1S,3R)-(1,3-Dihydroxy-24a-homo-9,10-secochola-5,7,10(19),22,24-pentaen-24a-yl) phosphonic acid dibutyl ester XXXII. (5Z,7E,22E,24E)-(1S,3R)-(1,3-Dihydroxy-24a-homo-9,10-secochola-5,7,10(19),22,24-pentaen-24a-yl) phosphonic acid bis(1-methylethyl)ester XXXIII. (5Z,7E,22E)-(1S,3R)-24-(Diphenylphosphinyl)-9,10-secochola-5,7,10(19),22-tetraene-1,3-diol XXXIV. (5Z,7E,22E)-(1S,3R)-24-(Dimethylphosphinyl)-9,10-secochola-5,7,10(19),22-tetraene-1,3-diol XXXV. (5Z,7E,22E)-(1S,3R)-24-(Diethylphosphinyl)-9,10-secochola-5,7,10(19),22-tetraene-1,3-diol XXXVI. (5Z,7E,22E)-(1S,3R)-24-(Dipropylphosphinyl)-9,10-secochola-5,7,10(19),22-tetraene-1,3-diol XXXVII. (5Z,7E,22E)-(1S,3R)-24-(Dibutylphosphinyl)-9,10-secochola-5,7,10(19),22-tetraene-1,3-diol XXXVIII. (5Z,7E,22E,24E)-(1S,3R)-Phosphoric acid[1,3-Dihydroxy-24a-(dimethoxy)phosphinyl-24a-homo-9,10-secochola-5,7,10(19),22,24-pentaen-24-yl]dimethyl ester XXXIX. (5Z,7E,22E,24Z)-(1S,3R)-Phosphoric acid[1,3-dihydroxy-24a-(dimethoxy)phosphinyl-24a-homo-9,10-secochola-5,7,10(19),22,24-pentaen-24-yl]dimethyl ester XL. (5Z,7E,22E,24E)-(1S,3R)-Phosphoric acid[24a-(diethoxy)phosphinyl-1,3-dihydroxy-24a-homo-9,10-secochola-5,7,10(19),22,24-pentaen-24-yl]diethyl ester XLI. (5Z,7E,22E,24Z)-(1S,3R)-Phosphoric acid[24a-(diethoxy)phosphinyl-1,3-dihydroxy-24a-homo-9,10-secochola-5,7,10(19),22,24-pentaen-24-yl]diethyl ester XLII. (5Z,7E,22E,24E)-(1S,3R)-Phosphoric acid[1,3-dihydroxy-24a-(dipropoxy)phosphinyl-24a-homo-9,10-secochola-5,7,10(19),22,24-pentaen-24-yl]dipropyl ester XLIII. (5Z,7E,22E,24Z)-(1S,3R)-Phosphoric acid[1,3-dihydroxy-24a-(dipropoxy)phosphinyl-24a-homo-9,10-secochola-5,7,10(19),22,24-pentaen-24-yl]dipropyl ester XLIV. (5Z,7E,22E,24E)-(1S,3R)-Phosphoric acid[24a-(dibutoxy)phosphinyl-1,3-dihydroxy-24a-homo-9,10-secochola-5,7,10(19),22,24-pentaen-24-yl]dibutyl ester XLV. (5Z,7E,22E,24Z)-(1S,3R)-Phosphoric acid[24a-(dibutoxy)phosphinyl-1,3-dihydroxy-24a-homo-9,10-secochola-5,7,10(19),22,24-pentaen-24-yl]dibutyl ester XLVI. (5Z,7E,22E,24E)-(1S,3R)-Phosphoric acid[24a-[bis(1-methylethoxy)phosphinyl]-1,3-dihydroxy-24a-homo-9,10-secochola-5,7,10(19),22,24-pentaen-24-yl]bis(1-methylethyl) ester XLVII. (5Z,7E,22E,24Z)-(1S,3R)-Phosphoric acid[24a-[bis(1-methylethoxy)phosphinyl]-1,3-dihydroxy-24a-homo-9,10-secochola-5,7,10(19),22,24-pentaen-24-yl]bis(1-methylethyl)ester XLVIII. (5Z,7E,22E)-(1S,3R)-(1,3-Dihydroxy-24-oxo-24a-homo-9,10-secochola-5,7,10(19),22-tetraen-24a-yl)phosphonic acid-monomethyl ester XLIX. (5Z,7E,22E)-(1S,3R)-(1,3-Dihydroxy-24-oxo-24a-homo-9,10-secochola-5,7,10(19),22-tetraen-24a-yl)phosphonic acid-monoethyl ester L. (5Z,7E,22E)-(1S,3R)-(1,3-Dihydroxy-24-oxo-24a-homo-9,10-secochola-5,7,10(19),22-tetraen-24a-yl)phosphonic acid-mono(1-methylethyl)ester LI. (5Z,7E,22E)-(1S,3R)-(1,3-Dihydroxy-24-oxo-24a-homo-9,10-secochola-5,7,10(19),22-tetraen-24a-yl)phosphonic acid-monopropyl ester LII. (5Z,7E,22E)-(1S,3R)-1,3-Dihydroxy-24-oxo-24a-homo-9,10-secochola-5,7,10(19),22-tetraen-24a-yl)phosphonic acid-monobutyl ester LIII. (5Z,7E,22E)-(1S,3R)-(1,3-Dihydroxy-24-oxo-24a-homo-9,10-secochola-5,7,10(19),22-tetraen-24a-yl)phosphonic acid LIV. (5Z,7E,22E,24E)-(1S,3R)-(1,3-Dihydroxy-24a-homo-9,10-secochola-5,7,10(19),22,24-pentaen-24a-yl)phosphonic acid-monomethyl ester LV. (5Z,7E,22E,24E)-(1S,3R)-(1,3-Dihydroxy-24a-homo-9,10-secochola-5,7,10(19),22,24-pentaen-24a-yl)phosphonic acid-monoethyl ester LVI. (5Z,7E,22E,24E)-(1S,3R)-(1,3-Dihydroxy-24a-homo-9,10-secochola-5,7,10(19),22,24-pentaen-24a-yl)phosphonic acid-mono(1-methylethyl)ester LVII. (5Z,7E,22E,24E)-(1S,3R)-(1,3-Dihydroxy-24a-homo-9,10-secochola-5,7,10(19),22,24-pentaen-24a-yl)phosphonic acid-monopropyl ester LVIII. (5Z,7E,22E,24E)-(1S,3R)-(1,3-Dihydroxy-24a-homo-9,10-secochola-5,7,10(19),22,24-pentaen-24a-yl)phosphonic acid-monobutyl ester LIX. (5Z,7E,22E,24E)-(1S,3R)-(1,3-Dihydroxy-24a-homo-9,10-secochola-5,7,10(19),22,24-pentaen-24a-yl)phosphonic acid LX. (5Z,7E,22E)-(1S,3R,24ξ)-(1,3-Dihydroxy-24a-homo-9,10-secochola-5,7,10(19),22-tetraene-24,24a-diyl)bis[phosphonic acid dimethyl ester]

LXI. (5Z,7E,22E)-(1S,3R,24ξ)-(1,3-Dihydroxy-24a-homo-9,10-secochola-5,7,10(19),22-tetraene-24,24a-diyl)bis[phosphonic acid diethyl ester]

LXII. (5Z,7E,22E)-(1S,3R,24ξ)-(1,3-Dihydroxy-24a-homo-9,10-secochola-5,7,10(19),22-tetraene-24,24a-diyl)bis[phosphonic acid-bis(1-methylethyl)ester]

LXIII. (5Z,7E,22E)-(1S,3R,24ξ)-(1,3-Dihydroxy-24a-homo-9,10-secochola-5,7,10(19),22-tetraene-24,24a-diyl)bis[phosphonic acid dipropyl ester]

LXIV. (5Z,7E,22E)-(1S,3R,24ξ)-(1,3-Dihydroxy-24a-homo-9,10-secochola-5,7,10(19),22-tetraene-24,24a-diyl)bis[phosphonic acid dibutyl ester]

LXV. (5Z,7E,22E)-(1S,3R)-(1,3-Dihydroxy-24-nor-9,10-secocholesta-5,7,10(19),22-tetraene-26,27-diyl)bis[phosphonic acid dimethyl ester]

LXVI. (5Z,7E,22E)-(1S,3R)-(1,3-Dihydroxy-24-nor-9,10-secocholesta-5,7,10(19),22-tetraene-26,27-diyl)bis[phosphonic acid diethyl ester]

LXVII. (5Z,7E,22E)-(1S,3R)-(1,3-Dihydroxy-24-nor-9,10-secocholesta-5,7,10(19),22-tetraene-26,27-diyl)bis[phosphonic acid-bis(1-methylethyl)ester]

LXVIII. (5Z,7E,22E)-(1S,3R)-(1,3-Dihydroxy-24-nor-9,10-secocholesta-5,7,10(19),22-tetraene-26,27-diyl)bis[phosphonic acid dipropyl ester]

LXIX. (5Z,7E,22E)-(1S,3R)-(1,3-Dihydroxy-24-nor-9,10-secocholesta-5,7,10(19),22-tetraene-26,27-diyl]bis[phosphonic acid dibutyl ester]

LXX. (5Z,7E,22E)-(1S,3R)-(1,3-Dihydroxy-24-nor-9,10-secocholesta-5,7,10(19),22-tetraene-26,27-diyl)bis[phosphonic acid]

LXXI. (5Z,7E,22E,24E)-(1S,3R)-(1,3-Dihydroxy-24a-homo-9,10-secochola-5,7,10(19),22-pentaene-24a,24a-diyl)bis[phosphonic acid dimethyl ester]

LXXII. (5Z,7E,22E,24E)-(1S,3R)-(1,3-Dihydroxy-24a-homo-9,10-secochola-5,7,10(19),22-pentaene-24a,24a-diyl)bis[phosphonic acid diethyl ester]

LXXIII. (5Z,7E,22E,24E)-(1S,3R)-(1,3-Dihydroxy-24a-homo-9,10-secochola-5,7,10(19),22-pentaene-24a,24a-diyl)bis[phosphonic acid-bis(1-methylethyl)ester]

LXXIV. (5Z,7E,22E,24E)-(1S,3R)-(1,3-Dihydroxy-24a-homo-9,10-secochola-5,7,10(19),22-pentaene-24a,24a-diyl)bis[phosphonic acid dipropyl ester]

LXXV. (5Z,7E,22E,24E)-(1S,3R)-(1,3-Dihydroxy-24a-homo-9,10-secochola-5,7,10(19),22-pentaene-24a,24a-diyl)bis[phosphonic acid dibutyl ester]

LXXVI. (5Z,7E,22E,24E)-(1S,3R)-(1,3-Dihydroxy-24a-homo-9,10-secochola-5,7,10(19),22-pentaene-24a,24a-diyl)bis[phosphonic acid]

LXXVII. (5Z,7E,22E,24Z)-(1S,3R)-(24a-Chloro-1,3-dihydroxy-24a-homo-9,10-secochola-5,7,10(19),22,24-pentaen-24-yl)phosphonic acid dimethyl ester LXXVIII. (5Z,7E,22E,24Z)-(1S,3R)-(24a-Chloro-1,3-dihydroxy-24a-homo-9,10-secochola-5,7,10(19),22,24-pentaen-24-yl)phosphonic acid diethyl ester LXXIX. (5Z,7E,22E,24Z)-(1S,3R)-(24a-Chloro-1,3-dihydroxy-24a-homo-9,10-secochola-5,7,10(19),22,24-pentaen-24-yl)phosphonic acid-bis(1-methylethyl)ester LXXX. (5Z,7E,22E,24Z)-(1S,3R)-(24a-Chloro-1,3-dihydroxy-24a-homo-9,10-secochola-5,7,10(19),22,24-pentaen-24-yl)phosphonic acid dipropyl ester LXXXI. (5Z,7E,22E,24Z)-(1S,3R)-(24a-Chloro-1,3-dihydroxy-24a-homo-9,10-secochola-5,7,10(19),22,24-pentaen-24-yl)phosphonic acid dibutyl ester LXXXII. (5Z,7E,22E,24Z)-(1S,3R)-(24a-Chloro-1,3-dihydroxy-24a-homo-9,10-secochola-5,7,10(19),22,24-pentaen-24-yl)phosphonic acid LXXXIII. (5Z,7E,22E)-(1S,3R)-(1,3-Dihydroxy-24a-homo-9,10-secochola-5,7,10(19),22-tetraen-24-in-24a-yl) phosphonic acid dimethyl ester LXXXIV. (5Z,7E,22E)-(1S,3R)-(1,3-Dihydroxy-24a-homo-9,10-secochola-5,7,10(19),22-tetraen-24-in-24a-yl) phosphonic acid diethyl ester LXXXV. (5Z,7E,22E)-(1S,3R)-(1,3-Dihydroxy-24a-homo-9,10-secochola-5,7,10(19),22-tetraen-24-in-24a-yl) phosphonic acid-bis(1-methylethyl)ester LXXXVI. (5Z,7E,22E)-(1S,3R)-(1,3-Dihydroxy-24a-homo-9,10-secochola-5,7,10(19),22-tetraen-24-in-24a-yl)phosphonic acid dipropyl ester LXXXVII. (5Z,7E,22E)-(1S,3R)-(1,3-Dihydroxy-24a-homo-9,10-secochola-5,7,10(19),22-tetraen-24-in-24a-yl)phosphonic acid dibutyl ester LXXXVIII. (5Z,7E,22E)-(1S,3R)-(1,3-Dihydroxy-24a-homo-9,10-secochola-5,7,10(19),22-tetraen-24-in-24a-yl)phosphonic acid-monomethyl ester LXXXIX. (5Z,7E,22E)-(1S,3R)-(1,3-Dihydroxy-24a-homo-9,10-secochola-5,7,10(19),22-tetraen-24-in-24a-yl)-phosphonic acid-monoethyl ester XC. (5Z,7E,22E)-(1S,3R)-(1,3-Dihydroxy-24a-homo-9,10-secochola-5,7,10(19),22-tetraen-24-in-24a-yl) phosphonic acid-mono-(1-methylethyl)ester XCI. (5Z,7E,22E)-(1S,3R)-(1,3-Dihydroxy-24a-homo-9,10-secochola-5,7,10(19),22-tetraen-24-in-24a-yl) phosphonic acid-monopropyl ester XCII. (5Z,7E,22E)-(1S,3R)-(1,3-Dihydroxy-24a-homo-9,10-secochola-5,7,10(19),22-tetraen-24-in-24a-yl) phosphonic acid-monobutyl ester XCIII. (5Z,7E,22E)-(1S,3R)-(1,3-Dihydroxy-24a-homo-9,10-secochola-5,7,10(19),22-tetraen-24-in-24a-yl) phosphonic acid XCIV. (5Z,7E,22E)-(1S,3R,24S)-(24a,24a-Dichloro-1,3,24-trihydroxy-24a-homo-9,10-secochola-5,7,10(19),22-tetraen-24a-yl)phosphonic acid dimethyl ester XCV. (5Z,7E,22E)-(1S,3R,24R)-(24a,24a-Dichloro-1,3,24-trihydroxy-24a-homo-9,10-secochola-5,7,10(19),22-tetraen-24a-yl)phosphonic acid dimethyl ester XCVI. (5Z,7E,22E)-(1S,3R,24S)-(24a,24a-Dichloro-1,3,24-trihydroxy-24a-homo-9,10-secochola-5,7,10(19),22-tetraen-24a-yl)phosphonic acid diethyl ester XCVII. (5Z,7E,22E)-(1S,3R,24R)-(24a,24a-Dichloro-1,3,24-trihydroxy-24a-homo-9,10-secochola-5,7,10(19),22-tetraen-24a-yl)phosphonic acid diethyl ester XCVIII. (5Z,7E,22E)-(1S,3R,24S)-24a,24a-Dichloro-1,3,24-trihydroxy-24a-homo-9,10-secochola-5,7,10(19),22-tetraen-24a-yl)phosphonic acid-bis(1-methylethyl)ester XCIX. (5Z,7E,22E)-(1S,3R,24R)-(24a,24a-Dichloro-1,3,24-trihydroxy-24a-homo-9,10-secochola-5,7,10(19),22-tetraen-24a-yl)phosphonic acid-bis(1-methylethyl)ester C. (5Z,7E,22E)-(1S,3R,24S)-(24a,24a-Dichloro-1,3,24-trihydroxy-24a-homo-9,10-secochola-5,7,10(19),22-tetraen-24a-yl)phosphonic acid dipropyl ester CI. (5Z,7E,22E)-(1S,3R,24R)-(24a,24a-Dichloro-1,3,24-trihydroxy-24a-homo-9,10-secochola-5,7,10(19),22-tetraen-24a-yl)phosphonic acid dipropyl ester CII. (5Z,7E,22E)-(1S,3R,24S)-(24a,24a-Dichloro-1,3,24-trihydroxy-24a-homo-9,10-secochola-5,7,10(19),22-tetraen-24a-yl)phosphonic acid dibutyl ester CIII. (5Z,7E,22E)-(1S,3R,24R)-(24a,24a-Dichloro-1,3,24-trihydroxy-24a-homo-9,10-secochola-5,7,10(19),22-tetraen-24a-yl)phosphonic acid dibutyl ester CIV. (5Z,7E,22E)-(1S,3R,24S)-(24a,24a-Dichloro-1,3,24-trihydroxy-24a-homo-9,10-secochola-5,7,10(19),22-tetraen-24a-yl)phosphonic acid CV. (5Z,7E,22E)-(1S,3R,24R)-(24a,24a-Dichloro-1,3,24-trihydroxy-24a-homo-9,10-secochola-5,7,10(19),22-tetraen-24a-yl)phosphonic acid CVI. (5Z,7E,22E)-(1S,3R,24S)-(24a,24a-Difluoro-1,3,24-trihydroxy-24a-homo-9,10-secochola-5,7,10(19),22-tetraen-24a-yl)phosphonic acid dimethyl ester CVII. (5Z,7E,22E)-(1S,3R,24R)-(24a,24a-Difluoro-1,3,24-trihydroxy-24a-homo-9,10-secochola-5,7,10(19),22-tetraen-24a-yl)phosphonic acid dimethyl ester CVIII. (5Z,7E,22E)-(1S,3R,24S)-(24a,24a-Difluoro-1,3,24-trihydroxy-24a-homo-9,10-secochola-5,7,10(19),22-tetraen-24a-yl)phosphonic acid diethyl ester CIX. (5Z,7E,22E)-(1S,3R,24R)-(24a,24a-Difluoro-1,3,24-trihydroxy-24a-homo-9,10-secochola-5,7,10(19),22-tetraen-24a-yl)phosphonic acid diethyl ester CX. (5Z,7E,22E)-(1S,3R,24S)-(24a,24a-Difluoro-1,3,24-trihydroxy-24a-homo-9,10-secochola-5,7,10(19),22-tetraen-24a-yl)phosphonic acid-bis(1-methylethyl)ester CXI. (5Z,7E,22E)-(1S,3R,24R)-(24a,24a-Difluoro-1,3,24-trihydroxy-24a-homo-9,10-secochola-5,7,10(19),22-tetraen-24a-yl)phosphonic acid-bis(1-methylethyl)ester CXII. (5Z,7E,22E)-(1S,3R,24S)-(24a,24a-Difluoro-1,3,24-trihydroxy-24a-homo-9,10-secochola-5,7,10(19),22-tetraen-24a-yl)phosphonic acid dipropyl ester CXIII. (5Z,7E,22E)-(1S,3R,24R)-(24a,24a-Difluoro-1,3,24-trihydroxy-24a-homo-9,10-secochola-5,7,10(19),22-tetraen-24a-yl)phosphonic acid dipropyl ester CXIV. (5Z,7E,22E)-(1S, 3R,24S)-(24a,24a-Difluoro-1,3,24-trihydroxy-24a-homo-9,10-secochola-5,7,10(19),22-tetraen-24a-yl)phosphonic acid dibutyl ester CXV. (5Z,7E,22E)-(1S,3R,24R)-(24a,24a-Difluoro-1,3,24-trihydroxy-24a-homo-9,10-secochola-5,7,10(19),22-tetraen-24a-yl)phosphonic acid dibutyl ester CXVI. (5Z,7E,22E)-(1S,3R,24S)-(24a,24a-Difluoro-1,3,24-trihydroxy-24a-homo-9,10-secochola-5,7,10(19),22-tetraen-24a-yl)phosphonic acid CXVII. (5Z,7E,22E)-(1S,3R)-(24a,24a-Difluoro-1,3-dihydroxy-24-oxo-24a-homo-9,10-secochola-5,7,10(19),22-tetraen-24a-yl)phosphonic acid dimethyl ester CXVIII. (5Z,7E,22E)-(1S,3R)-(24a,24a-Difluoro-1,3-dihydroxy-24-oxo-24a-homo-9,10-secochola-5,7,10(19),22-tetraen-24a-yl)phosphonic acid diethyl ester CXIX. (5Z,7E,22E)-(1S,3R)-(24a,24a-Difluoro-1,3-dihydroxy-24-oxo-24a-homo-9,10-secochola-5,7,10(19),22-tetraen-24a-yl)phosphonic acid-bis(1-methylethyl)ester CXX. (5Z,7E,22E)-(1S,3R)-(24a,24a-Difluoro-1,3-dihydroxy-24-oxo-24a-homo-9,10-secochola-5,7,10(19),22-tetraen-24a-yl)phosphonic acid dipropyl ester CXXI. (5Z,7E,22E)-(1S,3R)-(24a,24a-Difluoro-1,3-dihydroxy-24-oxo-24a-homo-9,10-secochola-5,7,10(19),22-tetraen-24a-yl)phosphonic acid dibutyl ester CXXII. (5Z,7E,22E)-(1S,3R)-(24a,24a-Dichloro-1,3-dihydroxy-24-oxo-24a-homo-9,10-secochola-5,7,10(19),22-tetraen-24a-yl)phosphonic acid dimethyl ester CXXIII. (5Z,7E,22E)-(1S,3R)-(24a,24a-Dichloro-1,3-dihydroxy-24-oxo-24a-homo-9,10-secochola-5,7,10(19),22-tetraen-24a-yl)phosphonic acid diethyl ester CXXIV. (5Z,7E,22E)-(1S,3R)-(24a,24a-Dichloro-1,3-dihydroxy-24-oxo-24a-homo-9,10-secochola-5,7,10(19),22-tetraen-24a-yl)phosphonic acid-bis(1-methylethyl)ester CXXV. (5Z,7E,22E)-(1S,3R)-(24a,24a-Dichloro-1,3-dihydroxy-24-oxo-24a-homo-9,10-secochola-5,7,10(19),22-tetraen-24a-yl)phosphonic acid dipropyl ester CXXVI. (5Z,7E,22E)-(1S,3R)-(24a,24a-Dichloro-1,3-dihydroxy-24-oxo-24a-homo-9,10-secochola-5,7,10(19),22-tetraen-24a-yl)phosphonic acid dibutyl ester CXXVII. (5Z,7E,22E)-(1S,3R)-(26,27-Diethenyl-1,3-dihydroxy-24-oxo-9,10-secocholesta-5,7,10(19),22-tetraen-25-yl)phosphonic acid dimethyl ester CXXVIII. (5Z,7E,22E)-(1S,3R)-(26,27-Diethenyl-1,3-dihydroxy-24-oxo-9,10-secocholesta-5,7,10(19),22-tetraen-25-yl)phosphonic acid diethyl ester CXXIX. (5Z,7E,22E)-(1S,3R)-(26,27-Diethenyl-1,3-dihydroxy-24-oxo-9,10-secocholesta-5,7,10(19),22-tetraen-25-yl)phosphonic acid-bis(1-methylethyl)ester CXXX. (5Z,7E,22E)-(1S,3R)-(26,27-Diethenyl-1,3-dihydroxy-24-oxo-9,10-secocholesta-5,7,10(19),22-tetraen-25-yl)phosphonic acid propyl ester CXXXI. (5Z,7E,22E)-(1S,3R)-(26,27-Diethenyl-1,3-dihydroxy-24-oxo-9,10-secocholesta-5,7,10(19),22-tetraen-25-yl)phosphonic acid butyl ester CXXXII. (5Z,7E,22E)-(1S,3R)-(26,27-Diethenyl-1,3-dihydroxy-24-oxo-9,10-secocholesta-5,7,10(19),22-tetraen-25-yl)phosphonic acid CXXXIII. (5Z,7E,22E)-(1S,3R,24ξ)-(1,3-Dihydroxy-26-ethenyl-24-oxo-27-nor-9,10-secocholesta-5,7,10(19),22-tetraen-25-yl)phosphonic acid dimethyl ester CXXXIV. (5Z,7E,22E)-(1S,3R,24ξ)-(1,3-Dihydroxy-26-ethenyl-24-oxo-27-nor-9,10-secocholesta-5,7,10(19),22-tetraen-25-yl)phosphonic acid diethyl ester CXXXV. (5Z,7E,22E)-(1S,3R,24ξ)-(1,3-Dihydroxy-26-ethenyl-24-oxo-27-nor-9,10-secocholesta-5,7,10(19),22-tetraen-25-yl)phosphonic acid-bis(1-methylethyl)ester CXXXVI. (5Z,7E,22E)-(1S,3R,24ξ)-(1,3-Dihydroxy-26-ethenyl-24-oxo-27-nor-9,10-secocholesta-5,7,10(19),22-tetraen-25-yl)phosphonic acid dipropyl ester CXXXVII. (5Z,7E,22E)-(1S,3R,24ξ)-(1,3-Dihydroxy-26-ethenyl-24-oxo-27-nor-9,10-secocholesta-5,7,10(19),22-tetraen-25-yl)phosphonic acid dibutyl ester CXXXVIII. (5Z,7E,22E)-(1S,3R,24ξ)-(1,3-Dihydroxy-26-ethenyl-24-oxo-27-nor-9,10-secocholesta-5,7,10(19),22-tetraen-25-yl)phosphonic acid CXXXIX. (5Z,7E,22E)-(1S,3R)-(1,3-Dihydroxy-24-oxo-9,10-secocholesta-5,7,10(19),22-tetraen-25-yl)phosphonic acid dimethyl ester CXL. (5Z,7E,22E)-(1S,3R)-(1,3-Dihydroxy-24-oxo-9,10-secocholesta-5,7,10(19),22-tetraen-25-yl)phosphonic acid diethyl ester CXLI. (5Z,7E,22E)-(1S,3R)-(1,3-Dihydroxy-24-oxo-9,10-secocholesta-5,7,10(19),22-tetraen-25-yl)phosphonic acid-bis(1-methylethyl)ester CXLII. (5Z,7E,22E)-(1S,3R)-(1,3-Dihydroxy-24-oxo-9,10-secocholesta-5,7,10(19),22-tetraen-25-yl)phosphonic acid dipropyl ester CXLIII. (5Z,7E,22E)-(1S,3R)-(1,3-Dihydroxy-24-oxo-9,10-secocholesta-5,7,10(19),22-tetraen-25-yl)phosphonic acid dibutyl ester CXLIV. (5Z,7E,22E)-(1S,3R)-(1,3-Dihydroxy-24-oxo-9,10-secocholesta-5,7,10(19),22-tetraen-25-yl)phosphonic acid CXLV. (5Z,7E,22E)-(1S,3R)-(1,3-Dihydroxy-26,27-dimethyl-24-oxo-9,10-secocholesta-5,7,10(19),22-tetraen-25-yl)phosphonic acid dimethyl ester CXLVI. (5Z,7E,22E)-(1S,3R)-(1,3-Dihydroxy-26,27-dimethyl-24-oxo-9,10-secocholesta-5,7,10(19),22-tetraen-25-yl)phosphonic acid diethyl ester CXLVII. (5Z,7E,22E)-(1S,3R)-(1,3-Dihydroxy-26,27-dimethyl-24-oxo-9,10-secocholesta-5,7,10(19),22-tetraen-25-yl)phosphonic acid-bis(1-methylethyl)ester CXLVIII. (5Z,7E,22E)-(1S,3R)-(1,3-Dihydroxy-26,27-dimethyl-24-oxo-9,10-secocholesta-5,7,10(19),22-tetraen-25-yl)phosphonic acid dipropyl ester CXLIX. (5Z,7E,22E)-(1S,3R)-(1,3-Dihydroxy-26,27-dimethyl-24-oxo-9,10-secocholesta-5,7,10(19),22-tetraen-25-yl)phosphonic acid dibutyl ester CL. (5Z,7E,22E)-(1S,3R)-(1,3-Dihydroxy-26,27-dimethyl-24-oxo-9,10-secocholesta-5,7,10(19),22-tetraen-25-yl)-phosphonic acid CLI. (5Z,7E,22E)-(1S,3R,25R)-(1,3-Dihydroxy-26-methyl-24-oxo-27-nor-9,10-secocholesta-5,7,10(19),22-tetraen-25-yl)phosphonic acid dimethyl ester CLII. (5Z,7E,22E)-(1S,3R,25S)-(1,3-Dihydroxy-26-methyl-24-oxo-27-nor-9,10-secocholesta-5,7,10(19),22-tetraen-25-yl)phosphonic acid dimethyl ester CLIII. (5Z,7E,22E)-(1S,3R,25R)-(1,3-Dihydroxy-26-methyl-24-oxo-27-nor-9,10-secocholesta-5,7,10(19),22-tetraen-25-yl)phosphonic acid diethyl ester CLIV. (5Z,7E,22E)-(1S,3R,25S)-(1,3-Dihydroxy-26-methyl-24-oxo-27-nor-9,10-secocholesta-5,7,10(19),22-tetraen-25-yl)phosphonic acid diethyl ester CLV. (5Z,7E,22E)-(1S,3R,25R)-(1,3-Dihydroxy-26-methyl-24-oxo-27-nor-9,10-secocholesta-5,7,10(19)22-tetraen-25-yl) phosphonic acid-bis (1-methylethyl)ester CLVI. (5Z,7E,22E)-(1S,3R,25S)-1,3-Dihydroxy-26-methyl-24-oxo-27-nor-9,10-secocholesta-5,7,10(19),22-tetraen-25-yl)phosphonic acid-bis(1-methylethyl)ester CLVII. (5Z,7E,22E)-(1S,3R,25R)-(1,3-Dihydroxy-26-methyl-24-oxo-27-nor-9,10-secocholesta-5,7,10(19),22-tetraen-25-yl)phosphonic acid dipropyl ester CLVIII. (5Z,7E,22E)-(1S,3R,25S)-(1,3-Dihydroxy-26-methyl-24-oxo-27-nor-9,10-secocholesta-5,7,10(19),22-tetraen-25-yl)phosphonic acid dipropyl ester CLIX. (5Z,7E,22E)-(1S,3R,25R)-(1,3-Dihydroxy-26-methyl-24-oxo-27-nor-9,10-secocholesta-5,7,10(19),22-tetraen-25-yl)phosphonic acid dibutyl ester CLX. (5Z,7E,22E)-(1S,3R,25S)-(1,3-Dihydroxy-26-methyl-24-oxo-27-nor-9,10-secocholesta-5,7,10(19),22-tetraen-25-yl)phosphonic acid dibutyl ester CLXI. (5Z,7E,22E)-(1S,3R,25R)-(1,3-Dihydroxy-26-methyl-24-oxo-27-nor-9,10-secocholesta-5,7,10(19),22-tetraen-25-yl)phosphonic acid CLXII. (5Z,7E,22E)-(1S,3R,25S)-(1,3-Dihydroxy-26-methyl-24-oxo-27-nor-9,10-secocholesta-5,7,10(19),22-tetraen-25-yl)phosphonic acid CLXIII. (5Z,7E,22E)-(1S,3R,24S)-(1,3,24-Trihydroxy-9,10-secochola-5,7,10(19),22-tetraen-24-yl)phosphonic acid dimethyl ester CLXIV. (5Z,7E,22E)-(1S,3R,24R)-(1,3,24-Trihydroxy-9,10-secochola-5,7,10(19),22-tetraen-24-yl)phosphonic acid dimethyl ester CLXV. (5Z,7E,22E)-(1S,3R,24S)-(1,3,24-Trihydroxy-9,10-secochola-5,7,10(19),22-tetraen-24-yl)phosphonic acid diethyl ester CLXVI. (5Z, 7E ,22 E)-(1S,3R,24R)-(1,3,24-Trihydroxy-9,10-secochola-5,7,10(19),22-tetraen-24-yl)phosphonic acid diethyl ester CLXVII. (5Z,7E,22E)-(1S,3R,24S)-(1,3,24-Trihydroxy-9,10-secochola-5,7,10(19),22-tetraen-24-yl)phosphonic acid-bis(1-methylethyl)ester CLXVIII. (5Z,7E,22E)-(1S,3R,24R)-(1,3,24-Trihydroxy-9,10-secochola-5,7,10(19),22-tetraen-24-yl)phosphonic acid-bis(1-methylethyl)ester CLXIX. (5Z,7E,22E)-(1S,3R,24S)-(1,3,24-Trihydroxy-9,10-secochola-5,7,10(19),22-tetraen-24-yl)phosphonic acid dipropyl ester CLXX. (5Z,7E,22E)-(1S,3R,24R)-(1,3,24-Trihydroxy-9,10-secochola-5,7,10(19),22-tetraen-24-yl)phosphonic acid dipropyl ester CLXXI. (5Z,7E,22E)-(1S,3R,24S)-(1,3,24-Trihydroxy-9,10-secochola-5,7,10(19),22-tetraen-24-yl)phosphonic acid dibutyl ester CLXXII. (5Z,7E,22E)-(1S,3R,24R)-(1,3,24-Trihydroxy-9,10-secochola-5,7,10(19),22-tetraen-24-yl)phosphonic acid dibutyl ester CLXXIII. (5Z,7E,22E)-(1S,3R,24S)-(1,3,24-Trihydroxy-9,10-secochola-5,7,10(19),22-tetraen-24-yl)phosphonic acid CLXXIV. (5Z,7E,22E)-(1S,3R,24R)-(1,3,24-Trihydroxy-9,10-secochola-5,7,10(19),22-tetraen-24-yl)phosphonic acid
CLXXV. (5Z,7E,22E)-(1S,3R)(1,3-Dihydroxy-24-oxo-9,10-secochola-5,7,10(19),22-tetraen-24-yl)phosphonic acid dimethyl ester
CLXXVI. (5Z,7E,22E)-(1S,3R)-(1,3-Dihydroxy-24-oxo-9,10-secochola-5,7,10(19),22-tetraen-24-yl)phosphonic acid diethyl ester
CLXXVII. (5Z,7E,22E)-(1S,3R)-(1,3-Dihydroxy-24-oxo-9,10-secochola-5,7,10(19),22-tetraen-24-yl)phosphonic acid-bis(1-methylethyl)ester
CLXXVIII. (5Z,7E,22E)-(1S,3R)-(1,3-Dihydroxy-24-oxo-9,10-secochola-5,7,10(19),22-tetraen-24-yl)phosphonic acid propyl ester
CLXXIX. (5Z,7E,22E)-(1S,3R)-(1,3-Dihydroxy-24-oxo-9,10-secochola-5,7,10(19),22-tetraen-24-yl)phosphonic acid dibutyl ester
CLXXX. (5Z,7E,22E)-(1S,3R)-(1,3-Dihydroxy-24-oxo-9,10-secochola-5,7,10(19),22-tetraen-24-yl)phosphonic acid
CLXXXI. (5Z,7E,22E)-(1S,3S)-(1,3-Dihydroxy-24-oxo-24a-homo-9,10-secochola-5,7,10(19),22-tetraen-24a-yl)phosphonic acid dimethyl ester
CLXXXII. (5Z,7E,22E)-(1S,3S)-(1,3-Dihydroxy-24-oxo-24a-homo-9,10-secochola-5,7,10(19),22-tetraen-24a-yl)phosphonic acid diethyl ester
CLXXXIII. (5Z,7E,22E)-(1S,3S)-(1,3-Dihydroxy-24-oxo-24a-homo-9,10-secochola-5,7,10(19),22-tetraen-24a-yl)phosphonic acid-bis(1-methylethyl)ester
CLXXXIV. (5Z,7E,22E)-(1S,3S)-(1,3-Dihydroxy-24-oxo-24a-homo-9,10-secochola-5,7,10(19),22-tetraen-24a-yl)phosphonic acid dipropyl ester
CLXXXV. (5Z,7E,22E)-(1S,3S)-(1,3-Dihydroxy-24-oxo-24a-homo-9,10-secochola-5,7,10(19),22-tetraen-24a-yl)phosphonic acid dibutyl ester
CLXXXVI. (5Z,7E,22E)-(1S,3S)-(1,3-Dihydroxy-24-oxo-24a-homo-9,10-secochola-5,7,10(19),22-tetraen-24a-yl)phosphonic acid.

Of special importance within the scope of this invention are the compounds of general formula I' that are mentioned in the priority document (DE 19758119),

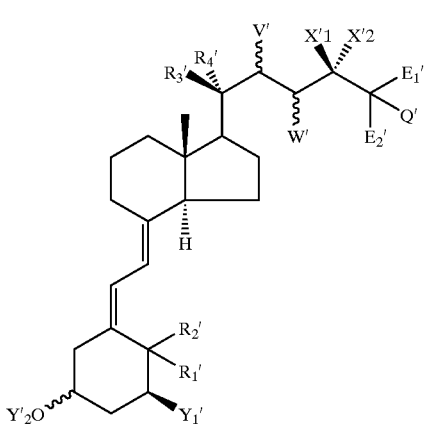

(I')

in which
$Y'_1$ means a hydrogen atom, a hydroxyl group, a fluorine, chlorine or bromine atom or a group —O(CO)$R'_5$, in which $R'_5$ is an aliphatic or aromatic radical with 1 to 12 C atoms,
$Y'_2$ means a hydrogen atom or a group —(CO)$R'_6$, in which $R'_6$ is an aliphatic or aromatic radical with 1 to 12 C atoms, and group $Y'_2$ O can be present both in the naturally occurring situation (3β) and in the epimeric situation (3α),
$R'_1$ and $R'_2$ each mean a hydrogen atom or together an exocyclic methylene group,
$R'_3$ and $R'_4$ independently of one another, mean a hydrogen atom, a chlorine or fluorine atom, an alkyl group with 1 to 4 carbon atoms, together a methylene group or together with quaternary carbon atom 20 a 3- to 7-membered, saturated or unsaturated carbocyclic ring,
V' and W' together mean an E-double bond or V' means a hydroxyl group and W' means a hydrogen atom or V' and W' in each case mean hydrogen atoms,
$X'_1$ and $X'_2$ together mean a carbonyl group or each mean a hydrogen atom or $X'_2$ means a hydrogen atom and $X'_1$ means a hydroxyl group or a group —O(CO)$R'_7$, in which
$R'_7$ is an aliphatic or aromatic radical with 1 to 12 C atoms, or $X'_1$ means a hydrogen atom and $X'_2$ means a hydroxyl group or a group O(CO)$R'_8$, in which
$R'_8$ is an aliphatic or aromatic radical with 1 to 12 C atoms,
or
$X'_1$ and $E'_2$ mean a double bond and at the same time $X'_2$ means a hydrogen atom or a group O—Z',
whereby Z' is an aliphatic or aromatic radical with 1 to 12 C atoms, an aliphatic or aromatic acyl group with 1 to 12 C atoms or a group $E'_2$,
$E'_1$ means a group PO(OR'$_9$)$_2$, a group PO(N(R'$_9$)$_2$)$_2$, a group PO(R'$_9$)$_2$, or a group CO$_2$R'$_9$, in which
$R'_9$ is a hydrogen atom or an aliphatic or aromatic radical with 1 to 12 C atoms,
$E'_2$ means a group PO(OR'$_9$)$_2$, a group PO(N(R'$_9$)$_2$)$_2$, a group PO(R'$_9$)$_2$, a group CO$_2$R'$_9$ or a hydrogen atom,
Q' means a hydrogen atom, an aliphatic or aromatic radical with 1 to 12 C atoms or a hydroxyl group, a group —O(CO)R'$_{10}$, a fluorine, chlorine, or bromine atom, an amino group or a group NHR'$_{10}$, or N(R'$_{10}$)$_2$, in which
$R'_{10}$ is an aliphatic or aromatic radical with 1 to 12 C atoms.

The substances according to the invention have a considerably higher metabolic stability than the structurally related compounds of the prior art and are therefore suitable in a special way for systemic administrations.

Relative to the structurally related compounds of the prior art, some of the substances according to the invention are also characterized in that they show a stronger effect on cell differentiation, whereby the action on the calcium balance does not increase.

Surprisingly enough, it was found for some of the substances according to the invention that they specifically require the creation of new bone material without simultaneously producing an increase in the serum calcium level.

Others of the substances according to the invention, however, exhibit an antagonistic or partial agonistic profile of action, which makes possible new uses.

Determination of Biological Activity

The vitamin D activity of the substances according to the invention is determined with the aid of the calcitriol-receptor test. It is carried out using a protein extract from the intestines of juvenile pigs. Receptor-containing protein extract is incubated in a test tube with $^3$H-calcitriol (5×10$^{-10}$ mol/l) in a reaction volume of 0.27 ml in the absence and in the presence of test substances for two hours at 4° C. To separate free and receptor-bonded calcitriol, a charcoal-dextran absorption is carried out. 250 μl of a charcoal-dextran suspension is fed to each test tube and incubated at 4° C. for 20 minutes. Then, the samples are centrifuged at 10,000 g for 5 minutes at 4° C. The supernatant is decanted and measured in a β-counter after 1 hour of equilibration in Picofluor 15™.

The competition curves that are obtained at various concentrations of test substance as well as of reference substance (unlabeled calcitriol) at constant concentration of the reference substance ($^3$H-calcitriol) are placed in relation to one another, and a competition factor (KF) is determined.

It is defined as a quotient of the concentrations of the respective test substance and the reference substance, which are necessary for 50% competition:

KF=Concentration of test substance at 50% competition/Concentration of reference substance at 50% competition To determine the acute hypercalcemic action of various calcitriol derivatives, the test that is described below is carried out:

The action of control (solution base), reference substance (1,25-dihydroxy vitamin $D_3$=calcitriol) and test substance is tested in each case after one-time subcutaneous administration in groups of 10 healthy male rats (140–170 g). During the testing time, the rats are kept in special cages to determine the excretion of water and mineral substances. Urine is collected in two fractions (0–16 hours and 16–22 hours). An oral dose of calcium (0.1 mmol of calcium in 6.5% alpha-hydroxypropyl-cellulose, 5 ml/animal) replaces at 1600 hours the calcium intake that is lacking by food deprivation. At the end of the test, the animals are killed by decapitation and exsanguinated to determine the serum-calcium values. For the primary screen test in vivo, an individual standard dose (200 μg/kg) is tested. For selected substances, the result is supported by establishing a dose-effect relation.

A hypercalcemic action is shown in serum-calcium level values that are higher than in the control.

The significance of differences between substance groups and controls and between test substance and reference substance are supported with suitable statistical processes. The result is indicated as dose ratio DR (DR=factor of test substance dose/reference substance dose for comparable actions).

The differentiation-stimulating action of calcitriol analogues is also detected quantitatively.

It is known in the literature [Mangelsdorf, D. J. et al., J. Cell. Biol. 98: 391 (1984)] that the treatment of human leukemia cells (promyelocyte cell line HL 60) in vitro with calcitriol induces the differentiation of cells to macrophages.

HL 60 cells are cultivated in tissue culture medium (RPMI 10% fetal calf serum) at 37° C. in an atmosphere of 5% $CO_2$ in air.

For substance testing, the cells are centrifuged off, and $2.0 \times 10^5$ cells/ml in phenol red-free tissue culture medium is taken up. The test substances are dissolved in ethanol and diluted with tissue culture medium without phenol red to the desired concentration. The dilution stages are mixed with the cell suspension at a ratio of 1:10, and 100 μl each of this cell suspension that is mixed with substance is pipetted into an indentation of a 96-hole plate. For control, a cell suspension is mixed analogously with the solvent.

After incubation for 96 hours at 37° C. in 5% $CO_2$ in air, 100 μl of an NBT-TPA solution (nitro blue tetrazolium (NBT), final concentration in the batch of 1 mg/ml, tetradecanoyl phorbolmyristate-13-acetate (TPA), final concentration in the batch of $2 \times 10^{-7}$ mol/l) is pipetted into each indentation of the 96-hole plate in the cell suspension.

By incubation for 2 hours at 37° C. and 5% $CO_2$ in air, NBT is reduced to insoluble formazan because of the intracellular oxygen radical release, stimulated by TPA, in the cells that are differentiated to macrophages.

To complete the reaction, the indentations of the 96-hole plate are suctioned off, and the cells are affixed to the bottom of the plate by adding methanol and dried after affixing. To dissolve the intracellular formazan crystals that are formed, 100 μl of potassium hydroxide (2 mol/l) and 100 μl of dimethyl sulfoxide are pipetted into each indentation and ultrasonically treated for 1 minute. The concentration of formazan is measured by spectrophotometry at 650 nm.

As a yardstick for the differentiation induction of HL 60 cells to macrophages, the concentration of formed formazan applies. The result is indicated as a dose ratio (DR=factor of test substance dose/reference substance dose for comparable semi-maximum actions).

The results of the calcitriol-receptor test and the determination of the dose ratio of the differentiation induction of HL 60 cells and the dose ratio for hypercalcemia are summarized below:

Examples of test substances:

(5Z,7E,22E)-(1S,3R)-(1,3-Dihydroxy-24-oxo-24a-homo-9,10-secochola-5,7,10(19),22-tetraen-24a-yl)phosphonic acid dimethyl ester 5

(5Z, 7E, 22E)-(1S,3R)-(1,3-Dihydroxy-24-oxo-24a-homo-9,10-secochola-5,7,10(19),22-tetraen-24a-yl)phosphonic acid diethyl ester 9

(5Z,7E,22E)-(1S,3R)-(1,3-Dihydroxy-24-oxo-24a-homo-9,10-secochola-5,7,10(19),22-tetraen-24a-yl)phosphonic acid bis(1-methylethyl)ester 13

(5Z,7E,22E)-(1S,3R,24ξ)-(1,3-Dihydroxy-24a-homo-9,10-secochola-5,7,10(19),22-tetraene-24,24a-diyl)bis[phosphonic acid diethyl ester] 29

(5Z,7E,22E)-(1S,3R)-(1,3-Dihydroxy-24-oxo-9,10-secocholesta-5,7,10(19),22-tetraen-25-yl)phosphonic acid diethyl ester 53

(5Z,7E,22E)-(1S,3R)-(1,3-Dihydroxy-26,27-dimethyl-24-oxo-9,10-secocholesta-5,7,10(19),22-tetraen-25-yl) phosphonic acid diethyl ester 57

(5Z,7E,22E)-(1S,3R,24R)-(1,3,24-Trihydroxy-9,10-secochola-5,7,10(19),22-tetraen-24-yl)phosphonic acid-bis(1-methylethyl)-ester 65b Comparison Substance Calcitriol

|  | KF | DR(HL 60) | DR (Ca) |
|---|---|---|---|
| 5 | 10 | 22 | >>100 |
| 9 | 10 | 58 | >300 |
| 13 | 6 | 32 | >300 |
| 29 | 10 | 3 | >300 |
| 53 | 12 | 15 | >>300 |
| 57 | 16 | 9 | >>300 |
| 65b | 10 | 3 | >>300 |
| Calcitriol | 1 | 1 | 1 |

In addition to a considerable affinity to the vitamin D receptor, the compounds listed show a pronounced cell-differentiating activity.

The induction of a hypercalcemia is carried out, however, only at very much higher doses than in the case of calcitriol.

The creation of new bone material is induced even at a non-hypercalcemic dose.

By the reduced property of triggering a hypercalcemia as well as the high metabolic stability, the substances according to the invention are suitable in a special way for the production of pharmaceutical agents for the treatment of diseases that are characterized by hyperproliferation and deficient cell differentiation. Included in these are, for example, hyperproliferative diseases of the skin (psoriasis, pityriasis subia pilasis, acne, ichthyosis) and pruritus, as well as tumor diseases and precancerous stages (for example, tumors of the intestines, carcinomas of the breast, lung tumors, prostate carcinomas, leukemias, T-cell lymphomas, melanomas, Batazell Larzin, squamous carcinoma, actinic keratoses, cervix dysplasias, and metastasizing tumors of any type).

Also, for the treatment and prophylaxis of diseases that are characterized by a disequilibrium of the immune system, the substances according to the invention are suitable. These include eczemas and diseases of the atopic Formon series and inflammatory diseases (rheumatoid arthritis, respiratory tract diseases, e.g., asthma), as well as auto-immune diseases, such as, for example, multiple sclerosis, diabetes mellitus type I, myasthenia gravis, lupus erythematosus, scleroderma, bullous skin diseases (pemphigus, pemphigoid), further rejection reactions in the case of autologous, allogeneic or xenogeneic transplants, as well as AIDS. In all of these diseases, the new compounds of general formula I can be combined advantageously with other substances that have an immunosuppressive action, such as cyclosporin A, FK 506, rapamycin and anti-CD 4-antibodies.

The substances are also suitable for therapy of secondary hyperparathyroidism and renal osteodystrophia because of the property of calcitriols to drop the parathormone synthesis.

Owing to the presence of the vitamin D receptor in the insulin-producing cells of the pancreas, the substances are suitable by increasing the insulin secretion for the therapy of diabetes mellitus type II.

Further, it has been found, surprisingly enough, that by topical application of the compounds according to the invention on the skin of mice, rats and guinea pigs, an increased reddening of the skin and increase of the thickness of the epidermis can be induced. The increase in the reddening of the skin is determined based on the increase in the red value of the skin surface that can be quantified with a calorimeter. The red value is typically increased 1.5-fold after the substance (dose 0.003%) is administered three times at intervals of 24 hours. The increase in the thickness of the epidermis is quantified in the histological preparation. It is typically increased 2.5-fold. The number of proliferating epidermal cells (cells in the S-phase of the cell cycle) is determined by flow cytometry and is typically increased by a factor of 6.

These properties of the derivatives in the vitamin D series according to the invention can appear suitable for therapeutic use in the case of atrophic skin, as it occurs in natural skin aging because of increased, light exposure or medicinally-induced skin atrophy by treatment with glucocorticoids.

Moreover, wound healing can be accelerated by topical application with the new compounds.

In cell populations of the hair follicle, which contribute decisively to hair growth or to hair cycle regulation, it was possible to detect vitamin $D_3$ receptor proteins [Stumpf, W. E. et al., Cell Tissue Res. 238, 489 (1984); Milde, P. et al., J. Invest. Dermatol. 97, 230 (1991)]. In addition, in vitro findings on isolated hair follicle keratinocytes show a proliferation-inhibiting and differentiation-stimulating influence of 1,25-$(OH)_2D_3$.

From clinical observations, it is known that the vitamin $D_3$-resistant rickets often accompanies alopecia, which develops in early infancy. Experimental findings show that the vitamin $D_3$ bonding site of the VDR in this disease mutates, i.e., is defective [Kristjansson, K. et al., J. Clin. Invest. 92, 12 (1993)]. Keratinocytes, which were isolated from the hair follicles of these patients, do not react in vitro to the addition of 1,25-$(OH)_2D_3$ [Arase, S. et al., J. Dermatol. Science 2, 353 (1991)].

These findings indicate a decisive role for 1,25-$(OH)_2D_3$ in the regulation of hair growth.

These analogues are therefore especially suitable for the production of pharmaceutical agents for the treatment of diseases which accompany disrupted hair growth (androgenetic alopecia, alopecia areata/totalis, chemotherapy-induced alopecia) or for supporting physiological hair growth without causing the side-effects of calcitriol (especially hypercalcemia).

Senile and postmenopausal osteoporosis is characterized by an increased bone turnover with an overall negative balance. Owing to the bone shrinkage especially of trabecular bones, fractures result to an increased extent. Owing to the stimulating action of calcitriol, both in the number and the conduct of synthesis of cells forming new bones (osteoblasts), the substances according to the invention are suitable for therapy and prophylaxis of senile and postmenopausal osteoporosis (EP 0 634 173 A1), of steroid-induced osteoporosis as well as for accelerated healing of arthroplasties without causing the side-effects of calcitriol (especially hypercalcemia). For the therapy of various forms of osteoporosis, they can be combined advantageously with estradiol or other derivatives of estrogen.

Finally, it was possible to show that calcitriol increases the synthesis of a growth substance for nerve cells (nerve growth factor) [M. S. Saporito et al. Brain Res. 633, 189 (1994)]. The compounds according to the invention are therefore also suitable for treating degenerative diseases of the peripheral and central nervous system, such as Alzheimer's disease and amyotrophic lateral sclerosis.

In addition, it has been found that certain compounds of general formula I in HL 60 cells antagonize, surprisingly enough, the action of calcitriol (see also WO 94/07853, WO 97/00242).

Such compounds can be used for the therapy of hypercalcemias, such as, for example, in hypervitaminosis D or intoxication with calcitriol and calcitriol-like active substances, or in the case of increased extrarenal calcitriol synthesis in granulomatous diseases (sarcoidosis, tuberculosis). Also, paraneoplastic hypercalcemias (for example, in osteolytic metastases and tumors with increased synthesis of parathormone-related peptides) as well as in hypercalcemias in the case of hyperparathyroidism.

In addition, calcitriol antagonists can be used for birth control. In the reproductive tracts of female and male animals, the vitamin D receptor is expressed. It is known that the female and male fertility of vitamin-D-deficient animals is reduced. By short-term substitution of calcitriol, the reproductive output can be increased. Calcitriol antagonists are therefore able to influence female and male fertility.

Since calcitriol, under certain conditions, shows an immunosuppressive action, calcitriol receptor antagonists can also be used as immunostimulants, e.g., in the case of weak defenses against infections, AIDS.

Calcitriol is known to be able to modulate hair growth. Calcitriol antagonists can therefore be used therapeutically in the case of undesirable hair growth, e.g., in hirsutism.

Vitamin D has long been known to play a stimulating role in the formation of arteriosclerotic plaque. In such vascular lesions, a calcitriol-regulated protein, osteopontin, is found to be increased, to which a role in vascular sclerosis is attributed [R. Eisenstein et al. Arch. Path. 77, 27 (1964), L. A. Fitzpatrick et al., J. Clin. Invest. 94, 1597 (1994)]. Calcitriol antagonists are therefore suitable for therapy and prophylaxis of all types of arteriosclerosis.

Finally, calcitriol antagonists are suitable because of the property of calcitriol to increase unspecific immune reactions of monocytic cells, for therapy of inflammatory diseases, especially of a chronic nature, such as rheumatoid arthritis, Crohn's disease, ulcerative colitis, and granulomatous diseases such as sarcoidosis and other foreign-body reactions.

For all listed therapeutic applications, it is true that the compounds according to the invention are able to achieve a therapeutic action in the above-mentioned clinical pictures without causing the side-effects of calcitriol (especially hypercalcemia).

This invention thus relates to pharmaceutical preparations that contain at least one compound according to general formula I together with a pharmaceutically compatible vehicle.

The compounds can be formulated as solutions in pharmaceutically compatible solvents or as emulsions, suspensions or dispersions in suitable pharmaceutical solvents or vehicles or as pills, tablets or capsules, which contain solid vehicles in a way known in the art. For topical use, the compounds are advantageously formulated as creams or ointments or in a similar form of pharmaceutical agent that is suitable for topical use. Each such formulation can also contain other pharmaceutically compatible and nontoxic adjuvants, such as, e.g., stabilizers, antioxidants, binders, dyes, emulsifiers or flavoring additives. The compounds are advantageously administered by injection, intravenous infusion of suitable sterile solutions, as an aerosol via bronchial tubes and lungs, or as oral dosage via the alimentary tract or topically in the form of creams, ointments, lotions or suitable transdermal patches, as is described in EP-A0 387 077.

The daily dose is approximately 0.1 μg/patient/day–1000 μg/patient/day, preferably 1.0 μg/patient/day–500 μg/patient/day.

BRIEF DESCRIPTION OF THE DRAWING

FIG. 1/1 identifies the structure of certain Vitamin D derivative compounds.

Process for the Production of the Compounds According to the Invention

The production of the vitamin D derivatives of general formula I is carried out according to the invention from a compound of general formula II,

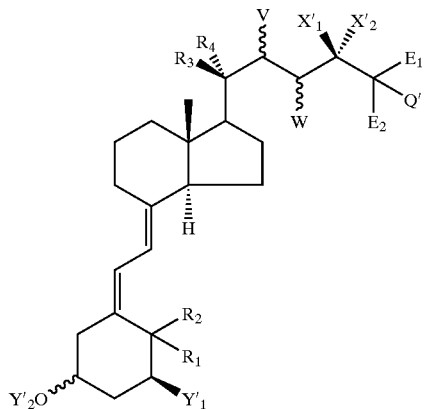

in which $Y'_1$ means a hydrogen atom, a halogen atom or a protected hydroxyl group, and $Y'_2$ means a hydroxy protective group.

$X'_1$, $X'_2$ and $Q'$ are distinguished from $X_1$, $X_2$ and $Q$ in that optionally present hydroxyl groups, amino groups or keto groups can be present in protected form.

The protective groups are preferably alkyl-, aryl- or mixed alkylaryl-substituted silyl groups, e.g., the trimethylsilyl (TMS), triethylsilyl (TES), tert-butyldimethylsilyl (TBDMS), tert-butyldiphenylsilyl (TBDPS) or triisopropylsilyl (TIPS) groups or another standard hydroxy protective group (methoxymethyl, methoxyethoxymethyl, ethoxyethyl, tetrahydrofuranyl and tetrahydropyranyl groups); for the keto groups, these are preferably ketals (1,3-dioxolans, 1,3-dioxanes, dialkoxyketals) (see T. W. Greene, P. G. M. Wuts "Protective Groups in Organic Synthesis," $2^{nd}$ Edition, John Wiley & Sons, 1991).

By simultaneous or successive cleavage of the hydroxy and keto protective groups and optionally by partial, successive or complete esterification of the free hydroxyl groups, II is converted into a compound of general formula I.

In the case of the silyl protective groups or the trimethylsilylethoxymethyl group, tetrabutylammonium fluoride, hydrofluoric acid or hydrofluoric acid/pyridine or acidic ion exchanger is used for their cleavage; in the case of ether groups (methoxymethyl, methoxyethoxymethyl, ethoxyethyl, tetrahydropyranyl ether) and ketals, the latter are cleaved off under catalytic action of acid, for example, p-toluenesulfonic acid, pyridinium-p-toluenesulfonate, acetic acid, hydrochloric acid, phosphonic acid or an acidic ion exchanger.

The cleavage of the phosphonic acid ester can be carried out according to commonly used processes by the action of acidic reagents (e.g., hydrochloric acid, acidic ion exchanger, trialkylsilyl halides).

The esterification of the free hydroxy groups can be carried out according to standard processes with the corresponding carboxylic acid chlorides, -bromides or -anhydrides.

The production of the starting compounds for general formula II starts from various starting compounds depending on the ultimately desired substitution pattern in 3-, 10- and 20-position.

For the production of compounds of general formula II, in which $R_1$ and $R_2$ together mean an exocyclic methylene group and $Y'_1$ means a hydrogen atom or a protected hydroxyl group and $Y'_2$ means a hydroxy protective group, and the natural stereochemistry is in 3-position, a start is made from known aldehyde III [M. Calverley Tetrahedron 43, 4609 (1987), WO 87/00834].

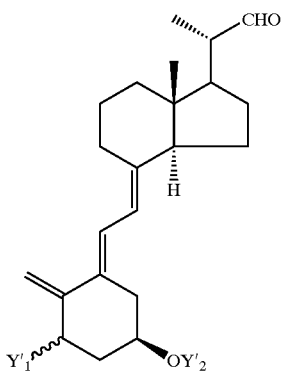

III

For Y'$_1$ and Y'$_2$, protective groups other than those mentioned in the bibliographic references can be obtained by analogous procedure using correspondingly modified silyl chlorides (e.g., tert-butyldiphenylsilyl chloride instead of tert-butyldimethylsilyl chloride). By foregoing the corresponding stages for 1α-hydroxylation, derivatives of Y'$_1$=H type can be obtained.

The compounds of general formula III are now converted, analogously to known processes, into aldehydes of general formula IV [EP 647 219, WO 94/07853, M. J. Calverley, L. Binderup Bioorg. Med. Chem. Lett. 3, 1845–1848 (1993)].

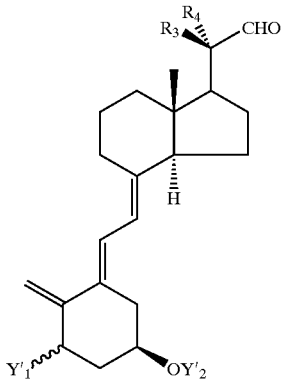

IV

For R$_3$ and R$_4$, the definitions that are already mentioned above apply.

To establish the natural vitamin D-triene system, a photochemical isomerization of the compounds of general formula IV is performed. Irradiation with ultraviolet light is carried out in the presence of a so-called triplet sensitizer. Within the scope of this invention, anthracene is used in this respect. By cleavage of the π-bond of the 5,6-double bond, rotation of the A ring by 180° around the 5,6-single bond and reestablishing the 5,6-double bond, the stereoisomerism on the 5,6-double bond is reversed, whereby compounds of general formula V accumulate,

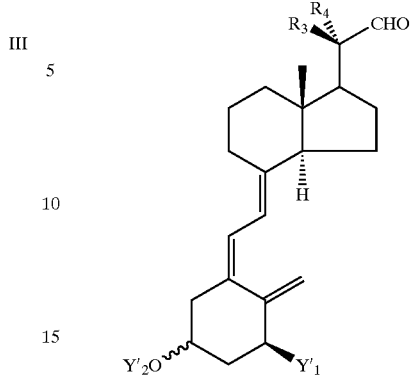

V

In principle, this isomerization reaction is also possible in a later stage. By way of example, the reactions of aldehyde VI with natural configuration at C-20 are described below.

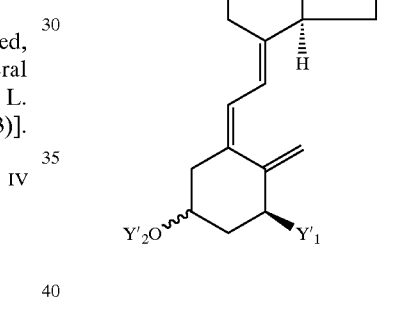

VI

In principle, however, the following reactions are also possible with the above-mentioned substitution models at C-20.

By reaction of the aldehyde of general formula VI with trialkylphosphonoacetates of general formula VII or amides of general formula VIII,

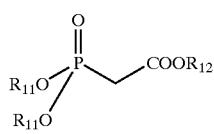

VII

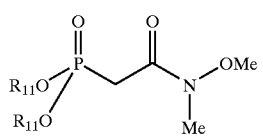

VIII whereby R$_{11}$ and R$_{12}$ mean aliphatic or aromatic radicals with 1 to 12 C atoms, esters of general formula IX or amides of general formula X are produced.

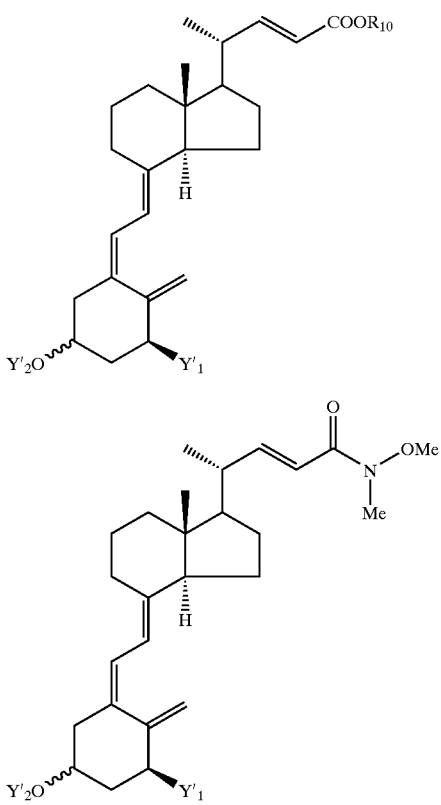

IX

X

The compounds of general formulas IX and X can now be reacted with phosphorus compounds of general formula XI that are deprotonated by a base, such as, for example, n-butyllithium, t-butyllithium, lithium diisopropylamide, sodium hydride, potassium hydride, sodium hydroxide, potassium hydroxide, sodium alcoholates, potassium alcoholates, etc.

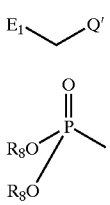

XI

XII $E_1$ and $Q'$ were already defined above. By way of example, the methylphosphonic acid ester of general formula XII represents a special case.

Thus, compounds of general formula II are obtained, for which it holds true that $X'_1$ and $X'_2$ together form a keto group. As previously described, these compounds can be converted into compounds of general formula I or can be converted with a reducing agent such as, for example, sodium borohydride, sodium borohydride/cerium trichloride (hetahydrate), diisobutyl aluminum hydride, lithium borohydride, etc., into compounds of general formula II, for which it holds true that $X'_1$ is a hydroxyl group and $X'_2$ is a hydrogen atom or $X'_1$ is a hydrogen atom and $X'_2$ is a hydroxyl group. The conversion into the compounds of general formula I is possible as described above.

As an alternative, the last compounds of general formula II can also be synthesized by reaction of the phosphorus compound of general formula XI with an aldehyde of general formula XIII, which can be obtained by reduction of the ester of general formula IX or the amide of general formula X with a reducing agent, such as, e.g., diisobutyl aluminum hydride, lithium aluminum hydride, etc.

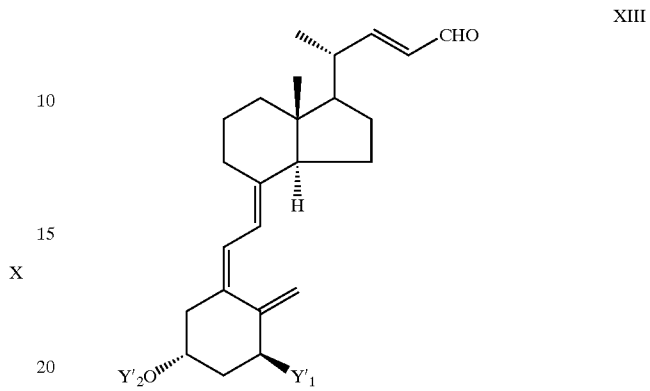

XIII

For synthesis of the compounds of general formula II, for which $X'_1$ and $X'_2$ are hydrogen atoms, derivatives of the alcohol of general formula XIV, which can be referred to with general formula XV, are used:

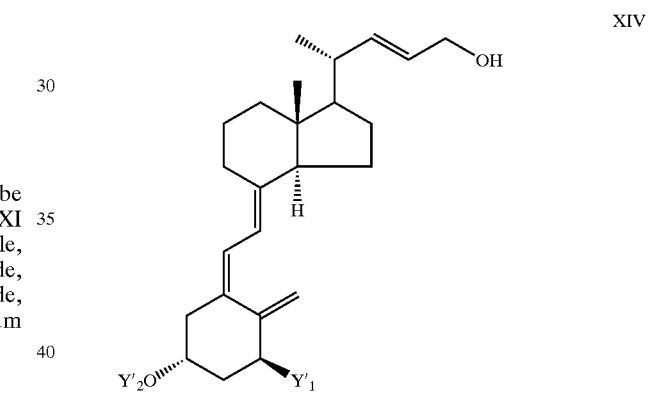

XIV

XV

The alcohol of general formula XIV can be obtained from the aldehyde of general formula XIII, the ester of general formula IX or an amide of general formula X with a reducing agent, such as, for example, diisobutyl aluminum hydride, lithium aluminum hydride, sodium borohydride, lithium borohydride, etc. Under commonly used conditions, the hydroxyl group must then be converted into a leaving group, such as, for example, a methanesulfonic acid ester, p-toluenesulfonic acid ester or a halogen atom (fluorine, chlorine, bromine). An isolation of this compound is not absolutely necessary. The reaction can now be carried out with a phosphorus compound of general formula XVI

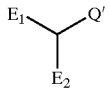

XVI that is deprotinated by a base, such as, for example, n-butyllithium, t-butyllithium, lithium diisopropylamide, sodium hydride, potassium hydride, sodium hydroxide, potassium hydroxide, sodium alcoholates, potassium alcoholates, etc., into compounds of general formula II, which is converted into a compound of general formula I as described. $E_1$, $E_2$ and Q' had already been defined.

The compound of general formula XVI can also under palladium catalysis with compounds of general formula XIV or general formula XV for which it holds true that L means acetate, carbonate or similar groups [see D. E. Bergbreiter et al., J. Chem. Soc., Chem. Comm. 883–884 (1989), J. Tsuji "Organic Synthesis with Palladium Compounds," Springer Verlag, Berlin, 1980], whereby compounds of general formula II of the above meaning are formed and can be converted into compounds of general formula I as described.

If, in general formula II, $X'_1$ and $X'_2$ together form a keto group and $E_1$ and $E_2$ simultaneously represent phosphorus-containing groups, the synthesis can also be carried out starting from the acid derivative of general formula XVII,

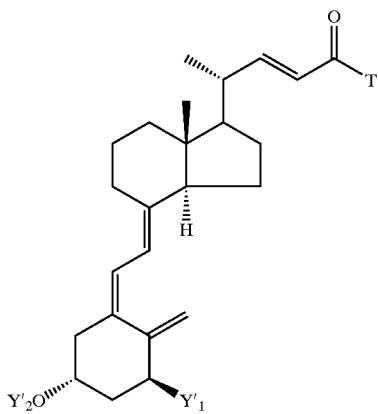

XVII whereby T means a halide, a cyanide group or an activating group (e.g., anhydride). The production of the compound of general formula XVII is possible after hydrolysis of the ester group of general formula IX and functionalization under the commonly used conditions.

The reaction can now be carried out with a phosphorus compound of general formula XVI that is deprotonated by a base, such as, for example, n-butyllithium, t-butyllithium, lithium diisopropylamide, sodium hydride, potassium hydride, sodium hydroxide, potassium hydroxide, sodium alcoholates, potassium alcoholates, etc., into compounds of general formula II, which are converted into compounds of general formula I as described.

The reaction of the aldehyde of general formula XIII with a compound of general formula XVI represents a special case, for which it holds true that $E_1$ and $E_2$ are the same. In this reaction, a compound of general formula XVIII

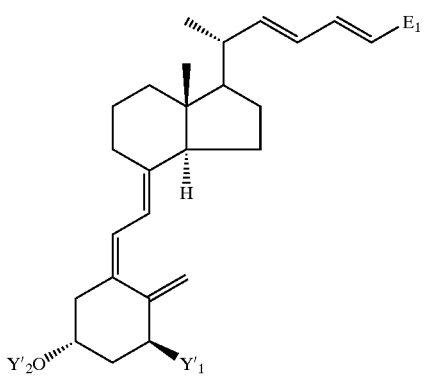

XVIII is generated by elimination of a phosphorus-containing group, which can be considered as a special case of general formula II, for which it holds true that $X'_1$ and $E_2$ together form an E-double bond and $X'_2$ and Q are hydrogen atoms. The further reaction to compounds of general formula I can be carried out as described.

The compound of general formula XVIII can also be reacted with nucleophilic reagents in Michael condensation, whereby compounds of general formula II accumulate, which are converted, as described, into compounds of general formula I with corresponding meanings for $X_1$ and $X_2$.

If, in general formula II, $X'_1$ and $E_2$ together form a double bond, and $X'_2$ means a group —OZ, a compound of general formula II, for which it holds true that $X'_1$ and $X'_2$ together form a keto group, $E_1$ has the described definition and $E_2$ means a hydrogen atom, is deprotonated with a base, such as, for example, n-butyllithium, t-butyllithium, lithium diisopropylamide, sodium hydride, potassium hydride, sodium hydroxide, potassium hydroxide, sodium alcoholates, potassium alcoholates and then reacted with a compound of general formula XIX,

L—Z     XIX whereby L is a leaving group of the above meaning, and Z was defined previously. Further reaction to compounds of general formula I can be carried out as described.

If $X'_1$ and $X'_2$ in general formula II together mean a carbonyl group, $E_1$ and $E_2$ have the above meanings, and Q' is not hydrogen, a compound of general formula II, for which it holds true that $X'_1$ and $X'_2$ mean a carbonyl group and $E_1$ and $E_2$ have the above meanings and Q' is a hydrogen, is deprotonated with a base, such as, for example, n-butyllithium, t-butyllithium, lithium diisopropylamide, sodium hydride, potassium hydride, sodium hydroxide, potassium hydroxide, sodium alcoholates, potassium alcoholates, and then reacted with a compound of general formula XX,

L—Q'     XX whereby L is a leaving group of the above meaning and Q was previously defined.

As an alternative, palladium-catalyzed linkage reactions can also be used. In this case, L must be a hydroxy group, an acetate, carbonate or a comparable group [see D. E. Bergbreiter et al. J. Chem. Soc., Chem. Comm. 883–884 (1989), J. Tsuji "Organic Synthesis with Palladium Compounds," Springer Verlag, Berlin, 1980].

The further reaction to compounds of general formula I can be carried out as described.

Compounds of general formula II, for which it holds true that V and W can mean hydrogen atoms, can be produced by reduction of the 22,23-double bond on ester IX, amide X or aldehyde XIII under the usual reduction conditions [sodium borohydride/pyridine; magnesium in methanol; copper hydride, generated in situ, M. F. Semmelhack et al. J. org. Chem. 40, 3619–3621 (1975); samarium iodide, H. Alper Tetrahedron Lett. 33, 5007–5008 (1992); sodium dithionite, K. G. Akamanchi et al. Synth. Comm. 22, 1655–1660 (1992) etc.] and further reactions (as described).

In addition, the alcohol of general formula XXI as well as derivatives of general formula XXII can be synthesized by additional reduction and reacted as described.

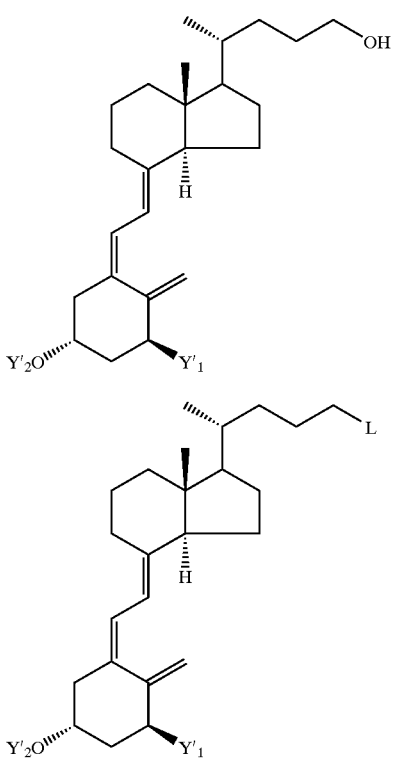

XXI

XXII

For synthesis of compounds of general formula II for which $R_1$ and $R_2$ are hydrogen atoms, a convergent synthesis method must be employed, in which CD- and A-ring fragments are synthesized separately. For synthesis of the CD-fragments, aldehyde XXIII that is known in the literature [H. H. Inhoffen et al. Chem. Ber. 92, 781–791 (1958); H. H. Inhoffen et al. Chem. Ber. 92, 1772–1788 (1959); W. G. Dauben et al., Tetrahedron Lett. 30, 677–680 (1989)] is used,

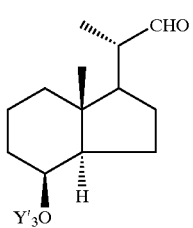

XXIII in which $Y'_3$ means an acyl-, alkyl- or aryl-substituted silyl group, or a tetrahydropyranyl, tetrahydrofuranyl, methoxymethyl or ethoxyethyl group, an acyl group (e.g., acetyl or benzoyl group) or another hydroxy protective group (see T. W. Greene, P. G. M. Wuts Protective Groups in organic Synthesis, $2^{nd}$ Edition, John Wiley and Sons, Inc. 1991).

According to the known processes, the already described modifications at C-20 can be introduced here (WO 94/07853), whereby a compound of general formula XXIV accumulates.

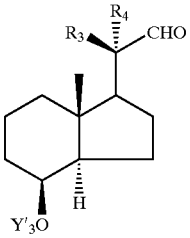

XXIV

The introduction of the side chains is carried out here analogously to the case of vitamin D-aldehyde VI, whereby compounds of general formula XXV are obtained.

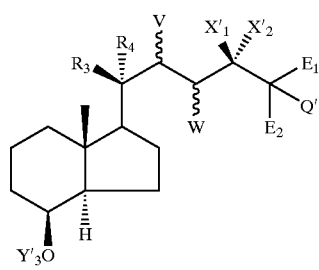

XXV

The variables were already defined previously.

In the selection of suitable protective groups (e.g., $Y'_3$= triethylsilyl), $Y'_3$ is selectively cleaved off (e.g., with tetrabutylammonium fluoride), whereby the compound of general formula XXVI accumulates.

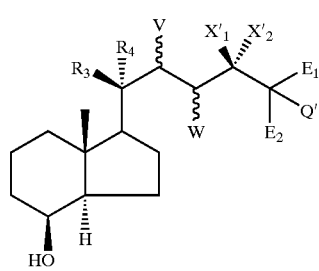

XXVI

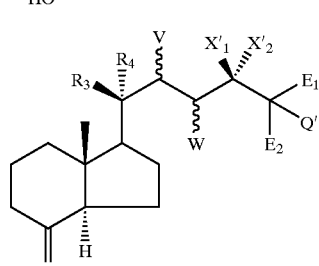

XXVII

XXVIII

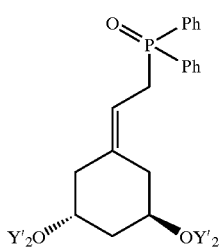

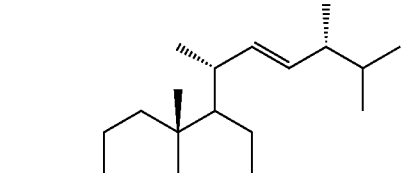

Oxidation according to known methods (e.g., pyridinium chlorochromate, pyridinium dichromate, Swern conditions, etc.) produces a compound of general formula XXVII, which by reaction with the anion, produced by a base (e.g., lithium diisopropylamide, n-butyllithium), of the phosphine oxide of general formula XXVIII known in the literature [H. F. DeLuca et al. Tetrahedron Lett. 32, 7663–7666 (1991)], in which Y'$_2$ has the already described meaning, is converted into corresponding compounds of general formula II for which the following is true: Y'$_1$=OY'$_2$. Further reaction to form the compound of general formula I is carried out as already described.

For the synthesis of compounds of general formula II for which group Y$_2$O is in 3α-position, an epimerization must be performed in an early stage. This is shown with compound XXIX as an example. The process is basically possible with other side chain structures, however.

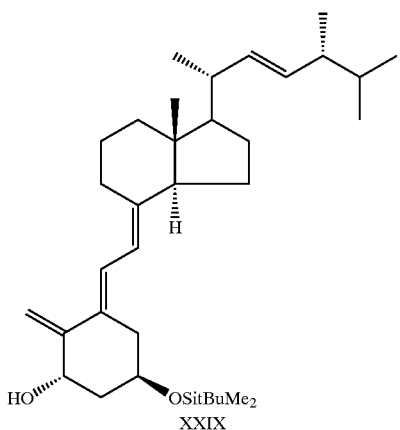
XXIX

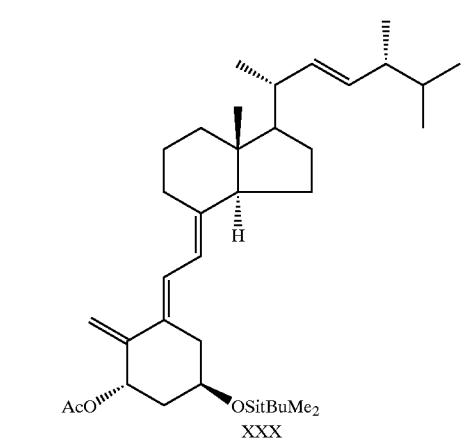
XXX

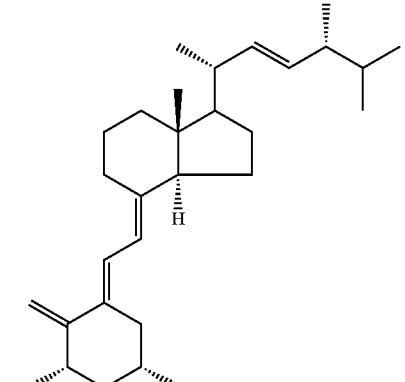
XXXI

XXXII

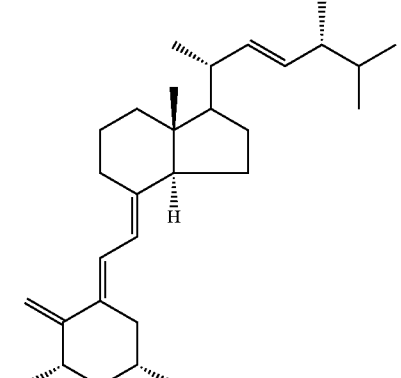
XXXIII

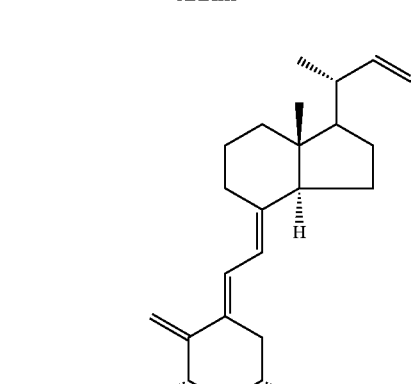
XXXIV

The above-indicated protective group strategy represents only one example of the production of the 3-epi derivative. Various other strategies are basically possible. By acetylation of the free hydroxyl group and cleavage of the silyl unit, alcohol XXXI is obtained, which can now be inverted according to known methods (tosylating or mesylating and nucleophilic substitution; Mitsonobu-Inversion, etc.). Alternation of the protective groups is attributed to the sequence that is known from the literature [M. Calverley Tetrahedron 43, 4909 (1987)]. Compound XXXIV can be treated exactly like the corresponding compound of the normal series and can produce all products—in the 3-epi series—that are described for the latter.

If $X'_1$, $X'_2$, $E_2$ and $Q'$ are to mean a triple bond in general formula I, the aldehyde of general formula XIII is reacted according to known processes [P. Savignac et al. Synthesis 535 (1975), B. Jiang et al. Synthetic communications 25, 3641 (1995)] to dihalogen compounds of general formula XXXV,

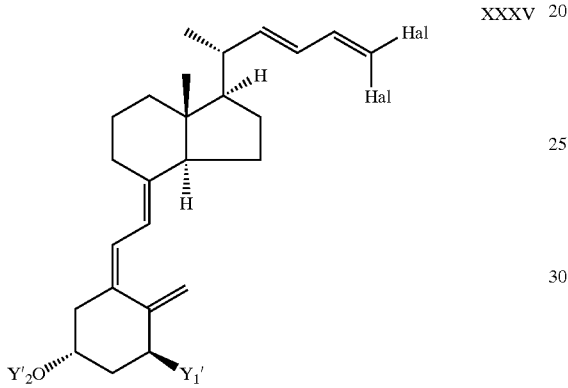

XXXV in which Hal means chlorine or bromine. After reaction with two equivalents of a lithium alkyl compound (e.g., n-butyllithium, t-butyllithium, methyllithium) or lithium diisopropylamide, an acetylide anion is obtained as an intermediate product, which can be reacted with electrophiles [e.g., Cl—PO(OR$_9$)$_2$] to compounds of general formula II, which can be converted as described into compounds of general formula I for which $X_1$, $X_2$, $E_1$, $E_2$ and $Q$ have corresponding meanings.

In the forming of the compound of general formula XXXV for which Hal=chlorine, there is obtained as a by-product a compound of general formula XXXVI

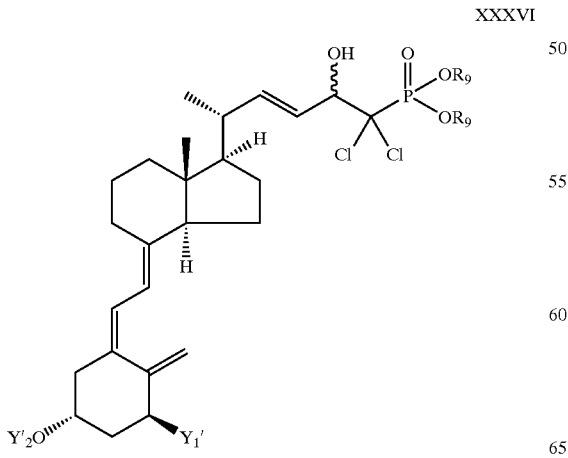

XXXVI that can also be converted into compounds of general formula I.

If the aldehyde of general formula XIII is reacted with deprotonated difluoromethylphosphonic acid esters [e.g., LiCF$_2$—-PO(OR$_9$)$_2$], compounds of general formula XXXVII,

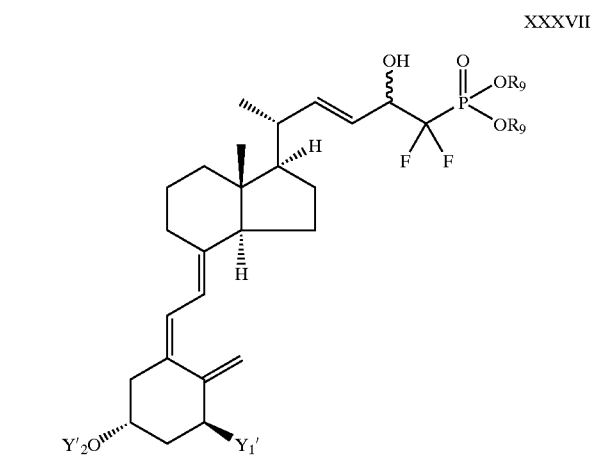

XXXVII that can also be converted into compounds of general formula I, are obtained.

If the aldehyde of general formula XIII is reacted under Knoevenagel conditions [W. Lehnert Tetrahedron 30, 301 (1974)] with methylene bisphosphonic acid esters, compounds of general formula XXXVIII,

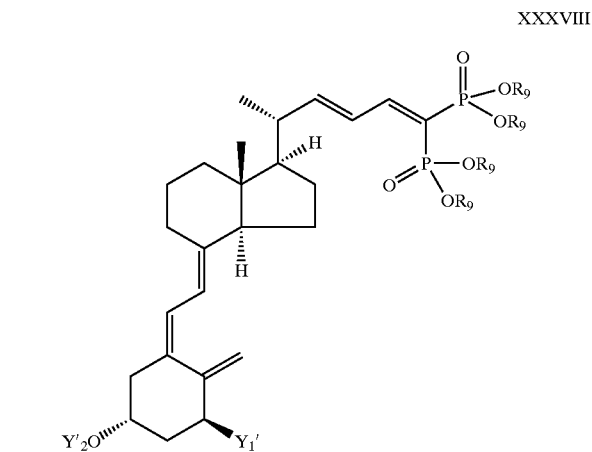

XXXVIII that also can be converted into compounds of general formula I, are obtained.

If the aldehyde of general formula XIII is reacted with trichloromethylphosphonic acid esters in the presence of a base (e.g., n-butyllithium, t-butyllithium, methyllithium, lithium diisopropylamide), compounds of general formula XXIX,

XXXIX

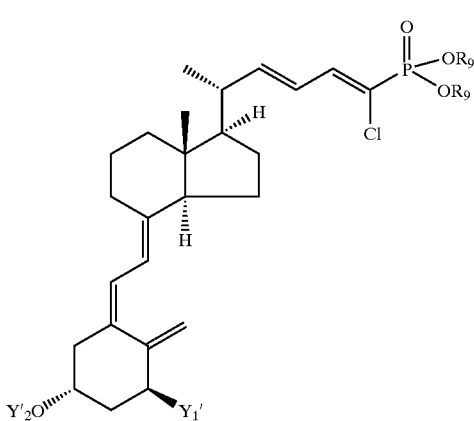

that also can be converted into compounds of general formula I, are obtained.

If compounds of general formula II, for which it holds true that $X'_1$ and $X'_2$ together mean a carbonyl group, $E_2$ and Q' represent hydrogen atoms and $E_1$ has the definition already provided above, after deprotonation with a base (e.g., sodium hydride, potassium hydride, lithium diisopropylamide, sodium alcoholates, potassium alcoholates) are reacted with electrophilic reagents (e.g., alkyl halides), compounds of general formula II with corresponding definitions for $E_1$, $E_2$ and Q' are obtained.

If it holds true that $E_2$ and Q' and the C atom 24 do not exist in compounds of general formula II, the aldehyde of general formula XIII is reacted with dialkylphosphite derivatives, which had been deprotonated with a base (e.g., lithium diisopropylamide, sodium hydride, potassium hydride), whereby compounds of general formula XXXX accumulate,

XXXX

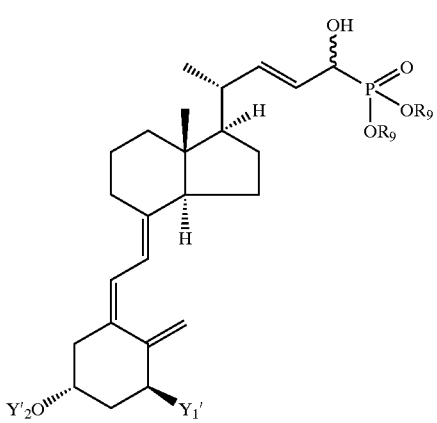

which can then be converted into compounds of general formula I with corresponding meanings of the variables.

In addition, the hydroxyl group in the side chain can also be oxidized to the carbonyl group, in which an oxidizing agent (e.g., manganese dioxide, pyridinium chlorochromate, pyridinium dichromate, oxalyl chloride/dimethyl sulfoxide, Dess-Martin reagent) is used and then the conversion into compounds of general formula I takes place.

The examples below are used for a more detailed explanation of the invention.

EXAMPLE 1

(5Z,7E,22E)-(1S,3R)-(1,3-Dihydroxy-24-oxo-24a-homo-9,10-secochola-5,7,10(19),22-tetraen-24a-yl) phosphonic acid dimethyl ester 5 a) 7.5 g of (5E,7E)-(1S,3R)-1,3-bis[[dimethyl(1,1-dimethylethyl)silyl]oxy]-9,10-secopregna-5,7,10(19)-triene-20-carbaldehyde 1 [M. J. Calverley Tetrahedron 43, 4609–4619 (1987)] is dissolved in 200 ml of toluene, 2 g of anthracene and 0.5 ml of triethylamine are added and irradiated while nitrogen is passing through it in a Pyrex apparatus with a high-pressure mercury-vapor lamp for 30 minutes. Then, it is filtered, concentrated by evaporation, and the residue is chromatographed on silica gel with ethyl acetate/hexane, whereby 7.1 g of (5Z,7E)-(1S,3R)-1,3-bis[[dimethyl(1,1-dimethylethyl)silyl]oxy]-9,10-secopregna-5,7,10(19)-triene-20-carbaldehyde 2 is obtained as a colorless foam.

$^1$H-NMR (300 MHz, CDCl$_3$): δ=0.05 ppm (s, 12H); 0.55 (s, 3H); 0.88 (s, 18H); 1.11 (d, 3H); 2.37 (m, 1H); 4.18 (m, 1H); 4.37 (m, 1H); 4.84 (s, 1H); 5.17 (s, 1H); 6.00 (d, 1H); 6.22 (d, 1H); 9.58 (d, 1H)

b) 455 mg of sodium hydride (60% suspension in paraffin oil) is introduced into 40 ml of tetrahydrofuran (THF) under nitrogen, and 2.69 g of trimethylphosphonoacetate in 5 ml of THF is added in drops at 0° C. After 30 minutes, 1.8 g of aldehyde 2 in 20 ml of THF is added in drops. It is stirred for one more hour at room temperature and then quenched with sodium chloride solution. It is extracted with ethyl acetate, the organic phase is washed with sodium chloride solution, dried on sodium sulfate and concentrated by evaporation. The residue is purified by chromatography on silica gel with ethyl acetate/hexane, whereby 1.4 g of (5Z,7E,22E)-(1S,3R)-1,3-bis[[dimethyl (1,1-dimethylethyl)silyl]oxy]-9,10-secochola-5,7,10(19), 22-tetraenoic-24-acid methyl ester 3 is obtained as a colorless foam.

$^1$H-NMR (300 MHz, CDCl$_3$): δ=0.05 ppm (s, 12H); 0.57 (s, 3H); 0.90 (s, 18H); 1.09 (d, 3H); 3.72 (s, 3H); 4.19 (m, 1H); 4.38 (m, 1H); 4.87 (s, 1H); 5.19 (s, 1H); 5.77 (d, 1H); 6.02 (d, 1H); 6.23 (d, 1H); 6.87 (dd, 1H)

c) 90 mg of methanephosphonic acid dimethyl ester is introduced into 5 ml of THF under nitrogen, and it is cooled to −78° C. 0.48 ml of n-butyllithium solution (1.6 M in hexane) is now added in drops, and it is stirred for 30 minutes at this temperature. Then, 430 mg of ester 3 in 1 ml of THF is added in drops and stirred for another 30 minutes at −78° C. It is quenched with sodium chloride solution, extracted with ethyl acetate, the organic phase is washed with sodium chloride solution, dried on sodium sulfate and concentrated by evaporation. The residue is purified by chromatography on silica gel with ethyl acetate/hexane, whereby 376 mg of (5Z,7E,22E)-(1S,3R)-[1,3-bis[[dimethyl(1,1-dimethylethyl)silyl]oxy]-24-oxo-24a-homo-9,10-secochola-5,7,10(19),22-tetraen-24a-yl] phosphonic acid dimethyl ester 4 is obtained as a colorless foam.

$^1$H-NMR (300 MHz, CD$_2$Cl$_2$): δ=0.05 ppm (s, 12H); 0.54 (s, 3H); 0.86 (s, 18H); 1.10 (d, 3H); 3.16 (d, 2H); 3.71 (s, 3H); 3.73 (s, 3H); 4.16 (m, 1H); 4.36 (m, 1H); 4.82 (s, 1H); 5.16 (s, 1H); 6.01 (d, 1H); 6.07 (d, 1H); 6.23 (d, 1H); 6.72 (dd, 1H)

d) 35 mg of phosphonic acid ester 4 is dissolved in a mixture that consists of 1 ml of dichloromethane and 9 ml of methanol, and it is stirred under nitrogen with 350 mg of activated acidic Dowex ion exchanger overnight at room temperature. It is filtered, the filtrate is washed with sodium bicarbonate solution and sodium chloride solution, dried on sodium sulfate, and the solvent is removed. The residue is purified by chromatography on silica gel with ethyl acetate/hexane, whereby 16 mg of title compound 5 is obtained as a colorless foam.

$^1$H-NMR (300 MHz, CD$_2$Cl$_2$): δ=0.57 ppm (s, 3H); 1.10 (d, 3H); 3.18 (d, 2H); 3.68 (s, 3H); 3.74 (s, 3H); 4.17 (m, 1H); 4.37 (m, 1H); 4.96 (s, 1H); 5.28 (s, 1H); 6.00 (d, 1H); 6.09 (d, 1H); 6.35 (d, 1H); 6.77 (dd, 1H)

EXAMPLE 2

(5Z,7E,22E)-(1S,3R,24S)-(1,3,24-Trihydroxy-24a-homo-9,10-secochola-5,7,10(19),22-tetraen-24a-yl) phosphonic acid dimethyl ester 7a and (5Z,7E,22E)-(1S,3R,24R)-(1,3,24-trihydroxy-24a-homo-9,10-secochola-5,7,10(19),22-tetraen-24a-yl) phosphonic acid dimethyl ester 7b a) 80 mg of ketone 4 is dissolved in 2 ml of dichloromethane, and 8 ml of ethanol is added under nitrogen. 52 mg of cerium trichloride (heptahydrate) and 6 mg of sodium borohydride are added in succession at 0° C. and stirred for 15 more minutes. Then, sodium chloride solution is added, extracted with ethyl acetate, the organic phase is washed with sodium chloride solution and dried on sodium sulfate. After concentration by evaporation, the residue is chromatographed on silica gel with ethyl acetate/hexane, and 61 mg of (5Z,7E,22E)-(1S,3R)-[1,3-bis[[dimethyl(1,1-dimethylethyl)silyl]oxy]-24-hydroxy-24a-homo-9,10-secochola-5,7,10(19),22-tetraen-24a-yl] phosphonic acid dimethyl ester 6 is obtained as a colorless foam (1:1 mixture of the diastereomers in terms of C-24).

$^1$H-NMR (300 MHz, CD$_2$Cl$_2$): δ=0.05 ppm (s, 12H); 0.53 (s, 3H); 0.86 (s, 18H); 1.01/1.02 (in each case d, 3H); 3.17/3.23 (in each case d, OH); 3.68 (d, 3H); 3.72 (d, 3H); 4.16 (m, 1H); 4.35 (m, 1H); 4.36 (m, 1H); 4.82 (s, 1H); 5.16 (s, 1H); 5.37/5.38 (in each case dd, 1H); 5.49/5.51 (in each case dd, 1H); 6.01 (d, 1H); 6.23 (d, 1H)

b) 61 mg of diastereomer mixture 6 is treated analogously to 1d), and the epimers are ultimately separated by HPLC, whereby 12 mg of title compound 7a and 11 mg of title compound 7b are obtained in succession in each case as a colorless foam.

$^1$H-NMR (300 MHz, CD$_2$Cl$_2$): 7a: δ=0.58 ppm (s, 3H); 1.02 (d, 3H); 3.21 (sbr, OH); 3.71 (d, 3H); 3.77 (d, 3H); 4.18 (m, 1H); 4.38 (m, 1H); 4.41 (m, 1H); 4.97 (s, 1H); 5.30 (s, 1H); 5.41 (dd, 1H); 5.58 (dd, 1H); 6.01 (d, 1H); 6.35 (d, 1H)

7b: δ=(0.58 ppm (s, 3H); 1.03 (d, 3H); 3.28 (sbr, OH); 3.71 (d, 3H); 3.77 (d, 3H); 4.18 (m, 1H); 4.38 (m, 1H); 4.42 (m, 1H); 4.97 (s, 1H); 5.30 (s, 1H); 5.39 (dd, 1H); 5.55 (dd, 1H); 6.01 (d, 1H); 6.35 (d, 1H)

EXAMPLE 3

(5Z,7E,22E)-(1S,3R)-(1,3-Dihydroxy-24-oxo-24a-homo-9,10-secochola-5,7,10(19),22-tetraen-24a-yl) phosphonic acid diethyl ester 9 a) 867 mg of methanephosphonic acid diethyl ester with 1.2 g of ester 3 is reacted analogously to 1c), and 1.05 g of (5Z,7E,22E)-(1S,3R)-[1,3-bis[[dimethyl(1,1-dimethylethyl)silyl]oxy]-24-oxo-24a-homo-9,10-secochola-5,7,10(19),22-tetraen-24a-yl]phosphonic acid diethyl ester 8 is obtained as a colorless foam.

$^1$H-NMR (300 MHz, CDCl$_3$): δ=0.06 ppm (s, 12H); 0.57 (s, 3H); 0.89 (s, 18H); 1.11 (d, 3H); 1.33 (t, 6H); 3.19 (d, 2H); 4.13 (q, 2H); 4.16 (q, 2H); 4.17 (m, 1H); 4.37 (m, 1H); 4.84 (s, 1H); 5.19 (s, 1H); 6.01 (d, 1H); 6.18 (d, 1H); 6.23 (d, 1H); 6.81 (dd, 1H)

b) 80 mg of phosphonic acid ester 8 is treated analogously to 1d), and 47 of title compound 9 is obtained as a colorless foam.

$^1$H-NMR (300 MHz, CD$_2$Cl$_2$): δ=0.56 ppm (s, 3H); 1.08 (d, 3H); 1.27 (t, 6H); 3.16 (d, 2H); 4.05 (q, 2H); 4.07 (q, 2H); 4.16 (m, 1H); 4.37 (m, 1H); 4.95 (s, 1H); 5.29 (s, 1H); 6.00 (d, 1H); 6.09 (d, 1H); 6.35 (d, 1H); 6.76 (dd, 1H)

EXAMPLE 4

(5Z,7E,22E)-(1S,3R,24S)-(1,3,24-Trihydroxy-24a-homo-9,10-secochola-5,7,10(19),22-tetraen-24a-yl) phosphonic acid diethyl ester 11a and (5Z,7E,22E)-(1S,3R,24R)-(1,3,24-trihydroxy-24a-homo-9,10-secochola-5,7,10(19),22-tetraen-24a-yl)phosphonic acid diethyl ester 11b 300 mg of phosphonic acid ester 8 is treated analogously to 2a), and 190 mg of (5Z,7E,22E)-(1S,3R)-[1,3-bis[[dimethyl(1,1-dimethylethyl)silyl]oxy]-24-hydroxy-4a-homo-9,10-secochola-5,7,10(19),22-tetraen-24a-yl] phosphonic acid ethyl ester 10 is obtained as a colorless foam (1:1 mixture of diastereomers in terms of C-24).

$^1$H-NMR (300 MHz, CD$_2$Cl$_2$): δ=0.06 ppm (s, 12H); 0.52 (s, 3H); 0.86 (s, 18H); 1.01/1.02 (in each case d, 3H); 1.30 (t, 6H); 4.05 (q, 2H); 4.08 (q, 2H); 4.16 (m, 1H); 4.35 (m, 1H); 4.37 (m, 1H); 4.83 (s, 1H); 5.16 (s, 1H); 5.38/5.39 (in each case dd, 1H); 5.50/5.51 (in each case dd, 1H); 6.01 (d, 1H); 6.23 (d, 1H)

b) 170 mg of diastereomer mixture 10 is treated analogously to 1d), and the epimers are ultimately separated by HPLC, whereby 36 mg of title compound 11a and 28 mg of title compound 11b are obtained in succession in each case as a colorless foam.

$^1$H-NMR (300 MHz, CD$_2$Cl$_2$): 11a: δ=0.55 ppm (s, 3H); 1.02 (d, 3H); 1.31 (t, 6H); 4.07 (q, 2H); 4.09 (1, 2H); 4.17 (m, 1H); 4.37 (m, 1H); 4.40 (m, 1H); 4.96 (s, 1H); 5.29 (s, 1H); 5.40 (dd, 1H); 5.57 (dd, 1H); 6.01 (d, 1H); 6.36 (d, 1H)

11b: δ=0.55 ppm (s, 3H); 1.02 (d, 3H); 1.30 (t, 6H); 4.07 (q, 2H); 4.09 (q, 2H); 4.17 (m, 1H); 4.38 (m, 1H); 4.41 (m, 1H); 4.96 (s, 1H); 5.29 (s, 1H); 5.39 (dd, 1H); 5.54 (dd, 1H); 6.01 (d, 1H); 6.36 (d, 1H)

EXAMPLE 5

(5Z,7E,22E)-(1S,3R)-(1,3-Dihydroxy-24-oxo-24a-homo-9,10-secochola-5,7,10(19),22-tetraen-24a-yl) phosphonic acid bis(1-methylethyl)ester 13 a) 240 mg of methanephosphonic acid diisopropyl ester is reacted with 500 mg of ester 3 analogously to 1c), and 476 mg of (5Z,7E,22E)-(1S,3R)-[1,3-bis[[dimethyl(1,1-dimethylethyl)silyl]oxy]-24-oxo-24a-homo-9,10-secochola-5,7,10(19),22-tetraen-24a-yl]phosphonic acid bis(1-methylethyl)ester 12 is obtained as a colorless foam.

$^1$H-NMR (300 MHz, CDCl$_3$): δ=0.07 ppm (s, 12H); 0.58 (s, 3H); 0.89 (s, 18H); 1.12 (d, 3H); 1.33 (d, 12H); 3.16 (d, 2H); 4.18 (m, 1H); 4.38 (m, 1H); 4.72 (hept, 2H); 4.86 (s, 1H); 5.18 (s, 1H); 6.01 (d, 1H); 6.19 (d, 1H); 6.23 (d, 1H); 6.80 (dd, 1H)

b) 70 mg of phosphonic acid ester 12 is treated analogously to 1d), and 34 mg of title compound 13 is obtained as a colorless foam.

$^1$H-NMR (300 MHz, CD$_2$Cl$_2$): δ=0.58 ppm (s, 3H); 1.10 (d, 3H); 1.30 (d, 12H); 3.10 (d, 2H); 4.18 (m, 1H); 4.38 (m, 1H); 4.68 (hept, 2H); 4.96 (s, 1H); 5.29 (s, 1H); 6.01 (d, 1H); 6.12 (d, 1H); 6.36 (d, 1H); 6.76 (dd, 1H)

EXAMPLE 6

(5Z,7E,22E)-(1S,3R,24S)-(1,3,24-Trihydroxy-24a-homo-9,10-secochola-5,7,10(19),22-tetraen-24a-yl) phosphonic acid bis(1-methylethyl)ester 15a and (5Z,7E,22E)-(1S,3R,24R)-(1,3,24-trihydroxy-24a-homo-9,10-secochola-5,7,10(19),22-tetraen-24a-yl) phosphonic acid bis(1-methylethyl)ester 15b 250 mg of phosphonic acid ester 12 is treated analogously to 2a), and 178 mg of (5Z,7E,22E)-(1S,3R)-[1,3-bis[[dimethyl(1,1-dimethylethyl)silyl]oxy]-24-hydroxy-24a-homo-9,10-secochola-5,7,10(19),22-tetraen-24a-yl] phosphonic acid bis(1-methylethyl)ester 14 is obtained as a colorless foam (1:1 mixture of diastereomers in terms of C-24).

$^1$H-NMR (300 MHz, CD$_2$Cl$_2$): δ=0.06 ppm (s, 12H); 0.52 (s, 3H); 0.86 (s, 18H); 1.00/1.02 (in each case d, 3H); 1.31 (d, 12H); 4.16 (m, 1H); 4.35 (m, 2H); 4.63 (hept, 2H); 4.83 (s, 1H); 5.16 (s, 1H); 5.37/5.38 (in each case dd, 1H); 5.50/5.52 (in each case dd, 1H); 6.00 (d, 1H); 6.22 (d, 1H)

b) 130 mg of diastereomer mixture 14 is treated analogously to 1d), and the epimers are ultimately separated by HPLC, whereby 34 mg of title compound 15a and 33 mg of title compound 15b are obtained in succession in each case as a colorless foam.

$^1$H-NMR (300 MHz, CD$_2$Cl$_2$): 15a: δ=0.56 ppm, (s, 3H); 1.03 (d, 3H); 1.31 (d, 12H); 4.18 (m, 1H); 4.38 (m, 2H); 4.68 (hept, 2H); 4.95 (s, 1H); 5.28 (s, 1H); 5.40 (dd, 1H); 5.56 (dd, 1H); 6.00 (d, 1H); 6.36 (d, 1H)

15b: δ=0.55 ppm (s, 3H); 1.04 (d, 3H); 1.30 (d, 12H); 4.18 (m, 1H); 4.38 (m, 2H); 4.69 (hept, 2H); 4.95 (s, 1H); 5.29 (s, 1H); 5.39 (dd, 1H); 5.53 (dd, 1H); 6.00 (d, 1H); 6.35 (d, 1H)

EXAMPLE 7

(5Z,7E,22E,24Z)-(1S,3R)-Phosphoric acid[1,3-dihydroxy-24a-(diethoxy)phosphinyl-24a-homo-9,10-secochola-5,7,10(19),22-pentaen-24-yl]diethyl ester 17 a) Lithium diisopropylamide (LDA) is prepared from 0.16 ml of diisopropylamine and 0.48 ml of n-butyllithium solution (1.6 M in hexane) in 20 ml of THF at −78° C. under nitrogen, and 650 mg of ketone 8 is added in drops. It is stirred for 30 minutes at this temperature, and then 414 mg of diethylchlorophosphate is added. It is heated to 0° C., and stirred for one more hour. Then, it is quenched with sodium chloride solution, extracted with ethyl acetate, the organic phase is washed with sodium chloride solution, dried on sodium sulfate and concentrated by evaporation. The residue is chromatographed on silica gel with ethyl acetate/hexane, whereby 216 mg of (5Z,7E,22E,24Z)-(1S,3R)-phosphoric acid[1,3-bis[[dimethyl(1,1-dimethylethyl)silyl]oxy]-24a-(diethoxy)phosphinyl-24a-homo-9,10-secochola-5,7,10(19),22,24-pentaen-24-yl]diethyl ester 16 accumulates as a colorless foam.

$^1$H-NMR (300 MHz, CD$_2$Cl$_2$): δ=0.05 ppm (s, 12H); 0.56 (s, 3H); 0.86 (s, 18H); 1.07 (d, 3H); 1.28 (t, 6H); 1.31 (t, 6H); 4.07 (q, 4H); 4.22 (q, 4H); 4.17 (m, 1H); 4.37 (m, 1H); 4.84 (s, 1H); 5.15 (d, 1H); 5.18 (s, 1H); 5.96 (d, 1H); 6.00 (d, 1H); 6.22 (d, 1H); 6.28 (dd, 1H)

b) 105 mg of phosphonic acid ester 16 is treated analogously to 1d), and 56 mg of title compound 17 is obtained as a colorless foam.

$^1$H-NMR (300 MHz, CD$_2$Cl$_2$): δ=0.57 ppm (s, 3H); 1.07 (d, 3H); 1.29 (t, 6H); 1.31 (t, 6H); 4.03 (q, 2H); 4.07 (q, 2H); 4.21 (q, 2H); 4.24 (q, 2H); 4.18 (m, 1H); 4.38 (m, 1H); 4.96 (s, 1H); 5.17 (d, 1H); 5.29 (s, 1H); 5.99 (d, 1H); 6.00 (d, 1H); 6.29 (dd, 1H); 6.33 (d, 1H)

EXAMPLE 8

(5Z,7E,22E,24E)-(1S,3R)-(1,3-Dihydroxy-24a-homo-9,10-secochola-5,7,10(19),22,24-pentaen-24a-yl)phosphonic acid diethyl ester 20 a) 10 mg of sodium hydride (80% in paraffin oil) is introduced into 2 ml of THF under nitrogen and cooled to 0° C. 61 mg of tetraethylmethylene bisphosphonate is now added in drops, and it is stirred for 5 minutes at this temperature. Then, 125 mg of (5Z,7E,22E)-(1S,3R)-1,3-bis[[dimethyl(1,1-dimethylethyl)silyl]oxy]-9,10-secochola-5,7,10(19),22-tetraen-24-al 18 (P 51405 Schering AG) in 1 ml of THF is added in drops and stirred for 1 hour at room temperature. Then, the sodium chloride solution is added, it is extracted with ethyl acetate, the organic phase is washed with sodium chloride solution, dried on sodium sulfate, and the solvent is removed. The residue is chromatographed on silica gel with ethyl acetate/hexane, whereby 89 mg of (5Z,7E,22E)-(1S,3R)-[1,3-bis[[dimethyl(1,1-dimethylethyl)silyl]oxy]-24a-homo-9,10-secochola-5,7,10(19),22,24-pentaen-24a-yl] phosphonic acid diethyl ester 19 is obtained as a colorless foam.

$^1$H-NMR (300 MHz, CDCl$_3$): δ=0.06 ppm (s, 12H); 0.57 (s, 3H); 0.89 (s, 18H); 1.08 (d, 3H); 1.32 (t, 6H); 4.08 (q, 2H); 4.10 (q, 2H); 4.18 (m, 1H); 4.38 (m, 1H); 4.86 (s, 1H); 5.18 (s, 1H); 5.57 (dd, 1H); 5.95 (dd, 1H); 6.02 (d, 1H); 6.09 (dd, 1H); 6.24 (d, 1H); 7.07 (dd, 1H)

b) 60 mg of phosphonic acid ester 19 is treated analogously to 1d), and 31 mg of title compound 20 is obtained as a colorless foam.

$^1$H-NMR (300 MHz, CD$_2$Cl$_2$): δ=0.53 ppm (s, 3H); 1.03 (d, 3H); 1.26 (t, 6H); 4.00 (q, 2H); 4.03 (q, 2H); 4.17 (m, 1H); 4.37 (m, 1H); 4.95 (s, 1H); 5.28 (s, 1H); 5.53 (dd, 1H); 5.94 (dd, 1H); 6.00 (d, 1H); 6.05 (dd, 1H); 6.34 (d, 1H); 6.95 (dd, 1H)

EXAMPLE 9

(5Z,7E,22E)-(1S,3R)-24-(Diphenylphosphinyl)-9,10-secochola-5,7,10(19),22-tetraene-1,3-diol 23 a) 750 mg of (5Z,7E,22E)-(1S,3R)-1,3-bis[[dimethyl(1,1-dimethylethyl)silyl]oxy]-9,10-secochola-5,7,10(19),22-tetraen-24-al 18 is introduced into 20 ml of toluene under nitrogen, and 2.58 ml of diisobutylaluminum solution (1.2 M in toluene) is added in drops at −78° C. After 30 minutes at this temperature, 3 ml of a water/isopropanol mixture (1:1) is added in drops, and it is stirred for one more hour. The precipitate is then filtered off, and the filtrate is concentrated by evaporation and purified by chromatography on silica gel with ethyl acetate/hexane, whereby 550 mg of (5Z,7E,22E)-(1S,3R)-1,3-bis[[dimethyl(1,1-dimethylethyl)silyl]oxy]-9,10-secochola-5,7,10(19),22-tetraen-24-ol 21 is obtained as a colorless foam.

$^1$H-NMR (300 MHz, CDCl$_3$): δ=0.06 ppm (s, 12H); 0.58 (s, 3H); 0.88 (s, 18H); 1.07 (d, 3H); 4.08 (m, 2H); 4.18 (m, 1H); 4.38 (m, 1H); 4.87 (s, 1H); 5.18 (s, 1H); 5.57 (m, 2H); 6.01 (d, 1H); 6.24 (d, 1H)

b) 80 mg of alcohol 21 is introduced into 2 ml of THF under nitrogen, cooled to 0° C., and 0.06 ml of n-butyllithium solution (1.6 M in hexane) is added in drops and stirred for 10 more minutes. 26 mg of p-toluenesulfonic acid chloride in 1 ml of THF is now added and stirred again for 10 minutes. At the same time, a solution of 25 mg of diphenylphosphine in 2 ml of THF is treated at −10° C. under nitrogen with 0.05 ml of n-butyllithium solution (1.6 M in hexane), and it is stirred for 10 minutes. The tosylate that is generated in situ is added in drops to this solution, and it is stirred for one more hour at room temperature. The reaction mixture is concentrated by evaporation, and the residue is dissolved in 3 ml of chloroform. 0.5 ml of hydrogen peroxide solution (5% in water) is now added and stirred for two more hours at room temperature. The phases are separated, the organic phase is washed with sodium thiosulfate solution, dried on sodium sulfate and concentrated by evaporation. The residue is chromatographed on silica gel with ethyl acetate/hexane, whereby 58 mg of (5Z,7E,22E)-(1S,3R)-1,3-bis[[dimethyl(1,1-dimethylethyl)silyl]oxy]-24-(diphenylphosphinyl)-9,10-secochola-5,7,10(19),22-tetraene 22 accumulates as a colorless foam.

$^1$H-NMR (300 MHz, CD$_2$Cl$_2$): δ=0.05 ppm (s, 12H); 0.42 (s, 3H); 0.86 (s, 18H); 0.92 (d, 3H); 3.01 (d, 2H); 4.16 (m, 1H); 4.36 (m, 1H); 4.84 (s, 1H); 5.16 (s, 1H); 5.30 (m, 2H); 5.99 (d, 1H); 6.22 (d, 1H); 7.48 (m, 6H); 7.68 (m, 4H)

c) 34 mg of phosphine oxide 22 is treated analogously to 1d), and 16 mg of title compound 23 is obtained as a colorless foam.

$^1$H-NMR (300 MHz, CD$_2$Cl$_2$): δ=0.47 ppm (s, 3H); 0.88 (d, 3H); 3.02 (d, 2H); 4.17 (m, 1H); 4.37 (m, 1H); 4.92 (s, 1H); 5.28 (s, 1H); 5.30 (m, 2H); 5.98 (d, 1H); 6.30 (d, 1H); 7.47 (m, 6H); 7.68 (m, 4H)

EXAMPLE 10

(5Z,7E,22E)-(1S,3R)-(1,3-Dihydroxy-24-oxo-24a-homo-9,10-secochola-5,7,10(19),22-tetraen-24a-yl) phosphonic acid-monoethylester 24 and (5Z,7E,22E)-(1S,3R)-(1,3-dihydroxy-24-oxo-24a-homo-9,10-secochola-5,7,10(19),22-tetraen-24a-yl) phosphonic acid 25

40 mg of ketophosphonate 9 is introduced into 9 ml of dichloromethane, and 0.1 ml of collidine and 0.06 ml of trimethyl silyl bromide are added. It is stirred for 4 hours at room temperature and then quenched with water. After the water phase is extracted with ethyl acetate, the organic phase is rewashed with sodium chloride solution, dried on sodium sulfate, and the solvent is removed. The residue is purified by chromatography on silica gel with ethyl acetate/hexane, whereby 12 mg of title compound 24 and 14 mg of title compound 25 accumulate in succession as colorless foams.

$^1$H-NMR (300 MHz, CD$_2$Cl$_2$/CD$_3$OD): 24: δ=0.50 ppm (s, 3H); 1.01 (d, 3H); 1.12 (t, 3H); 2.95 (d, 2H); 3.80 (q, 2H); 4.03 (m, 1H); 4.24 (m, 1H); 4.83 (s, 1H); 5.18 (s, 1H); 5.98 (d, 1H); 6.10 (d, 1H); 6.23 (d, 1H); 6.69 (dd, 1H)

25: δ=0.50 ppm (s, 3H); 1.02 (d, 3H); 2.92 (d, 2H); 4.01 (m, 1H); 4.23 (m, 1H); 4.83 (s, 1H); 5.19 (s, 1H); 5.96 (d, 1H); 6.08 (d, 1H); 6.23 (d, 1H); 6.72 (dd, 1H)

EXAMPLE 11

(5Z,7E,22E,24E)-(1S,3R)-(1,3-Dihydroxy-24a-homo-9,10-secochola-5,7,10(19),22,24-pentaen-24a-yl)phosphonic acid-monoethyl ester 26 and (5Z,7E,22E,24E)-(1S,3R)-(1,3-dihydroxy-24a-homo-9,10-secochola-5,7,10(19),22,24-pentaen-24a-yl) phosphonic acid 27

110 mg of phosphonic acid ester 20 is treated analogously to 10), and after chromatographic purification on silica gel with ethyl acetate/hexane, 44 mg of title compound 26 and 29 mg of title compound 27 are obtained in succession as colorless foams.

$^1$H-NMR (300 MHz, CD$_3$OD): 26: δ=0.60 ppm (s, 3H); 1.08 (d, 3H); 1.22 (t, 3H); 3.82 (q, 2H); 4.13 (m, 1H); 4.35 (m, 1H); 4.86 (s, 1H); 5.30 (s, 1H); 5.69 (t, 1H); 5.78 (dd, 1H); 6.05 (d, 1H); 6.09 (d, 1H); 6.30 (d, 1H); 6.80 (ddd, 1H)

27: δ=0.60 ppm (s, 3H); 1.07 (d, 3H); 4.13 (m, 1H); 4.35 (m, 1H); 4.86 (s, 1H); 5.29 (s, 1H); 5.72 (dd, 1H); 5.78 (t, 1H); 6.03 (dd, 1H); 6.08 (d, 1H); 6.33 (d, 1H); 6.78 (ddd, 1H)

EXAMPLE 12

(5Z,7E,22E)-(1S,3R,24ξ)-(1,3-Dihydroxy-24a-homo-9,10-secochola-5,7,10(19),22-tetraene-24,24a-diyl)bis[phosphonic acid diethyl ester] 29 a) 0.16 ml of diethyl phosphite is dissolved in 5 ml of THF, cooled to −78° C., and then 0.5 ml of n-butyllithium solution (1.6 M in hexane) is added. After 10 minutes, 230 mg of phosphonic acid ester 19 in 1.5 ml of THF is added, and it is stirred for one more hour at −78° C. and for one hour at −30° C. Sodium chloride solution is added, it is extracted with ethyl acetate, the organic phase is washed with sodium chloride solution, dried on sodium sulfate, and the solvent is removed. The residue is chromatographed on silica gel, whereby 134 mg of (5Z,7E,22E)-(1S,3R,24ξ)-[1,3-bis[[dimethyl-(1,1-dimethylethyl)silyl]oxy]-24a-homo-9,10-secochola-5,7,10(19),22-tetraene-24,24a-diyl]bis-[phosphonic acid diethyl ester] 28 accumulates as a colorless foam.

$^1$H-NMR (300 MHz, CDCl$_3$): δ=0.06 ppm (s, 12H); 0.54 (s, 3H); 0.88 (s, 18H); 1.07 (d, 3H); 1.30 (t, 12H); 4.15 (m, 9H); 4.38 (m, 1H); 4.83 (s, 1H); 5.18 (s, 1H); 5.22 (m, 1H); 5.56 (m, 1H); 6.00 (d, 1H); 6.22 (d, 1H)

b) 70 mg of phosphonic acid ester 28 is treated analogously to 1d), and 22 mg of title compound 29 is obtained as a colorless foam.

$^1$H-NMR (300 MHz, CD$_2$Cl$_2$): δ=0.55 ppm (s, 3H); 1.03 (d, 3H); 1.29 (t, 12H); 4.00 (m, 8H); 4.15 (m, 1H); 4.35 (m, 1H); 4.82 (s, 1H); 5.17 (m, 1H); 5.28 (s, 1H); 5.55 (m, 1H); 6.00 (d, 1H); 6.32 (d, 1H)

EXAMPLE 13

(5Z,7E,22E)-(1S,3R)-(1,3-Dihydroxy-24-nor-9,10-secocholesta-5,7,10(19),22-tetraene-26,27-diyl)bis[phosphonic acid diethyl ester] 31 a) 0.08 ml of diethylmethylphosphonate is dissolved in 2 ml of THF, cooled to −78° C., and then 0.24 ml of n-butyllithium solution (1.6 M in hexane) is added. After 10 minutes, 150 mg of phosphonic acid ester 19 in 1 ml of THF is added, and it is stirred for 4 hours at −78° C. Sodium chloride solution is added, extracted with ethyl acetate, the organic phase is washed with sodium chloride solution, dried on sodium sulfate, and the solvent is removed. The residue is chromatographed on silica gel, whereby 112 mg of (5Z,7E,22E)-(1S,3R)-[1,3-bis[[dimethyl(1,1-dimethylethyl)silyl]oxy]-24-nor-9,10-secocholesta-5,7,10(19),22-tetraene-26,27-diyl]bis[phosphonic acid diethyl ester] 30 accumulates as a colorless foam.

$^1$H-NMR (300 MHz, CD$_2$Cl$_2$): δ=0.06 ppm (s, 12H); 0.53 (s, 3H); 0.86 (s, 18H); 1.01 (d, 3H); 1.30 (t, 12H); 4.05 (m, 8H); 4.16 (m, 1H); 4.36 (m, 1H); 4.84 (s, 1H); 5.17 (s, 1H); 5.39 (m, 21H); 6.00 (d, 1H); 6.23 (d, 1H)

b) 82 mg of phosphonic acid ester 30 is treated analogously to d), and 26 mg of title compound 31 is obtained as a colorless foam.

$^1$H-NMR (300 MHz, CD$_2$Cl$_2$): δ=0.56 ppm (s, 3H); 1.01 (d, 3H); 1.29 (t, 12H); 4.01 (m, 8H); 4.15 (m, 1H); 4.36 (m, 1H); 4.92 (s, 1H); 5.28 (s, 1H); 5.36 (m, 2H); 6.00 (d, 1H); 6.32 (d, 1H)

EXAMPLE 14

(5Z,7E,22E,24E)-(1S,3R)-(1,3-Dihydroxy-24a-homo-9,10-secochola-5,7,10(19),22,24-pentaene-24a,24a-diyl)bis[phosphonic acid diethyl ester] 33 a) 0.07 ml of titanium(IV) chloride and 1.6 ml of carbon tetrachloride are dissolved in 1.4 ml of THF, cooled to 0° C., and then 0.08 ml of tetraethylmethylene bisphosphonate and 200 mg of aldehyde 18, dissolved in 1 ml of THF, are added. After 15 minutes, 0.15 ml of N-methylmorpholine is added, and it is stirred for 2.5 hours at room temperature. Sodium chloride solution is added, extracted with ethyl acetate, the organic phase is washed with dilute hydrochloric acid and with sodium chloride solution, dried on sodium sulfate, and the solvent is removed. The residue is chromatographed on silica gel, whereby 161 mg of (5Z,7E,22E,24E)-(1S,3R)-[1,3-bis[[dimethyl(1,1-dimethylethyl)silyl]oxy]-24a-homo-9,10-secochola-5,7,10(19),22,24-pentaene-24a,24a-diyl]bis[phosphonic acid diethyl ester] 32 accumulates as a colorless foam.

$^1$H-NMR (300 MHz, CDCl$_3$): δ=0.07 ppm (s, 12H); 0.54 (s, 3H); 0.86 (s, 18H); 1.06 (d, 3H); 1.32 (t, 12H); 4.15 (m, 9H); 4.36 (m, 1H); 4.83 (s, 1H); 5.18 (s, 1H); 6.00 (d, 1H); 6.22 (dd, 1H); 6.23 (d, 1H); 7.10 (dd, 1H); 7.75 (dddd, 1H)

b) 68 mg of phosphonic acid ester 32 is treated analogously to 1d), and 34 mg of title compound 33 is obtained as a colorless foam.

$^1$H-NMR (300 MHz, CD$_2$Cl$_2$): δ=0.56 ppm (s, 3H); 1.07 (d, 3H); 1.31 (t, 12H); 4.08 (m, 8H); 4.15 (m, 1H); 4.36 (m, 1H); 4.93 (s, 1H); 5.28 (s, 1H); 6.00 (d, 1H); 6.24 (dd, 1H); 6.33 (d, 1H); 7.00 (dd, 1H); 7.64 (dddd, 1H)

EXAMPLE 15

(5Z,7E,22E,24Z)-(1S,3R)-(24a-Chloro-1,3-dihydroxy-24a-homo-9,10-secochola-5,7,10(19),22,24-pentaen-24a-yl)phosphonic acid diethyl ester 35 a) 0.06 ml of diethyltrichlorophosphonate is introduced into 3 ml of diethyl ether and cooled to −78° C. At this temperature, 0.15 ml of N-butyllithium solution (1.6 M in hexane) is added in drops. After 30 minutes, 200 mg of aldehyde 18 is added, and it is stirred for 1 hour at −78° C. Sodium chloride solution is added, extracted with ethyl acetate, the organic phase is washed with sodium chloride solution, dried on sodium sulfate, and the solvent is removed. The residue is chromatographed on silica gel, whereby 188 mg of (5Z,7E,22E,24Z)-(1S,3R)-[1,3-bis[[dimethyl(1,1-dimethylethyl)silyl]oxy]-24a-chloro-24a-homo-9,10-secochola-5,7,10(19),22,24-pentaen-24a-yl]phosphonic acid diethyl ester 34 accumulates as a colorless foam.

$^1$H-NMR (300 MHz, CDCl$_3$): δ=0.07 ppm (s, 12H); 0.56 (s, 3H); 0.88 (s, 18H); 1.10 (d, 3H); 1.32 (t, 6H); 4.15 (m, 5H); 4.36 (m, 1H); 4.83 (s, 1H); 5.18 (s, 1H); 6.00 (d, 1H); 6.09 (dd, 1H); 6.23 (d, 1H); 6.42 (dd, 1H); 7.25 (dd, 1H)

b) 110 mg of phosphonic acid ester 34 is treated analogously to 1d), and 53 mg of title compound 35 is obtained as a colorless foam.

$^1$H-NMR (300 MHz, CD$_2$Cl$_2$): δ=0.56 ppm (s, 3H); 1.08 (d, 3H); 1.29 (t, 6H); 4.06 (m, 4H); 4.15 (m, 1H); 4.36 (m, 1H); 4.95 (s, 1H); 5.28 (s, 1H); 6.00 (d, 1H); 6.09 (dd, 1H); 6.33 (d, 1H); 6.40 (dd, 1H); 7.16 (dd, 1H)

EXAMPLE 16

(5Z,7E,22E)-(1S,3R)-(1,3-Dihydroxy-24a-homo-9,10-secochola-5,7,10(19),22-tetraen-24-in-24a-yl) phosphonic acid diethyl ester a) 114 mg of triphenylphosphine is introduced at 0° C. in 2 ml of dichloromethane, and 72 mg of tetrabromomethane, 100 mg of aldehyde 18 and 0.02 ml of triethylamine are then added in succession, and it is stirred for one hour at 0° C. Sodium chloride solution is added, extracted with ethyl acetate, the organic phase is washed with sodium chloride solution, dried on sodium sulfate, and the solvent is removed. The residue is chromatographed on silica gel, whereby 109 mg of (5Z,7E,22E)-(1S,3R)-[1,3-bis[[dimethyl(1,1-dimethylethyl)silyl]oxy]-24a,24a-dibromo-24-homo-9,10-secochola-5,7,10(19),22,24-pentaen-24a-yl]phosphonic acid diethyl ester 36 accumulates as a colorless foam.

$^1$H-NMR (300 MHz, CDCl$_3$): δ=0.07 ppm (s, 12H); 0.56 (s, 3H); 0.88 (s, 18H); 1.08 (d, 3H); 4.20 (m, 1H); 4.38 (m, 1H); 4.86 (s, 1H); 5.18 (s, 1H); 5.78 (dd, 1H); 6.00 (d, 1H); 6.01 (d, 1H); 6.23 (d, 1H); 6.88 (d, 1H)

b) 104 mg of dibromide 36 is introduced into 3 ml of THF, and 0.22 ml of n-butyllithium solution (1.6 M in hexane) is added in drops at −78° C. After one hour, 0.1 ml of diethyl chlorophosphonate is then added, and it is stirred for three more hours at room temperature. It is quenched with sodium chloride solution, extracted with ethyl acetate, dried on sodium sulfate, and the residue is chromatographed on silica gel with ethyl acetate/hexane, and 68 mg of (5Z,7E,22E)-(1S,3R)-[1,3-bis[[dimethyl(1,1-dimethylethyl)silyl]oxy]-24a-homo-9,10-secochola-5,7,10(19),22-tetraen-24-in-24a-yl]phosphonic acid diethyl ester 37 is obtained as a colorless foam.

$^1$H-NMR (300 MHz, CDCl$_3$): δ=0.07 ppm (s, 12H); 0.56 (s, 3H); 0.88 (s, 18H); 1.08 (d, 3H); 1.36 (t, 6H); 4.15 (m, 5H); 4.38 (m, 1H); 4.95 (s, 1H); 5.18 (s, 1H); 5.50 (dd, 1H); 6.00 (d, 1H); 6.23 (d, 1H); 6.38 (dd, 1H)

c) 56 mg of phosphonic acid ester 37 is treated analogously to 1d), and after chromatographic purification of the mixture on silica gel with ethyl acetate/hexane, 19 mg of title compound 38 is obtained as a colorless foam.

$^1$H-NMR (300 MHz, CD$_2$Cl$_2$): δ=0.55 ppm (s, 3H); 1.06 (d, 3H); 1.33 (t, 6H); 4.08 (m, 4H); 4.13 (m, 1H); 4.35 (m, 1H); 4.94 (s, 1H); 5.28 (s, 1H); 5.51 (dd, 1H); 6.00 (d, 1H); 6.34 (d, 1H); 6.36 (dd, 1H)

EXAMPLE 17

(5Z,7E,22E)-(1S,3R)-(1,3-Dihydroxy-24a-homo-9,10-secochola-5,7,10(19),22-tetraen-24-in-24a-yl) phosphonic acid monoethyl ester 39 and (5Z,7E,22E)-(1S,3R)-(1,3-dihydroxy-24a-homo-9,10-secochola-5,7,10(19),22-tetraen-24-in-24a-yl) phosphonic acid 40

98 mg of phosphonic acid ester 38 is treated analogously to 10), and after chromatography on silica gel with ethyl acetate/hexane, 20 mg of title compound 39 and 12 mg of title compound 40 are obtained in succession as colorless foams.

$^1$H-NMR (300 MHz, CD$_2$Cl$_2$/CD$_3$OD): 38: δ=0.50 ppm (s, 3H); 1.00 (d, 3H); 1.20 (t, 3H); 3.90 (q, 2H); 4.08 (m, 1H); 4.30 (m, 1H); 4.89 (s, 1H); 5.23 (s, 1H); 5.43 (dd, 1H); 6.00 (d, 1H); 6.11 (dd, 1H); 6.29 (d, 1H)

40: δ=0.50 ppm (s, 3H); 0.98 (d, 3H); 4.08 (m, 1H); 4.30 (m, 1H); 4.86 (s, 1H); 5.23 (s, 1H); 5.40 (d, 1H); 6.00 (d, 1H); 6.03 (dd, 1H); 6.28 (d, 1H)

EXAMPLE 18

(5Z,7E,22E)-(1S,3R,24S)-(24a,24a-Dichloro-1,3,24-trihydroxy-24a-homo-9,10-secochola-5,7,10(19),22-tetraen-24a-yl)phosphonic acid diethyl ester 43a and (5Z,7E,22E)-(1S,3R,24R)-(24a,24a-dichloro-1,3,24-trihydroxy-24a-homo-9,10-secochola-5,7,10 (19),22-tetraen-24a-yl)phosphonic acid diethyl ester 43b a) 350 mg of lithium chloride is dissolved in 5 ml of THF and cooled to 0° C. 1.67 ml of n-butyllithium solution (1.6 M in hexane) is now added in drops. It is cooled to −78° C., then 0.43 ml of carbon tetrachloride is added, it is stirred for another 5 minutes at this temperature, and ultimately 775 mg of aldehyde 18 is added. After another 1.5 hours at −78° C., it is quenched with sodium chloride solution, extracted with ethyl acetate, dried on sodium sulfate and concentrated by evaporation. The residue is chromatographed on silica gel with ethyl acetate/hexane, whereby 163 mg of (5Z,7E,22E)-(1S,3R)-[1,3-bis [[dimethyl(1,1-dimethylethyl)silyl]oxy]-24a,24a-dichloro-24-homo-9,10-secochola-5,7,10(19),22,24-pentaen-24a-yl]phosphonic acid diethyl ester 41 and 344 mg of 42 (5Z,7E,22E)-(1S,3R)-[1,3-bis[[dimethyl(1,1-dimethylethyl)silyl]oxy]-24a,24a-dichloro-24-hydroxy-24a-homo-9,10-secochola-5,7,10(19),22-tetraen-24a-yl] phosphonic acid diethyl ester (diastereomer mixture in terms of C-24) accumulate in succession as colorless foams.

$^1$H-NMR (300 MHz, CDCl$_3$): 41: δ=0.08 ppm (s, 12H); 0.55 (s, 3H); 0.88 (s, 18H); 1.06 (d, 3H); 4.20 (m, 1H); 4.38 (m, 1H); 4.87 (s, 1H); 5.18 (s, 1H); 5.70 (dd, 1H); 6.00 (d, 1H); 6.10 (dd, 1H); 6.34 (dd, 1H); 6.36 (d, 1H)

42: δ=0.08 ppm (s, 12H); 0.57 (s, 3H); 0.88 (s, 18H); 1.08 (d, 3H); 1.32 (t, 6H); 4.10 (m, 5H); 4.38 (m, 1H); 4.86 (s, 1H); 4.97 (m, 1H); 5.18 (s, 1H); 5.55 (dd, 1H); 5.88 (m, 1H); 6.01 (d, 1H); 6.22 (d, 1H)

b) 150 mg of diastereomer mixture 42 is treated analogously to 1d), and after chromatographic purification (HPLC), 34 mg of title compound 43a and 21 mg of title compound 43b are obtained in succession as colorless foams.

$^1$H-NMR (300 MHz, CD$_2$Cl$_2$): 43a: δ=0.55 ppm (s, 3H); 1.05 (d, 3H); 1.29 (t, 6H); 4.07 (m, 4H); 4.16 (m, 1H); 4.35 (m, 1H); 4.94 (s, 1H); 5.28 (s, 1H); 5.53 (dd, 1H); 5.88 (dd, 1H); 6.01 (d, 1H); 6.35 (d, 1H)

43b: δ=0.55 ppm (s, 3H); 1.05 (d, 3H); 1.31 (t, 6H); 4.05 (m, 4H); 4.15 (m, 1H); 4.35 (m, 1H); 4.92 (s, 1H); 5.28 (s, 1H); 5.51 (dd, 1H); 5.82 (dd, 1H); 6.00 (d, 1H); 6.34 (d, 1H)

EXAMPLE 19

(5Z,7E,22E)-(1S,3R,24S)-(24a,24a-Difluoro-1,3,24-trihydroxy-24a-homo-9,10-secochola-5,7,10(19),22-tetraen-24a-yl)phosphonic acid diethyl ester 45a and (5Z,7E,22E)-(1S,3R,24R)-(24a,24a-difluoro-1,3,24-trihydroxy-24a-homo-9,10-secochola-5,7,10 (19),22-tetraen-24a-yl)phosphonic acid diethyl ester 45b a) 0.22 mmol of lithium diisopropylamide is produced in THF as usual, and 0.03 ml of diethylfluoromethylphosphonate is added at −78° C. After 1 hour, 100 mg of aldehyde 18 is then added, and it is stirred for another 30 minutes. It is quenched with sodium chloride solution, extracted with ethyl acetate, the organic phase is washed with sodium chloride solution, dried on sodium sulfate and concentrated by evaporation. The residue is chromatographed on silica gel with ethyl acetate/hexane, whereby 33 mg of (5Z,7E,22E)-(1S,3R,24S)-[1,3-bis [[dimethyl(1,1-dimethylethyl)silyl]oxy]-24a,24a-difluoro-24-hydroxy-24a-homo-9,10-secochola-5,7,10 (19),22-tetraen-24a-yl]phosphonic acid diethyl ester 44a and 31 mg of (5Z,7E,22E)-(1S,3R,24R)-[1,3-bis [[dimethyl(1,1-dimethylethyl)silyl]oxy]-24a,24a-difluoro-24-hydroxy-24a-homo-9,10-secochola-5,7,10 (19),22-tetraen-24a-yl]phosphonic acid diethyl ester 44b accumulate as colorless foams.

$^1$H-NMR (300 MHz, CD$_2$Cl$_2$): 44a: δ=0.05 ppm (s, 12H); 0.54 (s, 3H); 0.86 (s, 18H); 1.03 (d, 3H); 1.33 (t, 6H); 3.05 (d, OH); 4.17 (m, 1H); 4.21 (m, 4H); 4.35 (m, 1H); 4.83 (s, 1H); 5.15 (s, 1H); 5.45 (dd, 1H); 5.78 (dd, 1H); 6.00 (d, 1H); 6.23 (d, 1H)

44b: δ=0.05 ppm (s, 12H); 0.54 (s, 3H); 0.86 (s, 18H); 105 (d, 3H); 1.33 (t, 6H); 3.04 (d, OH); 4.17 (m, 1H); 4.21 (m, 4H); 4.36 (m, 1H); 4.83 (s, 1H); 5.16 (s, 1H); 5.44 (dd, 1H); 5.74 (dd, 1H); 6.00 (d, 1H); 6.24 (d, 1H)

b) 33 mg of diastereomer 44a is treated analogously to 1d), and after chromatographic purification on silica gel with ethyl acetate/hexane, 18 mg of title compound 45a is obtained as a colorless foam.

$^1$H-NMR (300 MHz, CD$_2$Cl$_2$): δ=0.56 ppm (s, 3H); 1.05 (d, 3H); 1.35 (t, 6H); 3.02 (d, OH); 4.15 (m, 1H); 4.23 (q, 4H); 4.36 (m, 1H); 4.94 (s, 1H); 5.28 (s, 1H); 5.47 (dd, 1H); 5.80 (dd, 1H); 6.01 (d, 1H); 6.35 (d, 1H)

c) 30 mg of diastereomer 44b is treated analogously to 1d), and after chromatographic purification on silica gel with ethyl acetate/hexane, 16 mg of title compound 45b is obtained as a colorless foam.

$^1$H-NMR (300 MHz, CD$_2$Cl$_2$): δ=0.55 ppm (s, 3H); 1.05 (d, 3H); 1.35 (t, 6H); 3.10 (d, OH); 4.15 (m, 1H); 4.23 (q, 4H); 4.35 (m, 1H); 4.94 (s, 1H); 5.28 (s, 1H); 5.45 (dd, 1H); 5.74 (dd, 1H); 6.01 (d, 1H); 6.35 (d, 1H)

EXAMPLE 20

(5Z,7E,22E)-(1S,3R)-(24a,24a-Difluoro-1,3-dihydroxy-24-oxo-24a-homo-9,10-secochola-5,7,10 (19),22-tetraen-24a-yl)phosphonic acid diethyl ester 47 a) 25 mg of diastereomer mixture 44 is introduced into 2 ml of dichloromethane, and 80 mg of manganese dioxide is added. After 24 hours, it is filtered off, rewashed with dichloromethane and concentrated by evaporation. The residue is chromatographed on silica gel with ethyl acetate/hexane, whereby 10 mg of (5Z,7E,22E)-(1S,3R)-[1,3-bis[[dimethyl(1,1-dimethylethyl)silyl]oxy]-24a,24a-difluoro-24-oxo-24a-homo-9,10-secochola-5,7,10(19),22-tetraen-24a-yl]phosphonic acid diethyl ester 46 accumulates as a colorless foam.

$^1$H-NMR (300 MHz, CD$_2$Cl$_2$): 44a: δ=0.05 ppm (s, 12H); 0.54 (s, 3H); 0.85 (s, 18H); 1.06 (d, 3H); 1.33 (t, 6H); 4.16 (m, 1H); 4.23 (m, 4H); 4.36 (m, 1H); 4.83 (s, 1H); 6.00 (d, 1H); 6.25 (d, 1H); 6.50 (d, 1H); 7.12 (dd, 1H)

b) 10 mg of ketone 46 is treated analogously to 1d), and after chromatographic purification on silica gel with ethyl acetate/hexane, 4 mg of title compound 47 is obtained as a colorless foam.

$^1$H-NMR (300 MHz, CD$_2$Cl$_2$): δ=0.57 ppm (s, 3H); 1.08 (d, 3H); 1.33 (t, 6H); 4.15 (m, 1H); 4.23 (q, 4H); 4.37 (m, 1H); 4.93 (s, 1H); 5.28 (s, 1H); 6.00 (d, 1H); 6.33 (d, 1H); 6.49 (d, 1H); 7.10 (dd, 1H)

EXAMPLE 21

(5Z,7E,22E)-(1S,3R)-(26,27-Diethenyl-1,3-dihydroxy-24-oxo-24a-homo-9,10-secocholesta-5,7,10(19),22-tetraen-25-yl)phosphonic acid diethyl ester 50 a) 40 mg of sodium hydride (60% suspension in mineral oil) is introduced into 2 ml of THF, and 374 mg of ketophosphonate 8 in 1 ml of THF is added in drops at 0° C. After 30 minutes, 180 mg of allyl bromide is added, and it is stirred for three more hours at 40° C. It is quenched with sodium chloride solution, extracted with ethyl acetate, dried on sodium sulfate, and the solvent is removed. The residue is chromatographed on silica gel, whereby 198 mg of (5Z,7E,22E)-(1S,3R)-[1,3-bis[[dimethyl(1,1-dimethylethyl)silyl]oxy]-26,27-diethenyl-24-oxo-24a-homo-9,10-secocholesta-5,7,10(19),22-tetraen-25-yl]phosphonic acid diethyl ester 48 and 123 mg of (5Z,7E,22E)-(1S,3R,24ξ)-[1,3-bis[[dimethyl(1,1-dimethylethyl)silyl]oxy]-26-ethenyl-24-oxo-24a-homo-27-nor-9,10-secocholesta-5,7,10(19),22-tetraen-25-yl]phosphonic acid diethyl ester 49 accumulate as colorless foams.

$^1$H-NMR (300 MHz, CD$_2$Cl$_2$): 48: δ=0.05 ppm (s, 12H); 0.54 (s, 3H); 0.86 (s, 18H); 1.06 (d, 3H); 1.28 (t, 6H); 2.66 (d, 4H); 4.06 (q, 4H); 4.17 (m, 1H); 4.36 (m, 1H); 4.83 (s, 1H); 5.04 (d, 2H); 5.10 (d, 2H); 5.17 (s, 1H); 5.77 (ddt, 2H); 6.00 (d, 1H); 6.23 (d, 1H); 6.65 (d, 1H); 6.73 (dd, 1H)

49: δ=0.05 ppm (s, 12H); 0.54 (s, 3H); 0.86 (s, 18H); 1.09 (d, 3H); 1.28 (t, 6H); 3.37 (m, 1H); 4.06 (q, 4H); 4.18 (m, 1H); 4.37 (m, 1H); 4.83 (s, 1H); 4.96 (d, 1H); 5.01 (d, 1H); 5.16 (s, 1H); 5.68 (m, 1H); 6.00 (d, 1H); 6.18 (d, 1H); 6.22 (d, 1H); 6.72 (dd, 1H)

b) 180 mg of phosphonic acid ester 48 is treated analogously to 1d), and after chromatographic purification of the crude product, 69 mg of title compound 50 is obtained as a colorless foam.

$^1$H-NMR (300 MHz, CD$_2$Cl$_2$): δ=0.57 ppm (s, 3H); 1.10 (d, 3H); 1.29 (t, 6H); 2.69 (dd, 4H); 4.10 (q, 4H); 4.18 (m, 1H); 4.37 (m, 1H); 4.93 (s, 1H); 5.05 (d, 2H); 5.10 (d, 2H); 5.28 (s, 1H); 5.79 (m, 2H); 6.01 (d, 1H); 6.36 (d, 1H); 6.69 (d, 1H); 6.78 (dd, 1H)

EXAMPLE 22

(5Z,7E,22E)-(1S,3R,24ξ)-(1,3-Dihydroxy-26-ethenyl-24-oxo-24a-homo-27-nor-9,10-secocholesta-5,7,10(19),22-tetraen-25-yl)phosphonic acid diethyl ester 51

39 mg of diastereomer mixture 49 is treated analogously to 1d), and after chromatographic purification of the crude product, 17 mg of title compound 51 is obtained as a colorless foam.

$^1$H-NMR (300 MHz, CD$_2$Cl$_2$): δ=0.57 ppm (s, 3H); 1.10 (d, 3H); 1.26 (t, 6H); 3.40 (m, 1H); 4.07 (q, 4H); 4.16 (m, 1H); 4.36 (m, 1H); 4.93 (s, 1H); 4.97 (d, 1H); 5.03 (d, 1H); 5.28 (s, 1H); 5.68 (m, 1H); 6.00 (d, 1H); 6.22 (d, 1H); 6.35 (d, 1H); 6.75 (dd, 1H)

EXAMPLE 23

(5Z,7E,22E)-(1S,3R)-(1,3-Dihydroxy-24-oxo-9,10-secocholesta-5,7,10(19),22-tetraen-25-yl)phosphonic acid diethyl ester 53 a) 25 mg of sodium hydride (60% suspension in mineral oil) is introduced into 2 ml of THF, and 187 mg of ketophosphonate 8 in 1 ml of THF is added in drops at 0° C. After 30 minutes, 0.12 ml of methyl iodide is added, and it is stirred for two more hours at 40° C. It is quenched with sodium chloride solution, extracted with ethyl acetate, dried on sodium sulfate, and the solvent is removed. The residue is chromatographed on silica gel, whereby 134 mg of (5Z,7E,22E)-(1S,3R)-[1,3-bis[[dimethyl(1,1-dimethylethyl)silyl]oxy]-24-oxo-9,10-secocholesta-5,7,10(19),22-tetraen-25-yl]phosphonic acid-diethyl ester 52 accumulates as a colorless foam.

$^1$H-NMR (300 MHz, CD$_2$Cl$_2$): δ=0.05 ppm (s, 12H); 0.54 (s, 3H); 0.87 (s, 18H); 1.07 (d, 3H); 1.28 (t, 6H); 1.34 (s, 3H); 1.38 (s, 3H); 4.06 (q, 4H); 4.17 (m, 1H); 4.37 (m, 1H); 4.83 (s, 1H); 5.18 (s, 1H); 6.00 (d, 1H); 6.24 (d, 1H); 6.65 (d, 1H); 6.74 (dd, 1H)

b) 120 mg of phosphonic acid ester 52 is treated analogously to 1d), and after chromatographic purification of the crude product, 65 mg of title compound 53 is obtained as a colorless foam.

$^1$H-NMR (300 MHz, CD$_2$Cl$_2$): δ=0.57 ppm (s, 3H); 1.10 (d, 3H); 1.30 (t, 6H); 1.33 (s, 3H); 1.38 (s, 3H); 3.40 (m, 1H); 4.09 (q, 4H); 4.18 (m, 1H); 4.38 (m, 1H); 4.95 (s, 1H); 4.97 (d, 1H); 5.28 (s, 1H); 6.00 (d, 1H); 6.32 (d, 1H); 6.68 (d, 1H); 6.75 (dd, 1H)

EXAMPLE 24

(5Z,7E,22E)-(1S,3R)-(1,3-Dihydroxy-26,27-dimethyl-24-oxo-9,10-secocholesta-5,7,10(19),22-tetraen-25-yl)phosphonic acid diethyl ester 57 a) 60 mg of sodium hydride (60% suspension in mineral oil) is introduced into 4 ml of THF, and 374 mg of ketophosphonate 8 in 2 ml of THF is added in drops at 0° C. After 30 minutes, 0.24 ml of ethyl iodide is added, and it is stirred for two more hours at 40° C. and for 12 more hours at room temperature. It is quenched with sodium chloride solution, extracted with ethyl acetate, dried on sodium sulfate, and the solvent is removed. The residue is chromatographed on silica gel, whereby 66 mg of (5Z,7E,22E)-(1S,3R)-[1,3-bis[[dimethyl(1,1-dimethylethyl)silyl]oxy]-26,27-dimethyl-24-oxo-9,10-secocholesta-5,7,10(19),22-tetraen-25-yl]phosphonic acid diethyl ester 54, 45 mg of (5Z,7E,22E)-(1S,3R,25ξ)-[1,3-bis[[dimethyl(1,1-dimethylethyl)silyl]oxy]-26-methyl-24-oxo-27-nor-9,10-secocholesta-5,7,10(19),22-tetraen-25-yl]phosphonic acid diethyl ester 55, and 23 mg of (5Z,7E,22E,24Z)-(1S,3R)-[1,3-bis[[dimethyl(1,1-dimethylethyl)silyl]oxy]-24a-ethyl-24-ethoxy-9,10-secochola-5,7,10(19),22,24-pentaen-25-yl]phosphonic acid diethyl ester 56 are accumulated in succession as colorless foams.

$^1$H-NMR (300 MHz, CD$_2$Cl$_2$): 54: δ=0.05 ppm (s, 12H); 0.54 (s, 3H); 0.86 (s, 18H); 0.87 (t, 6H); 1.07 (d, 3H); 1.26 (t, 6H); 4.06 (q, 4H); 4.17 (m, 1H); 4.36 (m, 1H); 4.83 (s, 1H); 5.17 (s, 1H); 6.00 (d, 1H); 6.23 (d, 1H); 6.63 (d, 1H); 6.68 (dd, 1H)

55: δ=0.05 ppm (s, 12H); 0.54 (s, 3H); 0.86 (s, 18H); 0.87 (t, 3H); 1.07 (d, 3H); 1.27 (t, 6H); 3.16 (m, 1H); 4.05 (q, 4H); 4.17 (m, 1H); 4.37 (m, 1H); 4.83 (s, 1H); 5.17 (s, 1H); 6.00 (d, 1H); 6.22 (d, 1H); 6.23 (d, 1H); 6.73 (dddd, 1H)

56: δ=0.05 ppm (s, 12H); 0.54 (s, 3H); 0.86 (s, 18H); 1.00 (t, 3H); 1.07 (d, 3H); 1.26 (t, 9H); 3.80 (q, 2H); 4.03 (q, 4H); 4.17 (m, 1H); 4.36 (m, 1H); 4.83 (s, 1H); 5.17 (s, 1H); 5.98 (m, 2H); 6.00 (d, 1H); 6.23 (d, 1H)

b) 51 mg of phosphonic acid ester 54 is treated analogously to 1d), and after chromatographic purification of the crude product, 21 mg of title compound 57 is obtained as a colorless foam.

¹H-NMR (300 MHz, CD₂Cl₂): δ=0.57 ppm (s, 3H); 0.89 (t, 6H); 1.08 (d, 3H); 1.29 (t, 6H); 4.07 (q, 4H); 4.18 (m, 1H); 4.38 (m, 1H); 4.95 (s, 1H); 4.97 (d, 1H); 5.28 (s, 1H); 6.00 (d, 1H); 6.35 (d, 1H); 6.65 (d, 1H); 6.71 (dd, 1H)

EXAMPLE 25

(5Z,7E,22E)-(1S,3R,25R)-(1,3-Dihydroxy-26-methyl-24-oxo-27-nor-9,10-secocholesta-5,7,10(19), 22-tetraen-25-yl)phosphonic acid diethyl ester 58a and (5Z,7E,22E)-(1S,3R,25S)-(1,3-dihydroxy-26-methyl-24-oxo-27-nor-9,10-secocholesta-5,7,10(19), 22-tetraen-25-yl)phosphonic acid diethyl ester 58b 78 mg of diastereomer mixture 55 is treated analogously to 1d), and after chromatographic purification of the crude product (HPLC), 20 mg of title compound 58a and 18 mg of title compound 58b are obtained as colorless foams.

¹H-NMR (300 MHz, CD₂Cl₂): 58a: δ=0.56 ppm (s, 3H); 0.86 (t, 6H); 1.08 (d, 3H); 1.29 (t, 6H); 3.65 (m, 1H); 4.06 (q, 4H); 4.15 (m, 1H); 4.36 (m, 1H); 4.95 (s, 1H); 5.28 (s, 1H); 6.00 (d, 1H); 6.20 (d, 1H); 6.32 (d, 1H); 6.71 (dd, 1H)

58b: δ=0.56 ppm (s, 3H); 0.87 (t, 6H); 1.08 (d, 3H); 1.30 (t, 6H); 3.65 (m, 1H); 4.06 (q, 4H); 4.15 (m, 1H); 4.36 (m, 1H); 4.95 (s, 1H); 5.28 (s, 1H); 6.00 (d, 1H); 6.20 (d, 1H); 6.33 (d, 1H); 6.72 (dd, 1H)

EXAMPLE 26

(5Z,7E,22E,24Z)-(1S,3R)-(1,3-Dihydroxy-24a-ethyl-24-ethoxy-9,10-secochola-5,7,10(19),22,24-pentaen-25-yl)phosphonic acid diethyl ester 59

19 mg of phosphonic acid ester 56 is dissolved in 5 ml of THF, and 52 mg of tetrabutylammonium fluoride (hydrate) is added. It is stirred for 12 hours at room temperature and then quenched with sodium chloride solution. It is extracted with ethyl acetate, the organic phase is washed with sodium chloride solution, dried on sodium sulfate, and concentrated by evaporation. The residue is purified by chromatography of the crude product on silica gel with ethyl acetate/hexane, whereby 10 mg of title compound 59 accumulates as a colorless foam.

¹H-NMR (300 MHz, CD₂Cl₂): δ=0.58 ppm (s, 3H); 1.03 (t, 3H); 1.09 (d, 3H); 1.31 (t, 9H); 3.80 (q, 2H); 4.05 (q, 4H); 4.16 (m, 1H); 4.37 (m, 1H); 4.95 (s, 1H); 5.28 (s, 1H); 5.99 (m, 2H); 6.00 (d, 1H); 6.33 (d, 1H)

EXAMPLE 27

(5Z,7E,22E)-(1S,3R,24S)-(1,3,24-Trihydroxy-9,10-secochola-5,7,10(19),22-tetraen-24-yl)phosphonic acid dimethyl ester 61a and (5Z,7E,22E)-(1S,3R, 24R)-(1,3,24-trihydroxy-9,10-secochola-5,7,10(19), 22-tetraen-24-yl)phosphonic acid dimethyl ester 61b a) 0.07 ml of dimethylphosphite is introduced into 3 ml of THF, and it is cooled to −78° C. At this temperature, 0.3 ml of n-butyllithium solution (1.6 M in hexane) is added in drops, and it is stirred for 15 more minutes. Then, 300 mg of aldehyde 18 in 2 ml of THF is added, and it is stirred for 1.5 hours at 0° C. Then, it is quenched with sodium chloride solution, extracted with ethyl acetate, dried on sodium sulfate, and the solvent is removed. The residue is chromatographed on silica gel with ethyl acetate/hexane, whereby 267 mg of (5Z,7E,22E)-(1S,3R, 24ξ)-[1,3-bis[[dimethyl(1,1-dimethylethyl)silyl]oxy]-24-hydroxy-9,10-secochola-5,7,10(19),22-tetraen-24-yl) phosphonic acid-dimethyl ester 60 is obtained as a colorless foam.

¹H-NMR (300 MHz, CDCl₃): δ=0.08 ppm (s, 12H); 0.56 (s, 3H); 0.88 (s, 18H); 1.07/1.08 (d, 3H); 3.80 (s, 3H); 3.84 (s, 3H); 4.20 (m, 1H); 4.37 (m, 1H); 4.39 (m, 1H); 4.88 (s, 1H); 5.18 (s, 1H); 5.53 (m, 1H); 5.73 (m, 1H); 6.00 (d, 1H); 6.24 (d, 1H)

b) 151 mg of phosphonic acid ester 60 is treated analogously to 1d), and after chromatographic purification of the crude product (HPLC), 39 mg of title compound 61a and 43 mg of title compound 61b are obtained as colorless foams.

¹H-NMR (300 MHz, CD₂Cl₂): 61a: δ=0.55 ppm (s, 3H); 1.05 (d, 3H); 3.73 (d, 3H); 3.74 (d, 3H); 4.15 (m, 1H); 4.38 (m, 2H); 4.93 (s, 1H); 5.28 (s, 1H); 5.48 (ddd, 1H): 5.73 (ddd, 1H); 6.00 (d, 1H); 6.35 (d, 1H)

61a: δ=0.55 ppm (s, 3H); 1.05 (d, 3H); 3.74 (d, 3H); 3.75 (d, 3H); 4.15 (m, 1H); 4.37 (m, 2H); 4.93 (s, 1H); 5.28 (s, 1H); 5.47 (ddd, 1H); 5.71 (ddd, 1H); 6.00 (d, 1H); 6.35 (d, 1H)

EXAMPLE 28

(5Z,7E,22E)-(1S,3R,24S)-(1,3,24-Trihydroxy-9,10-secochola-5,7,10(19),22-tetraen-24-yl)phosphonic acid diethyl ester 63a and (5Z,7E,22E)-(1S,3R, 24R)-(1,3,24-trihydroxy-9,10-secochola-5,7,10(19), 22-tetraen-24-yl)phosphonic acid diethyl ester 63b a) 0.1 ml of diethylphosphite is introduced into 3 ml of THF and cooled to −78° C. At this temperature, 0.3 ml of n-butyllithium solution (1.6 M in hexane) is added in drops, and it is stirred for 15 more minutes. Then, 300 mg of aldehyde 18 is added to 2 ml of THF, and it is stirred for 1.5 hours at 0° C. Then, it is quenched with sodium chloride solution, extracted with ethyl acetate, dried on sodium sulfate, and the solvent is removed. The residue is chromatographed on silica gel with ethyl acetate/hexane, whereby 234 mg of (5Z,7E,22E)-(1S,3R,24ξ)-[1,3-bis [[dimethyl(1,1-dimethylethyl)silyl]oxy]-24-hydroxy-9, 10-secochola-5,7,10(19),22-tetraen-24-yl)phosphonic acid diethyl ester 62 is obtained as a colorless foam.

¹H-NMR (300 MHz, CDCl₃): δ=0.08 ppm (s, 12H); 0.53 (s, 3H); 0.88 (s, 18H); 1.05/1.06 (d, 3H); 1.31 (t, 6H); 4.18 (m, 5H); 4.37 (m, 2H); 4.86 (s, 1H); 5.18 (s, 1H); 5.50 (m, 1H); 5.71 (m, 1H); 6.00 (d, 1H); 6.23 (d, 1H)

b) 135 mg of phosphonic acid ester 62 is treated analogously to 1d), and after chromatographic purification of the crude product (HPLC), 32 mg of title compound 63a and 36 mg of title compound 63b are obtained as colorless foams.

¹H-NMR (300 MHz, CD₂Cl₂): 63a: δ=0.55 ppm (s, 3H); 1.05 (d, 3H); 1.29 (t, 3H); 4.15 (m, 5H); 4.33 (m, 1H); 4.36 (m, 1H); 4.93 (s, 1H); 5.28 (s, 1H); 5.45 (ddd, 1H); 5.71 (ddd, 1H); 6.00 (d, 1H); 6.35 (d, 1H)

63a: δ=0.55 ppm (s, 3H); 1.05 (d, 3H); 1.28 (t, 3H); 4.14 (m, 5H); 4.30 (m, 1H); 4.35 (m, 1H); 4.93 (s, 1H); 5.28 (s, 1H); 5.44 (ddd, 1H); 5.69 (ddd, 1H); 6.00 (d, 1H); 6.35 (d, 1H)

EXAMPLE 29

(5Z,7E,22E)-(1S,3R,24S)-(1,3,24-Trihydroxy-9,10-secochola-5,7,10(19),22-tetraen-24-yl)phosphonic acid-bis(1-methylethyl)ester 65a and (5Z,7E,22E)-(1S,3R,24R)-(1,3,24-trihydroxy-9,10-secochola-5,7, 10(19),22-tetraen-24-yl)phosphonic acid-bis(1-methylethyl)ester 65b a) 0.13 ml of diisopropylphosphite is introduced into 3 ml of THF and cooled to −78° C. At this temperature, 0.3 ml of n-butyllithium solution (1.6 M in hexane) is added in drops, and it is stirred for 15 more minutes. Then, 300 mg of aldehyde 18 in 2 ml of THF is added, and it is stirred for 1.5 hours at 0° C. Then, it is quenched with sodium chloride solution, extracted with ethyl acetate, dried on sodium sulfate, and the solvent is removed. The residue is chromatographed on silica gel with ethyl acetate/hexane, whereby 248 mg of (5Z,7E,22E)-(1S,3R,24ξ)-[1,3-bis[[dimethyl(1,1-dimethylethyl)silyl]oxy]-24-hydroxy-9,10-secochola-5,7,10(19),22-tetraen-24-yl)phosphonic acid-bis(1-methylethyl)ester 64 is obtained as a colorless foam.

$^1$H-NMR (300 MHz, CDCl$_3$): δ=0.08 ppm (s, 12H); 0.56 (s, 3H); 0.89 (s, 18H); 1.05/1.06 (d, 3H); 1.36 (d, 12H); 4.19 (m, 1H); 4.32 (m, 1H); 4.37 (m, 1H); 4.72 (hept, 2H); 4.86 (s, 1H); 5.19 (s, 1H); 5.50 (m, 1H); 5.70 (m, 1H); 6.00 (d, 1H); 6.23 (d, 1H)

b) 158 mg of phosphonic acid ester 64 is treated analogously to 1d), and after chromatographic purification of the crude product (HPLC), 28 mg of title compound 65a and 31 mg of title compound 65b are obtained as colorless foams.

$^1$H-NMR (300 MHz, CD$_2$Cl$_2$): 65a: δ=0.54 ppm (s, 3H); 1.05 (d, 3H); 1.30 (d, 12H); 4.15 (m, 1H); 4.24 (m, 1H); 4.35 (m, 1H); 4.62 (hept, 2H); 4.93 (s, 1H); 5.28 (s, 1H); 5.45 (ddd, 1H); 5.68 (ddd, 1H); 6.00 (d, 1H); 6.35 (d, 1H)

65b: δ=0.54 ppm (s, 3H); 1.04 (d, 3H); 1.30 (d, 12H); 4.15 (m, 1H); 4.23 (m, 1H); 4.35 (m, 1H); 4.64 (hept, 2H); 4.93 (s, 1H); 5.28 (s, 1H); 5.44 (ddd, 1H); 5.66 (ddd, 1H); 6.00 (d, 1H); 6.35 (d, 1H)

EXAMPLE 30

(5Z,7E,22E)-(1S,3R)-(1,3-Dihydroxy-24-oxo-9,10-secochola-5,7,10(19),22-tetraen-24-yl)phosphonic acid-bis(1-methylethyl)ester 67 a) 0.04 ml of oxalyl chloride is introduced into 8 ml of dichloromethane, and it is cooled to −60° C. 0.06 ml of dimethyl sulfoxide is then added in drops, and it is stirred for two more minutes. Then, 91 mg of diastereomer mixture 64 in 1.5 ml of dichloromethane is added, it is stirred for 30 minutes at −50° C., and then 0.27 ml of triethylamine is added. After 20 minutes at room temperature, it is quenched with sodium chloride solution, extracted with ethyl acetate, dried on sodium sulfate, and the solvent is removed. The residue is chromatographed on silica gel with ethyl acetate/hexane, whereby 71 mg of (5Z,7E,22E)-(1S,3R)-[1,3-bis[[dimethyl(1,1-dimethylethyl)silyl]oxy]-24-oxo-9,10-secochola-5,7,10(19),22-tetraen-24-yl]phosphonic acid-bis(1-methylethyl)ester 66 is obtained as a colorless foam.

$^1$H-NMR (300 MHz, CDCl$_3$): δ=0.08 ppm (s, 12H); 0.57 (s, 3H); 0.89 (s, 18H); 1.13 (d, 3H); 1.39 (d, 12H); 4.20 (m, 1H); 4.38 (m, 1H); 4.79 (hept, 2H); 4.86 (s, 1H); 5.19 (s, 1H); 5.50 (m, 1H); 5.70 (m, 1H); 6.01 (d, 1H); 6.23 (d, 1H); 6.39 (dd, 1H); 7.34 (dd, 1H)

b) 56 mg of phosphonic acid ester 66 is dissolved in 1 ml of acetonitrile and 1 ml of THF, and 0.1 ml of hydrogen fluoride (50% aqueous solution) is added at room temperature. It is stirred for 1 hour at room temperature and then quenched with sodium bicarbonate, extracted with ethyl acetate, dried on sodium sulfate, and the solvent is removed. The residue is chromatographed on silica gel with ethyl acetate/hexane, whereby 19 mg of title compound 67 accumulates as a colorless foam.

$^1$H-NMR (300 MHz, CD$_2$Cl$_2$): δ=0.57 ppm (s, 3H); 1.11 (d, 3H); 1.35 (d, 12H); 4.17 (m, 1H); 4.36 (m, 1H); 4.70 (hept, 2H); 4.93 (s, 1H); 5.28 (s, 1H); 6.01 (d, 1H); 6.30 (d, 1H); 6.35 (d, 1H); 7.30 (d, 1H)

EXAMPLE 31

(5Z,7E,22E)-(1S,3S)-(1,3-Dihydroxy-24-oxo-24a-homo-9,10-secochola-5,7,10(19),22-tetraen-24a-yl) phosphonic acid diethyl ester 78 a) 28.2 g of (5E,7E,22E)-(1S,3R)-[3-[dimethyl(1,1-dimethylethyl)silyl]oxy]-9,10-secoergosta-5,7,10(19),22-tetraen-1-ol 68 [M. J. Calverley Tetrahedron 43, 4609 (1987)] is introduced into 270 ml of pyridine, and it is cooled to 0° C. 54 ml of acetic anhydride is added in drops to it, and it is stirred for 12 more hours. It is quenched with sodium chloride solution, extracted with ethyl acetate, washed with dilute hydrochloric acid and sodium chloride solution, dried on sodium sulfate and concentrated by evaporation. The residue is chromatographed on silica gel with ethyl acetate/hexane, whereby 27.0 g of (5Z,7E,22E)-(1S,3R)-1-(acetyloxy)-[3-[dimethyl(1,1-dimethylethyl)silyl]oxy]-9,10-secoergosta-5,7,10(19),22-tetraene 69 accumulates as a colorless foam.

$^1$H-NMR (300 MHz, CDCl$_3$): δ=0.08 ppm (s, 6H); 0.57 (s, 3H); 0.83 (d, 3H); 0.84 (d, 3H); 0.90 (s, 3H); 0.96 (d, 3H); 1.03 (d, 3H); 2.06 (s, 3H); 4.14 (m, 1H); 4.93 (s, 1H); 5.17 (s, 1H); 5.20 (m, 2H); 5.60 (m, 1H); 5.88 (d, 1H); 6.51 (d, 1H)

b) 2.17 g of silyl ether 69 is dissolved in 100 ml of THF, and 2.47 g of tetrabutylammonium fluoride (hydrate) is added. It is stirred for 12 hours at room temperature and then mixed with sodium chloride solution, extracted with ethyl acetate, dried on sodium sulfate and concentrated by evaporation. The residue is chromatographed on silica gel with ethyl acetate/hexane, whereby 1.22 g of (5Z,7E,22E)-(1S,3R)-1-(acetyloxy)-9,10-secoergosta-5,7,10(19),22-tetraen-3-ol 70 accumulates as a colorless foam.

$^1$H-NMR (300 MHz, CDCl$_3$): δ=0.58 ppm (s, 3H); 0.83 (d, 3H); 0.84 (d, 3H); .92 (d, 3H); 1.02 (d, 3H); 2.04 (s, 3H); 4.16 (m, 1H); 5.00 (s, 1H); 5.20 (m, 3H); 5.57 (m, 1H); 5.88 (d, 1H); 6.53 (d, 1H)

c) 1.22 g of acetate 70 is dissolved in 35 ml of THF, and 1.41 g of triphenylphosphine and 939 mg of azodicarboxylic acid diethyl ester and 324 mg of acetic acid are added at room temperature. After 12 hours at room temperature, it is diluted with sodium chloride solution, extracted with ethyl acetate, the organic phase is washed with sodium chloride solution, dried on sodium sulfate, and the solvent is removed. The residue is chromatographed on silica gel with ethyl acetate/hexane, whereby 845 mg of (5Z,7E,22E)-(1S,3S)-1,3-bis(acetyloxy)-9,10-secoergosta-5,7,10(19),22-tetraene 71 accumulates as a colorless foam.

$^1$H-NMR (300 MHz, CDCl$_3$): δ=0.58 ppm (s, 3H); 0.83 (d, 3H); 0.84 (d, 3H); 0.93 (d, 3H); 1.03 (d, 3H); 2.06 (s, 3H); 2.07 (s, 3H); 4.85 (s, 1H); 4.95 (m, 1H); 5.13 (s, 1H); 5.21 (m, 2H); 5.38 (m, 1H); 5.82 (d, 1H); 6.61 (d, 1H)

d) 2.1 g of diacetate 71 is dissolved in 100 ml of methanol, and 120 ml of sodium carbonate solution (10% in water) is added. After 12 hours at room temperature, sodium chloride solution is added, it is extracted with ethyl acetate, the organic phase is dried on sodium sulfate, the solvent is removed, and the residue is chromatographed on silica gel with ethyl acetate/hexane, whereby 1.36 g of (5Z,7E,22E)-(1S,3S)-9,10-secoergosta-5,7,10(19),22-tetraene-1,3-diol 72 accumulates as a colorless foam.

$^1$H-NMR (300 MHz, CDCl$_3$): δ=0.60 ppm (s, 3H); 0.83 (d, 3H); 0.84 (d, 3H); 0.93 (d, 3H); 1.04 (d, 3H); 4.15 (m, 1H); 4.39 (m, 1H); 4.98 (s, 1H); 5.13 (s, 1H); 5.21 (m, 2H); 5.91 (d, 1H); 6.64 (d, 1H)

e) 1.36 g of diol 72 is dissolved in 30 ml of dimethylformamide (DMF), and 1.79 g of imidazole as well as 44 ml of tert-butyl dimethyl silyl chloride are added. It is stirred for 12 hours at room temperature, and then sodium chloride solution is added, extracted with ethyl acetate, the organic phase is dried on sodium sulfate, the solvent is removed, and the residue is chromatographed on silica gel with ethyl acetate/hexane, whereby 1.50 g of (5E,7E,22E)-(1S,3S)-1,3-bis[[dimethyl(1,1-dimethylethyl)silyl]oxy]-9,10-secoergosta-5,7,10(19),22-tetraene 73 accumulates as a colorless foam.

$^1$H-NMR (300 MHz, CDCl$_3$): δ=0.08 ppm (s, 12H); 0.57 (s, 3H); 0.83 (d, 3H); 0.84 (d, 3H); 0.93 (d, 3H); 0.90 (s, 9H); 0.90 (d, 3H); 0.91 (s, 9H); 1.02 (d, 3H); 3.70 (m, 1H); 4.10 (m, 1H); 5.00 (s, 1H); 5.02 (s, 1H); 5.20 (m, 2H); 5.82 (d, 1H); 6.48 (d, 1H)

f) 30 ml of sulfur dioxide is condensed at −40° C., and 5 g of disilyl ether 73 is added in drops to 30 ml of diethyl ether. Then, excess sulfur dioxide is allowed to evaporate, and the solvent is removed. The residue is dissolved in 120 ml of dichloromethane and 60 ml of methanol and cooled to −78° C. For 22 minutes, an oxygen/ozone mixture (30 l/h) is now run through. 2.09 g of triphenylphosphine is added to it, and it is stirred for 30 more minutes. After 150 ml of sodium bicarbonate solution (5% in water) is added, it is allowed to come to room temperature, the organic phase is separated and concentrated by evaporation. The crude product (5.1 g) is dissolved in 100 ml of ethanol, 6.7 g of sodium bicarbonate is added, and it is heated to boiling for one hour. The reaction mixture is poured into water, extracted with ethyl acetate, the organic phase is dried on sodium sulfate, and the solvent is removed. The residue is chromatographed on silica gel with ethyl acetate/hexane, and 3.1 g of (5E,7E)-(1S,3S)-1,3-bis[[dimethyl(1,1-dimethylethyl)silyl]oxy]-9,10-secopregna-5,7,10(19)triene-20-carbaldehyde 74 is obtained as a colorless foam.

$^1$H-NMR (300 MHz, CDCl$_3$): δ=0.08 ppm (s, 12H); 0.60 (s, 3H); 0.90 (s, 9H); 0.92 (s, 9H); 1.13 (d, 3H); 3.70 (m, 1H); 4.10 (m, 1H); 5.01 (s, 1H); 5.04 (s, 1H); 5.83 (d, 1H); 6.47 (d, 1H)

g) 1.5 g of aldehyde 74 is dissolved in 600 ml of toluene, and 200 mg of anthracene and 4 drops of triethylamine are added, and it is irradiated with a high-pressure mercury-vapor lamp in a photoreactor made of Duranglas for 10 minutes. Then, the solvent is removed, and the residue is chromatographed on silica gel with ethyl acetate/hexane, whereby 1.45 g of (5Z,7E)-(1S,3S)-1,3-bis[[dimethyl(1,1-dimethylethyl)silyl]oxy]-9,10-secopregna-5,7,10(19)-triene-20-carbaldehyde 75 accumulated as a colorless foam.

$^1$H-NMR (300 MHz, CDCl$_3$): δ=0.08 ppm (s, 12H); 0.60 (s, 3H); 0.90 (s, 9H); 0.94 (s, 9H); 1.13 (d, 3H); 3.70 (m, 1H); 3.95 (m, 1H); 4.92 (s, 1H); 5.38 (s, 1H); 6.00 (d, 1H); 6.37 (d, 1H); 9.58 (d, 1H)

h) 250 mg of sodium hydride (60% in mineral oil) is introduced into 32 ml of THF, and 1.24 g of dimethylphosphonoacetate in 32 ml of THF is added in drops. It is stirred for one hour at room temperature, and then 1.3 g of aldehyde 75 in 32 ml of THF is added. After 12 hours, it is diluted with ethyl acetate, water is added, and it is extracted with ethyl acetate. The organic phase is washed with sodium chloride solution, dried on sodium sulfate, and concentrated by evaporation. The residue is chromatographed on silica gel with ethyl acetate/hexane, whereby 234 mg of (5Z,7E,22E)-(1S,3S)-1,3-bis[[dimethyl(1,1-dimethylethyl)silyl]oxy]-9,10-secochola-5,7,10(19),22-tetraenoic-24-acid methyl ester 76 accumulates as a colorless foam.

$^1$H-NMR (300 MHz, CDCl$_3$): δ=0.08 ppm (s, 12H); 0.58 (s, 3H); 0.90 (s, 9H); 0.93 (s, 9H); 1.10 (d, 3H); 3.68 (m, 1H); 3.71 (s, 3H); 3.95 (m, 1H); 4.92 (s, 1H); 5.38 (s, 1H); 5.73 (d, 1H); 6.00 (d, 1H); 6.27 (d, 1H); 6.84 (dd, 1H)

i) 760 mg of diethylmethylphosphonate is introduced into 20 ml of THF and cooled to −78° C. At this temperature, 3.1 ml of an n-butyllithium solution (1.6 M in hexane) is added in drops, and it is stirred for 30 minutes. Then, 700 mg of carboxylic acid ester 76 in 3 ml of THF is added, and it is stirred for one more hour. It is quenched with sodium chloride solution, extracted with ethyl acetate, the organic phase is washed with sodium chloride solution and dried on sodium sulfate. The residue is chromatographed on silica gel with ethyl acetate/hexane, whereby 704 mg of (5Z,7E,22E)-(1S,3S)-[1,3-bis[[dimethyl(1,1-dimethylethyl)silyl]oxy]-24-oxo-24a-homo-9,10-secochola-5,7,10(19),22-tetraen-24a-yl]phosphonic acid diethyl ester 77 accumulates as a colorless foam.

$^1$H-NMR (300 MHz, CDCl$_3$): δ=0.08 ppm (s, 12H); 0.59 (s, 3H); 0.89 (s, 9H); 0.94 (s, 9H); 1.12 (d, 3H); 1.30 (t, 6H); 3.20 (d, 2H); 3.70 (m, 1H); 3.95 (m, 1H); 4.14 (q, 4H); 4.92 (s, 1H); 5.39 (s, 1H); 6.00 (d, 1H); 6.18 (d, 1H); 6.28 (d, 1H); 6.82 (dd, 1h)

j) 60 mg of phosphonic acid ester 77 is treated analogously to 1d), and 26 mg of title compound 78 is obtained as a colorless foam.

$^1$H-NMR (300 MHz, CDCl$_3$): δ=0.60 ppm (s, 3H); 1.12 (d, 3H); 1.32 (t, 6H); 3.20 (d, 2H); 4.08 (m, 1H); 4.15 (q, 4H); 4.32 (m, 1H); 4.98 (s, 1H); 5.30 (s, 1H); 6.01 (d, 1H); 6.18 (d, 1H); 6.33 (d, 1H); 6.82 (dd, 1H)

What is claimed is:

1. A Vitamin D derivative compound of formula I:

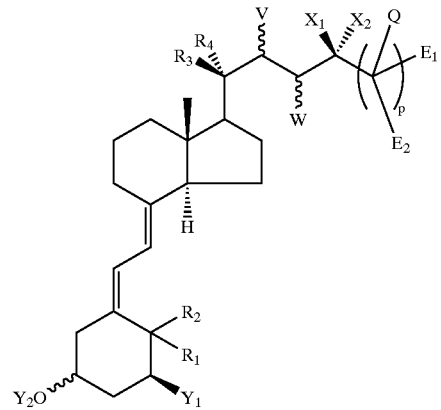

in which

Y$_1$ means a hydrogen atom, a hydroxyl group, a fluorine, chlorine or bromine atom or a group —O(CO)R$_5$, in which R$_5$ is an aliphatic or aromatic radical with 1 to 12 C atoms, Y$_2$ means a hydrogen atom or a group —(CO)R$_6$, in which R$_6$ is an aliphatic or aromatic radical with 1 to 12 C atoms, and group Y$_2$O can be present both in the naturally occurring situation (3β) and in the epimeric situation (3α), R$_1$ and R$_2$ each mean a hydrogen atom or together an exocyclic methylene group, $R_3$ and $R_4$ independently of one another, mean a hydrogen atom, a chlorine or fluorine atom, an alkyl group with 1 to 4 carbon atoms, together a methylene group or together with the quaternary carbon atom to which they are bonded, a 3- to 7-membered, saturated or unsaturated carbocyclic ring, V and W together mean an E-double bond $X_1$ and $X_2$, independently of one another, mean a hydrogen atom, a hydroxyl group, a group —$OR_7$ or —$O(CO)R_7$, in which $R_7$ is an aliphatic or aromatic radical with 1 to 12 C atoms, or a group $PO(OR_8)_2$, a group $PO(N(R_8)_2)_2$, a group $PO(R_8)_2$, a group $OPO(OR_8)_2$, a group $OPO(N(R_8)_2)_2$, a group $OPO(R_8)_2$, a group $CH_2$—$PO(OR_8)_2$, a group $CH_2$—$PO(N(R_8)_2)_2$ or a group $CH_2$—$PO(R_8)_2$, in which $R_8$, independently of one another, are a hydrogen atom or an aliphatic or aromatic radical with 1 to 12 C atoms, or $X_1$ and $X_2$ together stand for a carbonyl group, p means the number 1 or 0, $E_1$ means a group $PO(OR_9)_2$, a group $PO(N(R_9)_2)_2$, or a group $PO(R_9)_2$, in which $R_9$ independently of one another, are a hydrogen atom or an aliphatic or aromatic radical with 1 to 12 C atoms, $E_2$ means a group $PO(OR_9)_2$, a group $PO(N(R_9)_2)_2$, a group $PO(R_9)_2$, a halogen atom (fluorine, chlorine, bromine), an aliphatic or aromatic radical with 1 to 12 C atoms or a hydrogen atom, Q means a hydrogen atom, an aliphatic or aromatic radical with 1 to 12 C atoms, a hydroxyl group, a group —$O(CO)R_{10}$, a fluorine, chlorine, or bromine atom, an amino group or an $NHR_{10}$ or $N(R_{10})_2$ group, in which $R_{10}$ is an aliphatic or aromatic radical with 1 to 12 C atoms, or $X_1$ and $E_2$ together mean a double bond and at the same time $X_2$ means a hydrogen atom or group O—Z, in which Z means an aliphatic or aromatic radical with 1 to 12 C atoms, an aliphatic or aromatic acyl group with 1 to 12 C atoms or a group $E_2$, or $X_1$, $X_2$, $E_2$ and Q together mean a triple bond.

2. Compound of general formula I according to claim 1, characterized in that $E_1$ and $E_2$ stand for phosphonic acid derivatives.

3. Compound of general formula I according to claim 1, wherein p stands for the number 1.

4. Compound of general formula I according to claim 1, wherein p stands for the number 0.

5. Compound of general formula I according to claim 1, characterized by one of the following combinations for $R_3$ and $R_4$:

$R_3$=H and $R_4$=methyl or $R_3$=methyl and $R_4$=H or $R_3$=F and $R_4$=methyl or $R_3$=methyl and $R_4$=F or $R_3$=methyl and $R_4$=methyl or $R_3$ and $R_4$ together form a methylene group or $R_3$ and $R_4$ together with tertiary carbon atom 20 form a cyclopropyl ring.

6. Compound of general formula I according to claim 1, wherein V and W and $X_1$ and $E_2$ in each case mean an E-double bond, and $X_2$ and Q are hydrogen atoms.

7. Compound of general formula I according to claim 1, wherein V and W together mean an E-double bond, $X_1$ and $E_2$ form an E- or Z-double bond, $X_2$ is a group —OZ, and Q means a hydrogen atom.

8. Compound of general formula I according to claim 1, wherein $X_1$, $X_2$, $E_2$, and Q together mean a triple bond.

9. Compound of general formula I according to claim 1, wherein $E_2$ and Q mean halogen atoms.

10. Compounds of general formula I according to claim 1, wherein $Y_1$ means a hydroxyl group or —$O(CO)R_5$, and $Y_2$ means a hydrogen atom or —$(CO)R_6$.

11. Compounds of general formula I, namely:

(5Z,7E,22E)-(1S,3R)-(1,3-Dihydroxy-24-oxo-24a-homo-9,10-secochola-5,7,10(19),22-tetraen-24a-yl)phosphonic acid dimethyl ester (5Z,7E,22E)-(1S,3R,24S)-(1,3,24-Trihydroxy-24a-homo-9,10-secochola-5,7,10(19),22-tetraen-24a-yl)phosphonic acid dimethyl ester (5Z,7E,22E)-(1S,3R,24R)-(1,3,24-Trihydroxy-24a-homo-9,10-secochola-5,7,10(19),22-tetraen-24a-yl)phosphonic acid dimethyl ester (5Z,7E,22E)-(1S,3R)-(1,3-Dihydroxy-24-oxo-24a-homo-9,10-secochola-5,7,10(19),22-tetraen-24a-yl)phosphonic acid diethyl ester (5Z,7E,22E)-(1S,3R,24S)-(1,3,24-Trihydroxy-24a-homo-9,10-secochola-5,7,10(19),22-tetraen-24a-yl)phosphonic acid diethyl ester (5Z,7E,22E)-(1S,3R,24R)-(1,3,24-Trihydroxy-24a-homo-9,10-secochola-5,7,10(19),22-tetraen-24a-yl)phosphonic acid diethyl ester (5Z,7E,22E)-(1S,3R)-(1,3-Dihydroxy-24-oxo-24a-homo-9,10-secochola-5,7,10(19),22-tetraen-24a-yl)phosphonic acid bis(1-methylethyl)ester (5Z,7E,22E)-(1S,3R,24S)-(1,3,24-Trihydroxy-24a-homo-9,10-secochola-5,7,10(19),22-tetraen-24a-yl)phosphonic acid bis(1-methylethyl)ester (5Z,7E,22E)-(1S,3R,24R)-(1,3,24-Trihydroxy-24a-homo-9,10-secochola-5,7,10(19),22-tetraen-24a-yl)phosphonic acid bis(1-methylethyl)ester (5Z,7E,22E)-(1S,3R)-(1,3-Dihydroxy-24-oxo-24a-homo-9,10-secochola-5,7,10(19),22-tetraen-24a-yl)phosphonic acid dipropyl ester (5Z,7E,22E)-(1S,3R,24S)-(1,3,24-Trihydroxy-24a-homo-9,10-secochola-5,7,10(19),22-tetraen-24a-yl)phosphonic acid dipropyl ester (5Z,7E,22E)-(1S,3R,24R)-(1,3,24-Trihydroxy-24a-homo-9,10-secochola-5,7,10(19),22-tetraen-24a-yl)phosphonic acid dipropyl ester (5Z,7E,22E)-(1S,3R)-(1,3-Dihydroxy-24-oxo-24a-homo-9,10-secochola-5,7,10(19),22-tetraen-24a-yl)phosphonic acid dibutyl ester (5Z,7E,22E)-(1S,3R,24S)-(1,3,24-Trihydroxy-24a-homo-9,10-secochola-5,7,10(19),22-tetraen-24a-yl)phosphonic acid dibutyl ester (5Z,7E,22E)-(1S,3R,24R)-(1,3,24-Trihydroxy-24a-homo-9,10-secochola-5,7,10(19),22-tetraen-24a-yl)phosphonic acid dibutyl ester (5Z,7E,22E)-(1S,3R)-(1,3-Dihydroxy-24-oxo-24a-homo-9,10-secochola-5,7,10(19),22-tetraen-24a-yl)phosphonic acid dipentyl ester (5Z,7E,22E)-(1S,3R,24S)-(1,3,24-Trihydroxy-24a-homo-9,10-secochola-5,7,10(19),22-tetraen-24a-yl)phosphonic acid dipentyl ester (5Z,7E,22E)-(1S,3R,24R)-(1,3,24-Trihydroxy-24a-homo-9,10-secochola-5,7,10(19),22-tetraen-24a-yl)phosphonic acid dipentyl ester (5Z,7E,22E)-(1S,3R)-(1,3-Dihydroxy-24-oxo-24a-homo-9,10-secochola-5,7,10(19),22-tetraen-24a-yl)phosphonic acid diphenyl ester (5Z,7E,22E)-(1S,3R,24S)-(1,3,24-Trihydroxy-24a-homo-9,10-secochola-5,7,10(19),22-tetraen-24a-yl)phosphonic acid diphenyl ester (5Z,7E,22E)-(1S,3R,24R)-(1,3,24-Trihydroxy-24a-homo-9,10-secochola-5,7,10(19),22-tetraen-24a-yl)phosphonic acid diphenyl ester (5Z,7E,22E)-(1S,3R)-(1,3-Dihydroxy-24-oxo-24a-homo-9,10-secochola-5,7,10(19),22-tetraene-24a,24a-diyl)bis[phosphonic acid dinethyl ester]

(5Z,7E 22E)-(1S,3R)-(1,3-Dihydroxy-24-oxo-24a-homo-9,10-secochola-5,7,10(19),22-tetraene-24a,24a-diyl)bis[phosphonic acid diethyl ester]

(5Z,7E,22E)-(1S,3R)-(1,3-Dihydroxy-24-oxo-24a-homo-9,10-secochola-5,7,10(19),22-tetraene-24a,24a-diyl)bis[phosphonic acid dipropyl ester]

(5Z,7E,22E)-(1S,3R)-(1,3-Dihydroxy-24-oxo-24a-homo-9,10-secochola-5,7,10(19),22-tetraene-24a,24a-diyl)bis[phosphonic acid dibutyl ester]

(5Z,7E,22E)-(1S,3R)-(1,3-Dihydroxy-24-oxo-24a-homo-9,10-secochola-5,7,10(19),22-tetraen-24a,24a-diyl)bis[phosphonic acid bis(1-methylethyl)ester]

(5Z,7E,22E)-(1S,3R)-(1,3-Dihydroxy-24-oxo-24a-homo-9,10-secochola-5,7,10(19),22-tetraene-24a,24a-diyl)bis[phosphonic acid diphenyl ester]

(5Z,7E,22E,24E)-(1S,3R)-(1,3-Dihydroxy -24a-homo-9,10-secochola-5,7,10(19),22,24-pentaen-24-yl)phosphonic acid dimethyl ester (5Z,7E,22E,24E)-(1S,3R)-(1,3-Dihydroxy-24a-homo-9,10-secochola-5,7,10(19),22,24-pentaen-24-yl)phosphonic acid diethyl ester (5Z,7E,22E,24E)-(1S,3R)-(1,3-Dihydroxy-24a-homo-9,10-secochola-5,7,10(19),22,24-pentaen-24-yl)phosphonic acid dipropyl ester (5Z,7E,22E,24E)-(1S,3R)-(1,3-Dihydroxy-24a-homo-9,10-secochola-5,7,10(19),22,24-pentaen-24-yl)phosphonic acid dibutyl ester (5Z,7E,22E,24E)-(1S,3R)-(1,3-Dihydroxy-24a-homo-9,10-secochola-5,7,10(19),22,24-pentaen-24-yl)phosphonic acid bis(1-methylethyl)ester (5Z,7E,22E)-(1S,3R)-24-(Diphenylphosphinyl)-9,10-secochola-5,7,10(19),22-tetraene-1,3-diol (5Z,7E,22E)-(1S,3R)-24-(Dimethylphosphinyl)-9,10-secochola-5,7,10(19),22-tetraene-1,3-diol (5Z,7E,22E)-(1S,3R)-24-(Diethylphosphinyl)-9,10-secochola-5,7,10(19),22-tetraene-1,3-diol (5Z,7E,22E)-(1S,3R)-24-(Dipropylphosphinyl)-9,10-secochola-5,7,10(19),22-tetraene-1,3-diol (5Z,7E,22E)-(1S,3R)-24-(Dibutylphosphinyl)-9,10-secochola-5,7,10(19),22-tetraene-1,3-diol (5Z,7E,22E,24E)-(1S,3R)-Phosphoric acid[1,3-dihydroxy-24a-(dimethoxy)phosphinyl-24a-homo-9,10-secochola-5,7,10(19),22,24-pentaen-24-yl]dimethyl ester (5Z,7E,22E,24Z)-(1S,3R)-Phosphoric acid[1,3-dihydroxy-24a-(dimethoxy)phosphinyl-24a-homo-9,10-secochola-5,7,10(19),22,24-pentaen-24-yl]dimethyl ester (5Z,7E,22E,24E)-(1S,3R)-Phosphoric acid[24a-(diethoxy)phosphinyl-1,3-dihydroxy-24a-homo-9,10-secochola-5,7,10(19),22,24-pentaen-24-yl]diethyl ester (5Z,7E,22E,24Z)-(1S,3R)-Phosphoric acid[24a-(diethoxy)phosphinyl-1,3-dihydroxy-24a-homo-9,10secochola-5,7,10(19),22,24-pentaen-24-yl]diethyl ester (5Z,7E,22E,24E)-(1S,3R)-Phosphoric acid[1,3-dihydroxy-24a-(dipropoxy)phosphinyl-24a-homo-9,10-secochola-5,7,10(19),22,24-pentaen-24-yl]dipropyl ester (5Z,7E,22E,24Z)-(1S,3R)-Phosphoric acid[1,3-dihydroxy-24a-(dipropoxy)phosphinyl-24a-homo-9,10-secochola-5,7,10(19),22,24-pentaen-24-yl]dipropyl ester (5Z,7E,22E,24E)-(1S,3R)-Phosphoric acid[24a-(dibutoxy)phosphinyl-1,3-dihydroxy-24a-homo-9,10secochola-5,7,10(19),22,24-pentaen-24-yl]dibutyl ester (5Z,7E,22E,24Z)-(1S,3R)-Phosphoric acid[24a-(dibutoxy)phosphinyl-1,3-dihydroxy-24a-homo-9,10secochola-5,7,10(19),22,24-pentaen-24-yl]dibutyl ester (5Z,7E,22E,24E)-(1S,3R)-Phosphoric acid[24a-[bis(1-methylethoxy)phosphinyl]-1,3-dihydroxy-24a-homo-9,10-secochola-5,7,10(19),22,24-pentaen-24-yl]bis(1-methylethyl)ester (5Z,7E,22E,24Z)-(1S,3R)-Phosphoric acid[24a-[bis(1-methylethoxy)phosphinyl]-1,3-dihydroxy-24a-homo-9,10-secochola-5,7,10(19),22,24-pentaen-24-yl]bis(1-methylethyl)ester (5Z,7E,22E)-(1S,3R)-(1,3-Dihydroxy-24-oxo-24a-homo-9,10-secochola-5,7,10(19),22-tetraen-24-yl)phosphonic acid-monomethyl ester (5Z,7E,22E)-(1S,3R)-(1,3-Dihydroxy-24-oxo-24a-homo-9,10-secochola-5,7,10(19),22-tetraen-24-yl)phosphonic acid-monoethyl ester (5Z,7E,22E)-(1S,3R)-(1,3-Dihydroxy-24-oxo-24a-homo-9,10-secochola-5,7,10(19),22-tetraen-24-yl)phosphonic acid-mono(1-methylethyl)ester (5Z,7E,22E)-(1S,3R)-(1,3-Dihydroxy-24-oxo-24a-homo-9,10-secochola-5,7,10(19),22-tetraen-24-yl)phosphonic acid-monopropyl ester (5Z,7E,22E)-(1S,3R)-(1,3-Dihydroxy-24-oxo-24a-homo-9,10-secochola-5,7,10(19),22-tetraen-24-yl)phosphonic acid-monobutyl ester (5Z,7E,22E)-(1S,3R)-(1,3-Dihydroxy-24-oxo-24a-homo-9,10-secochola-5,7,10(19),22-tetraen-24-yl)phosphonic acid (5Z,7E,22E,24E)-(1S,3R)-(1,3-Dihydroxy-24a-homo-9,10-secochola-5,7,10(19),22,24-pentaen-24-yl)phosphonic acid-monomethyl ester (5Z,7E,22E,24E)-(1S,3R)-(1,3-Dihydroxy-24a-homo-9,10-secochola-5,7,10(19),22,24-pentaen-24-yl)phosphonic acid-monoethyl ester (5Z,7E,22E,24E)-(1S,3R)-(1,3-Dihydroxy-24a-homo-9,10-secochola-5,7,10(19),22,24-pentaen-24-yl)phosphonic acid-mono(1-methylethyl)ester (5Z,7E,22E,24E)-(1S,3R)-(1,3-Dihydroxy-24a-homo-9,10-secochola-5,7,10(19),22,24-pentaen-24-yl)phosphonic acid-monopropyl ester (5Z,7E,22E,24E)-(1S,3R)-(1,3-Dihydroxy-24a-homo-9,10-secochola-5,7,10(19),22,24-pentaen-24-yl)phosphonic acid-monobutyl ester (5Z,7E,22E,24E)-(1S,3R)-(1,3-Dihydroxy-24a-homo-9,10-secochola-5,7,10(19),22,24-pentaen-24-yl)phosphonic acid (5Z,7E,22E)-(1S,3R,24ξ)-(1,3-Dihydroxy-24a-homo-9,10-secochola-5,7,10(19),22-tetraene-24,24a-diyl)bis[phosphonic acid dimethyl ester]

(5Z,7E,22E)-(1S,3R,24ξ)-(1,3-Dihydroxy-24a-homo-9,10-secochola-5,7,10(19),22-tetraene-24,24a-diyl)bis[phosphonic acid diethyl ester]

(5Z,7E,22E)-(1S,3R,24ξ)-(1,3-Dihydroxy-24a-homo-9,10-secochola-5,7,10(19),22-tetraene-24,24a-diyl)bis[phosphonic acid-bis(1-methylethyl)ester]

(5Z,7E,22E)-(1S,3R,24ξ)-(1,3-Dihydroxy-24a-homo-9,10-secochola-5,7,10(19),22-tetraene-24,24a-diyl)bis[phosphonic acid dipropyl ester]

(5Z,7E,22E)-(1S,3R,24ξ)-(1,3-Dihydroxy-24a-homo-9,10-secochola-5,7,10(19),22-tetraene-24,24a-diyl)bis[phosphonic acid dibutyl ester]

(5Z,7E,22E)-(1S,3R)-(1,3-Dihydroxy-24-nor-9,10-secocholesta-5,7,10(19),22-tetraene-26,27-diyl)bis [phosphonic acid dimethyl ester]

(5Z,7E,22E)-(1S,3R)-(1,3-Dihydroxy-24-nor-9,10-secocholesta-5,7,10(19),22-tetraene-26,27-diyl)bis [phosphonic acid diethyl ester]

(5Z,7E,22E)-(1S,3R)-(1,3-Dihydroxy-24-nor-9,10-secocholesta-5,7,10(19),22-tetraene-26,27-diyl)bis [phosphonic acid-bis(1-methylethyl)ester]

(5Z,7E,22E)-(1S,3R)-(1,3-Dihydroxy-24-nor-9,10-secocholesta-5,7,10(19),22-tetraene-26,27-diyl)bis [phosphonic acid dipropyl ester]

(5Z,7E,22E)-(1S,3R)-(1,3-Dihydroxy-24-nor-9,10-secocholesta-5,7,10(19),22-tetraene-26,27-diyl]bis [phosphonic acid dibutyl ester]

(5Z,7E,22E)-(1S,3R)-(1,3-Dihydroxy-24-nor-9,10-secocholesta-5,7,10(19),22-tetraene-26,27-diyl)bis [phosphonic acid]

(5Z,7E,22E,24E)-(1S,3R)-(1,3-Dihydroxy-24a-homo-9,10-secochola-5,7,10(19),22,24-pentaene-24a,24a-diyl)bis [phosphonic acid dimethyl ester]

(5Z,7E,22E,24E)-(1S,3R)-(1,3-Dihydroxy-24a-homo-9,10-secochola-5,7,10(19),22,24-pentaene-24a,24a-diyl)bis [phosphonic acid diethyl ester]

(5Z,7E,22E,24E)-(1S,3R)-(1,3-Dihydroxy-24a-homo-9,10-secochola-5,7,10(19),22,24-pentaene-24a,24a-diyl)bis [phosphonic acid-bis(1-methylethyl)ester]

(5Z,7E,22E,24E)-(1S,3R)-(1,3-Dihydroxy-24a-homo-9,10-secochola-5,7,10(19),22,24-pentaene-24a,24a-diyl)bis [phosphonic acid dipropyl ester]

(5Z,7E,22E,24E)-(1S,3R)-(1,3-Dihydroxy-24a-homo-9,10-secochola-5,7,10(19),22,24-pentaene-24a,24a-diyl)bis [phosphonic acid dibutyl ester]

(5Z,7E,22E,24E)-(1S,3R)-(1,3-Dihydroxy-24a-homo-9,10-secochola-5,7,10(19),22,24-pentaene-24a,24a-diyl)bis [phosphonic acid]

(5Z,7E,22E,24Z)-(1S,3R)-(24a-Chloro-1,3-dihydroxy-24a-homo-9,10-secochola-5,7,10(19),22,24-pentaen-24a-yl) phosphonic acid dimethyl ester (5Z,7E,22E,24Z)-(1S,3R)-(24a-Chloro-1,3-dihydroxy-24a-homo-9,10-secochola-5,7,10(19),22,24-pentaen-24a-yl) phosphonic acid diethyl ester (5Z,7E,22E,24Z)-(1S,3R)-(24a-Chloro-1,3-dihydroxy-24a-homo-9,10-secochola-5,7,10(19),22,24-pentaen-24a-yl) phosphonic acid-bis(1-methylethyl)ester (5Z,7E,22E,24Z)-(1S,3R)-(24a-Chloro-1,3-dihydroxy-24a-homo-9,10-secochola-5,7,10(19),22,24-pentaen-24a-yl) phosphonic acid dipropyl ester (5Z,7E,22E,24Z)-(1S,3R)-(24a-Chloro-1,3-dihydroxy-24a-homo-9,10-secochola-5,7,10(19),22,24-pentaen-24a-yl) phosphonic acid dibutyl ester (5Z,7E,22E,24Z)-(1S,3R)-(24a-Chloro-1,3-dihydroxy-24a-homo-9,10-secochola-5,7,10(19),22,24-pentaen-24a-yl) phosphonic acid (5Z,7E,22E)-(1S,3R)-(1,3-Dihydroxy-24a-homo-9,10secochola-5,7,10(19),22-tetraen-24-in-24a-yl) phosphonic acid dimethyl ester (5Z,7E,22E)-(1S,3R)-(1,3-Dihydroxy-24a-homo-9,10secochola-5,7,10(19),22-tetraen-24-in-24a-yl) phosphonic acid diethyl ester (5Z,7E,22E)-(1S,3R)-(1,3-Dihydroxy-24a-homo-9,10secochola-5,7,10(19),22-tetraen-24-in-24a-yl) phosphonic acid-bis(1-methylethyl)ester (5Z,7E,22E)-(1S,3R)-(1,3-Dihydroxy-24a-homo-9,10secochola-5,7,10(19),22-tetraen-24-in-24a-yl) phosphonic acid dipropyl ester (5Z,7E,22E)-(1S,3R)-(1,3-Dihydroxy-24a-homo-9,10secochola-5,7,10(19),22-tetraen-24-in-24a-yl) phosphonic acid dibutyl ester (5Z,7E,22E)-(1S,3R)-(1,3-Dihydroxy-24a-homo-9,10secochola-5,7,10(19),22-tetraen-24-in-24a-yl) phosphonic acid-monomethyl ester (5Z,7E,22E)-(1S,3R)-(1,3-Dihydroxy-24a-homo-9,10secochola-5,7,10(19),22-tetraen-24-in-24a-yl) phosphonic acid-monoethyl ester (5Z,7E,22E)-(1S,3R)-(1,3-Dihydroxy-24a-homo-9,10secochola-5,7,10(19),22-tetraen-24-in-24a-yl) phosphonic acid-mono-(1-methylethyl)ester (5Z,7E,22E)-(1S,3R)-(1,3-Dihydroxy-24a-homo-9,10secochola-5,7,10(19),22-tetraen-24-in-24a-yl) phosphonic acid-monopropyl ester (5Z,7E,22E)-(1S,3R)-(1,3-Dihydroxy-24a-homo-9,10secochola-5,7,10(19),22-tetraen-24-in-24a-yl) phosphonic acid-monobutyl ester (5Z,7E,22E)-(1S,3R)-(1,3-Dihydroxy-24a-homo-9,10secochola-5,7,10(19),22-tetraen-24-in-24a-yl) phosphonic acid (5Z,7E,22E)-(1S,3R,24S)-(24a,24a-Dichloro-1,3,24-trihydroxy-24a-homo-9,10-secochola-5,7,10(19),22-tetraen-24a-yl)phosphonic acid dimethyl ester (5Z,7E,22E)-(1S,3R,24R)-(24a,24a-Dichloro-1,3,24-trihydroxy-24a-homo-9,10-secochola-5,7,10(19),22-tetraen-24a-yl)phosphonic acid dimethyl ester (5Z,7E,22E)-(1S,3R,24S)-(24a,24a-Dichloro-1,3,24-trihydroxy-24a-homo-9,10-secochola-5,7,10(19),22-tetraen-24a-yl)phosphonic acid diethyl ester (5Z,7E,22E)-(1S,3R,24R)-(24a,24a-Dichloro-1,3,24-trihydroxy-24a-homo-9,10-secochola-5,7,10(19),22-tetraen-24a-yl)phosphonic acid diethyl ester (5Z,7E,22E)-(1S,3R,24S)-24a,24a-Dichloro-1,3,24-trihydroxy-24a-homo-9,10-secochola-5,7,10(19),22-tetraen-24a-yl)phosphonic acid-bis(1-methylethyl)ester (5Z,7E,22E)-(1S,3R,24R)-(24a,24a-Dichloro-1,3,24-trihydroxy-24a-homo-9,10-secochola-5,7,10(19),22-tetraen-24a-yl)phosphonic acid-bis(1-methylethyl)ester (5Z,7E,22E)-(1S,3R,24S)-(24a,24a-Dichloro-1,3,24-trihydroxy-24a-homo-9,10-secochola-5,7,10(19),22-tetraen-24a-yl)phosphonic acid dipropyl ester (5Z,7E,22E)-(1S,3R,24R)-(24a,24a-Dichloro-1,3,24-trihydroxy-24a-homo-9,10-secochola-5,7,10(19),22-tetraen-24a-yl)phosphonic acid dipropyl ester (5Z,7E,22E)-(1S,3R,24S)-(24a,24a-Dichloro-1,3,24-trihydroxy-24a-homo-9,10-secochola-5,7,10(19),22-tetraen-24a-yl)phosphonic acid dibutyl ester (5Z,7E,22E)-(1S,3R,24R)-(24a,24a-Dichloro-1,3,24-trihydroxy-24a-homo-9,10-secochola-5,7,10(19),22-tetraen-24a-yl)phosphonic acid dibutyl ester (5Z,7E,22E)-(1S,3R,24S)-(24a,24a-Dichloro-1,3,24-trihydroxy-24a-homo-9, 10-secochola-5,7,10(19),22-tetraen-24a-yl)phosphonic acid (5Z,7E,22E)-(1S,3R,24R)-(24a,24a-Dichloro-1,3,24-trihydroxy-24a-homo-9,10-secochola-5,7,10(19),22-tetraen-24a-yl)phosphonic acid (5Z,7E,22E)-(1S,3R,24S)-(24a,24a-Difluoro-1,3,24-trihydroxy-24a-homo-9,10-secochola-5,7,10(19),22-tetraen-24a-yl)phosphonic acid dimethyl ester (5Z,7E,22E)-(1S,3R,24R)-(24a,24a-Difluoro-1,3,24-trihydroxy-24a-homo-9,10-secochola-5,7,10(19),22-tetraen-24a-yl)phosphonic acid dimethyl ester (5Z,7E,22E)-(1S,3R,24S)-(24a,24a-Difluoro-1,3,24-trihydroxy-24a-homo-9,10-secochola-5,7,10(19),22-tetraen-24a-yl)phosphonic acid diethyl ester (5Z,7E,22E)-(1S,3R,24R)-(24a,24a-Difluoro-1,3,24-trihydroxy-24a-homo-9,10-secochola-5,7,10(19),22-tetraen-24a-yl)phosphonic acid diethyl ester (5Z,7E,22E)-(1S,3R,24S)-(24a,24a-Difluoro-1,3,24-trihydroxy-24a-homo-9,10-secochola-5,7,10(19),22-tetraen-24a-yl)phosphonic acid-bis(1-methylethyl)ester (5Z,7E,22E)-(1S,3R,24R)-(24a,24a-Difluoro-1,3,24-trihydroxy-24a-homo-9,10-secochola-5,7,10(19),22-tetraen-24a-yl)phosphonic acid-bis(1-methylethyl)ester (5Z,7E,22E)-(1S,3R,24S)-(24a,24a-Difluoro-1,3,24-trihydroxy-24a-homo-9,10-secochola-5,7,10(19),22-tetraen-24a-yl)phosphonic acid dipropyl ester (5Z,7E,22E)-(1S,3R,24R)-(24a,24a-Difluoro-1,3,24-trihydroxy-24a-homo-9,10-secochola-5,7,10(19),22-tetraen-24a-yl)phosphonic acid dipropyl ester (5Z,7E,22E)-(1S,3R,24S)-(24a,24a-Difluoro-1,3,24-trihydroxy-24a-homo-9,10-secochola-5,7,10(19),22-tetraen-24a-yl)phosphonic acid dibutyl ester (5Z,7E,22E)-(1S,3R,24R)-(24a,24a-Difluoro-1,3,24-trihydroxy-24a-homo-9,10-secochola-5,7,10(19),22-tetraen-24a-yl)phosphonic acid dibutyl ester (5Z,7E,22E)-(1S,3R,24S)-(24a,24a-Difluoro-1,3,24-trihydroxy-24a-homo-9,10-secochola-5,7,10(19),22-tetraen-24a-yl)phosphonic acid (5Z,7E,22E)-(1S,3R)-(24a,24a-Difluoro-1,3-dihydroxy-24-oxo-24a-homo-9,10-secochola-5,7,10(19),22-tetraen-24a-yl)phosphonic acid dimethyl ester (5Z,7E,22E)-(1S,3R)-(24a,24a-Difluoro-1,3-dihydroxy-24-oxo-24a-homo-9,10-secochola-5,7,10(19),22-tetraen-24a-yl)phosphonic acid diethyl ester (5Z,7E,22E)-(1S,3R)-(24a,24a-Difluoro-1,3-dihydroxy-24-oxo-24a-homo-9,10-secochola-5,7,10(19),22-tetraen-24a-yl)phosphonic acid-bis(1-methylethyl)ester (5Z,7E,22E)-(1S,3R)-(24a,24a-Difluoro-1,3-dihydroxy-24-oxo-24a-homo-9,10-secochola-5,7,10(19),22-tetraen-24a-yl)phosphonic acid dipropyl ester (5Z,7E,22E)-(1S,3R)-(24a,24a-Difluoro-1,3-dihydroxy-24-oxo-24a-homo-9,10-secochola-5,7,10(19),22-tetraen-24a-yl)phosphonic acid dibutyl ester (5Z,7E,22E)-(1S,3R)-(24a,24a-Dichloro-1,3-dihydroxy-24-oxo-24a-homo-9,10-secochola-5,7,10(19),22-tetraen-24a-yl)phosphonic acid dimethyl ester (5Z,7E,22E)-(1S,3R)-(24a,24a-Dichloro-1,3-dihydroxy-24-oxo-24a-homo-9,10-secochola-5,7,10(19),22-tetraen-24a-yl)phosphonic acid diethyl ester (5Z,7E,22E)-(1S,3R)-(24a,24a-Dichloro-1,3-dihydroxy-24-oxo-24a-homo-9,10-secochola-5,7,10(19),22-tetraen-24a-yl)phosphonic acid-bis(1-methylethyl)ester (5Z,7E,22E)-(1S,3R)-(24a,24a-Dichloro-1,3-dihydroxy-24-oxo-24a-homo-9,10-secochola-5,7,10(19),22-tetraen-24a-yl)phosphonic acid dipropyl ester (5Z,7E,22E)-(1S,3R)-(24a,24a-Dichloro-1,3-dihydroxy-24-oxo-24a-homo-9,10-secochola-5,7,10(19),22-tetraen-24a-yl)phosphonic acid dibutyl ester (5Z,7E,22E)-(1S,3R)-(26,27-Diethenyl-1,3-dihydroxy-24-oxo-9,10-secocholesta-5,7,10(19),22-tetraen-25-yl)phosphonic acid dimethyl ester (5Z,7E,22E)-(1S,3R)-(26,27-Diethenyl-1,3-dihydroxy-24-oxo-9,10-secocholesta-5,7,10(19),22-tetraen-25-yl)phosphonic acid diethyl ester (5Z,7E,22E)-(1S,3R)-(26,27-Diethenyl-1,3-dihydroxy-24-oxo-9,10-secocholesta-5,7,10(19),22-tetraen-25-yl)phosphonic acid-bis(1-methylethyl)ester (5Z,7E,22E)-(1S,3R)-(26,27-Diethenyl-1,3-dihydroxy-24-oxo-9,10-secocholesta-5,7,10(19),22-tetraen-25-yl)phosphonic acid propyl ester (5Z,7E,22E)-(1S,3R)-(26,27-Diethenyl-1,3-dihydroxy-24-oxo-9,10-secocholesta-5,7,10(19),22-tetraen-25-yl)phosphonic acid butyl ester (5Z,7E,22E)-(1S,3R)-(26,27-Diethenyl-1,3-dihydroxy-24-oxo-9,10-secocholesta-5,7,10(19),22-tetraen-25-yl)phosphonic acid (5Z,7E,22E)-(1S,3R,24ξ)-(1,3-Dihydroxy-26-ethenyl-24-oxo-27-nor-9,10-secocholesta-5,7,10(19),22-tetraen-25-yl)phosphonic acid dimethyl ester (5Z,7E,22E)-(1S,3R,24ξ)-(1,3-Dihydroxy-26-ethenyl-24-oxo-27-nor-9,10-secocholesta-5,7,10(19),22-tetraen-25-yl)phosphonic acid diethyl ester (5Z,7E,22E)-(1S,3R,24ξ)-(1,3-Dihydroxy-26-ethenyl-24-oxo-27-nor-9,10-secocholesta-5,7,10(19),22-tetraen-25-yl)phosphonic acid-bis(1-methylethyl)ester (5Z,7E,22E)-(1S,3R,24ξ)-(1,3-Dihydroxy-26-ethenyl-24-oxo-27-nor-9,10-secocholesta-5,7,10(19),22-tetraen-25-yl)phosphonic acid dipropyl ester (5Z,7E,22E)-(1S,3R,24ξ)-(1,3-Dihydroxy-26-ethenyl-24-oxo-27-nor-9,10-secocholesta-5,7,10(19),22-tetraen-25-yl)phosphonic acid dibutyl ester (5Z,7E,22E)-(1S,3R,24ξ)-(1,3-Dihydroxy-26-ethenyl-24-oxo-27-nor-9,10-secocholesta-5,7,10(19),22-tetraen-25-yl)phosphonic acid (5Z,7E,22E)-(1S,3R)-(1,3-Dihydroxy-24-oxo-9,10-secocholesta-5,7,10(19),22-tetraen-25-yl)phosphonic acid dimethyl ester (5Z,7E,22E)-(1S,3R)-(1,3-Dihydroxy-24-oxo-9,10-secocholesta-5,7,10(19),22-tetraen-25-yl)phosphonic acid diethyl ester (5Z,7E,22E)-(1S,3R)-(1,3-Dihydroxy-24-oxo-9,10-secocholesta-5,7,10(19),22-tetraen-25-yl)phosphonic acid-bis(1-methylethyl)ester (5Z,7E,22E)-(1S,3R)-(1,3-Dihydroxy-24-oxo-9,10-secocholesta-5,7,10(19),22-tetraen-25-yl)phosphonic acid dipropyl ester (5Z,7E,22E)-(1S,3R)-(1,3-Dihydroxy-24-oxo-9,10-secocholesta-5,7,10(19),22-tetraen-25-yl)phosphonic acid dibutyl ester (5Z,7E,22E)-(1S,3R)-(1,3-Dihydroxy-24-oxo-9,10-secocholesta-5,7,10(19),22-tetraen-25-yl)phosphonic acid (5Z,7E,22E)-(1S,3R)-(1,3-Dihydroxy-26,27-dimethyl-24-oxo-9,10-secocholesta-5,7,10(19),22-tetraen-25-yl)phosphonic acid dimethyl ester (5Z,7E,22E)-(1S,3R)-(1,3-Dihydroxy-26,27-dimethyl-24-oxo-9,10-secocholesta-5,7,10(19),22-tetraen-25-yl)phosphonic acid diethyl ester (5Z,7E,22E)-(1S,3R)-(1,3-Dihydroxy-26,27-dimethyl-24-oxo-9,10-secocholesta-5,7,10(19),22-tetraen-25-yl)phosphonic acid-bis(1-methylethyl)ester (5Z,7E,22E)-(1S,3R)-(1,3-Dihydroxy-26,27-dimethyl-24-oxo-9,10-secocholesta-5,7,10(19),22-tetraen-25-yl)phosphonic acid dipropyl ester (5Z,7E,22E)-(1S,3R)-(1,3-Dihydroxy-26,27-dimethyl-24-oxo-9,10-secocholesta-5,7,10(19),22-tetraen-25-yl)phosphonic acid dibutyl ester (5Z,7E,22E)-(1S,3R)-(1,3-Dihydroxy-26,27-dimethyl-24-oxo-9,10-secocholesta-5,7,10(19),22-tetraen-25-yl)phosphonic acid (5Z,7E,22E)-(1S,3R,25R)-(1,3-Dihydroxy-26-methyl-24-oxo-27-nor-9,10-secocholesta-5,7,10(19),22-tetraen-25-yl)phosphonic acid dimethyl ester (5Z,7E,22E)-(1S,3R,25S)-(1,3-Dihydroxy-26-methyl-24-oxo-27-nor-9,10-secocholesta-5,7,10(19),22-tetraen-25-yl)phosphonic acid dimethyl ester (5Z,7E,22E)-(1S,3R,25R)-(1,3-Dihydroxy-26-methyl-24-oxo-27-nor-9,10-secocholesta-5,7,10(19),22-tetraen-25-yl)phosphonic acid diethyl ester (5Z,7E,22E)-(1S,3R,25S)-(1,3-Dihydroxy-26-methyl-24-oxo-27-nor-9,10-secocholesta-5,7,10(19),22-tetraen-25-yl)phosphonic acid diethyl ester (5Z,7E,22E)-(1S,3R,25R)-(1,3-Dihydroxy-26-methyl-24-oxo-27-nor-9,10-secocholesta-5,7,10(19),22-tetraen-25-yl)phosphonic acid-bis(1-methylethyl)ester (5Z,7E,22E)-(1S,3R,25S)-(1,3-Dihydroxy-26-methyl-24-oxo-27-nor-9,10-secocholesta-5,7,10(19),22-tetraen-25-yl)phosphonic acid-bis(1-methylethyl)ester (5Z,7E,22E)-(1S,3R,25R)-(1,3-Dihydroxy-26-methyl-24-oxo-27-nor-9,10-secocholesta-5,7,10(19),22-tetraen-25-yl)phosphonic acid dipropyl ester (5Z,7E,22E)-(1S,3R,25S)-(1,3-Dihydroxy-26-methyl-24-oxo-27-nor-9,10-secocholesta-5,7,10(19),22-tetraen-25-yl)phosphonic acid dipropyl ester (5Z,7E,22E)-(1S,3R,25R)-(1,3-Dihydroxy-26-methyl-24-oxo-27-nor-9,10-secocholesta-5,7,10(19),22-tetraen-25-yl)phosphonic acid dibutyl ester (5Z,7E,22E)-(1S,3R,25S)-(1,3-Dihydroxy-26-methyl-24-oxo-27-nor-9,10-secocholesta-5,7,10(19),22-tetraen-25-yl)phosphonic acid dibutyl ester (5Z,7E,22E)-(1S,3R,25R)-(1,3-Dihydroxy-26-methyl-24-oxo-27-nor-9,10-secocholesta-5,7,10(19),22-tetraen-25-yl)phosphonic acid (5Z,7E,22E)-(1S,3R,25S)-(1,3-Dihydroxy-26-methyl-24-oxo-27-nor-9,10-secocholesta-5,7,10(19),22-tetraen-25-yl)phosphonic acid (5Z,7E,22E)-(1S,3R,24S)-(1,3,24-Trihydroxy-9,10-secochola-5,7,10(19),22-tetraen-24-yl)phosphonic acid dimethyl ester (5Z,7E,22E)-(1S,3R,24R)-(1,3,24-Trihydroxy-9,10-secochola-5,7,10(19),22-tetraen-24-yl)phosphonic acid dimethyl ester (5Z,7E,22E)-(1S,3R,24S)-(1,3,24-Trihydroxy-9,10-secochola-5,7,10(19),22-tetraen-24-yl)phosphonic acid diethyl ester (5Z,7E,22E)-(1S,3R,24R)-(1,3,24-Trihydroxy-9,10-secochola-5,7,10(19),22-tetraen-24-yl)phosphonic acid diethyl ester (5Z,7E,22E)-(1S,3R,24S)-(1,3,24-Trihydroxy-9,10-secochola-5,7,10(19),22-tetraen-24-yl)phosphonic acid-bis(1-methylethyl)ester (5Z,7E,22E)-(1S,3R,24R)-(1,3,24-Trihydroxy-9,10-secochola-5,7,10(19),22-tetraen-24-yl)phosphonic acid-bis(1-methylethyl)ester (5Z,7E,22E)-(1S,3R,24S)-(1,3,24-Trihydroxy-9,10-secochola-5,7,10(19),22-tetraen-24-yl)phosphonic acid dipropyl ester (5Z,7E,22E)-(1S,3R,24R)-(1,3,24-Trihydroxy-9,10-secochola-5,7,10(19),22-tetraen-24-yl)phosphonic acid dipropyl ester (5Z,7E,22E)-(1S,3R,24S)-(1,3,24-Trihydroxy-9,10-secochola-5,7,10(19),22-tetraen-24-yl)phosphonic acid dibutyl ester (5Z,7E,22E)-(1S,3R,24R)-(1,3,24-Trihydroxy-9,10-secochola-5,7,10(19),22-tetraen-24-yl)phosphonic acid dibutyl ester (5Z,7E,22E)-(1S,3R,24S)-(1,3,24-Trihydroxy-9,10-secochola-5,7,10(19),22-tetraen-24-yl)phosphonic acid (5Z,7E,22E)-(1S,3R,24R)-(1,3,24-Trihydroxy-9,10-secochola-5,7,10(19),22-tetraen-24-yl)phosphonic acid (5Z,7E,22E)-(1S,3R)-(1,3-Dihydroxy-24-oxo-9,10-secochola-5,7,10(19),22-tetraen-24-yl)phosphonic acid dimethyl ester (5Z,7E,22E)-(1S,3R)-(1,3-Dihydroxy-24-oxo-9,10-secochola-5,7,10(19),22-tetraen-24-yl)phosphonic acid diethyl ester (5Z,7E,22E)-(1S,3R)-(1,3-Dihydroxy-24-oxo-9,10-secochola-5,7,10(19),22-tetraen-24-yl)phosphonic acid-bis(1-methylethyl)ester (5Z,7E,22E)-(1S,3R)-(1,3-Dihydroxy-24-oxo-9,10-secochola-5,7,10(19),22-tetraen-24-yl)phosphonic acid propyl ester (5Z,7E,22E)-(1S,3R)-(1,3-Dihydroxy-24-oxo-9,10-secochola-5,7,10(19),22-tetraen-24-yl)phosphonic acid dibutyl ester (5Z,7E,22E)-(1S,3R)-(1,3-Dihydroxy-24-oxo-9,10-secochola-5,7,10(19),22-tetraen-24-yl)phosphonic acid (5Z,7E,22E)-(1S,3S)-(1,3-Dihydroxy-24-oxo-24a-homo-9,10-secochola-5,7,10(19),22-tetraen-24a-yl)phosphonic acid dimethyl ester (5Z,7E,22E)-(1S,3S)-(1,3-Dihydroxy-24-oxo-24a-homo-9,10-secochola-5,7,10(19),22-tetraen-24a-yl)phosphonic acid diethyl ester (5Z,7E,22E)-(1S,3S)-(1,3-Dihydroxy-24-oxo-24a-homo-9,10-secochola-5,7,10(19),22-tetraen-24a-yl)phosphonic acid-bis(1-methylethyl)ester (5Z,7E,22E)-(1S,3S)-(1,3-Dihydroxy-24-oxo-24a-homo-9,10-secochola-5,7,10(19),22-tetraen-24a-yl)phosphonic acid dipropyl ester (5Z,7E,22E)-(1S,3S)-(1,3-Dihydroxy-24-oxo-24a-homo-9,10-secochola-5,7,10(19),22-tetraen-24a-yl)phosphonic acid dibutyl ester (5Z,7E,22E)-(1S,3S)-(1,3-Dihydroxy-24-oxo-24a-homo-9,10-secochola-5,7,10(19),22-tetraen-24a-yl)phosphonic acid.

12. A compound of claim 1, wherein $R_1$ and $R_2$ together mean an exocyclic methylene group.

13. A method for producing a pharmaceutical agent which comprises incorporating at least one compound of the formula I of claim 1 together with at least one pharmaceutically acceptable vehicle.

14. A method for therapy of or prophylaxis against osteoporosis which comprises administering to a patient in need thereof a pharmaceutical composition comprising a compound of the formula I of claim 1.

15. A method for generating new bone material in a patient which comprises administering to a patient in need thereof a pharmaceutical composition comprising a compound of the formula I of claim 1.

16. A method for treating a disease characterized by hyperproliferation and deficient cell differentiation which comprises administering to a patient in need thereof a pharmaceutical composition comprising a compound of the formula I of claim 1.

* * * * *